United States Patent
Peters et al.

(10) Patent No.: US 10,150,811 B2
(45) Date of Patent: *Dec. 11, 2018

(54) METHODS FOR TREATING VASCULAR LEAK SYNDROME AND CANCER

(71) Applicant: Aerpio Therapeutics, Inc., Cincinnati, OH (US)

(72) Inventors: Kevin Peters, Cincinnati, OH (US); Robert Shalwitz, Bexley, OH (US)

(73) Assignee: AERPIO THERAPEUTICS, INC., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/438,218

(22) Filed: Feb. 21, 2017

(65) Prior Publication Data

US 2018/0009890 A1  Jan. 11, 2018

Related U.S. Application Data

(63) Continuation of application No. 13/652,203, filed on Oct. 15, 2012.

(60) Provisional application No. 61/546,697, filed on Oct. 13, 2011, provisional application No. 61/546,748, filed on Oct. 13, 2011.

(51) Int. Cl.
| | |
|---|---|
| *A61K 39/395* | (2006.01) |
| *C07K 16/28* | (2006.01) |
| *C07K 14/55* | (2006.01) |
| *A61K 38/20* | (2006.01) |
| *C07K 16/40* | (2006.01) |
| *A61K 39/00* | (2006.01) |

(52) U.S. Cl.
CPC ............. *C07K 16/28* (2013.01); *C07K 16/40* (2013.01); *A61K 38/2013* (2013.01); *A61K 2039/505* (2013.01); *C07K 14/55* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,399,216 A | 8/1983 | Axel et al. |
| 4,496,689 A | 1/1985 | Mitra |
| 4,640,835 A | 2/1987 | Shimizu et al. |
| 4,670,417 A | 6/1987 | Iwasaki et al. |
| 4,740,461 A | 4/1988 | Kaufman |
| 4,791,192 A | 12/1988 | Nakagawa et al. |
| 4,816,567 A | 3/1989 | Cabilly et al. |
| 4,912,040 A | 3/1990 | Kaufman et al. |
| 4,959,455 A | 9/1990 | Clark et al. |
| 5,225,539 A | 7/1993 | Winter |
| 5,545,806 A | 8/1996 | Lonberg et al. |
| 5,545,807 A | 8/1996 | Surani et al. |
| 5,625,825 A | 4/1997 | Rostoker et al. |
| 5,919,813 A | 7/1999 | de Juan, Jr. |
| 5,980,929 A | 11/1999 | De Juan, Jr. |
| 6,075,181 A | 6/2000 | Kucherlapati et al. |
| 6,114,598 A | 9/2000 | Kucherlapati et al. |
| 6,133,426 A | 10/2000 | Gonzalez et al. |
| 6,150,584 A | 11/2000 | Kucherlapati et al. |
| 6,162,963 A | 12/2000 | Kucherlapati et al. |
| 6,455,035 B1 | 9/2002 | Suri et al. |
| 7,052,695 B2 | 5/2006 | Kalish |
| 7,226,755 B1 | 6/2007 | Peters et al. |
| 7,309,483 B2 | 12/2007 | Wiegand et al. |
| 7,354,579 B2 | 4/2008 | Holash et al. |
| 7,507,568 B2 | 3/2009 | Evdokimov et al. |
| 7,589,212 B2 | 9/2009 | Gray et al. |
| 7,622,593 B2 | 11/2009 | Gray et al. |
| 7,632,862 B2 | 12/2009 | Peters et al. |
| 7,740,846 B2 | 6/2010 | Gerber et al. |
| 7,769,575 B2 | 8/2010 | Evdokimov et al. |
| 7,795,444 B2 | 9/2010 | Gray et al. |
| 7,973,142 B2 | 7/2011 | Rotello et al. |
| 8,106,078 B2 | 1/2012 | Gray et al. |
| 8,188,125 B2 | 5/2012 | Gray et al. |
| 8,258,311 B2 | 9/2012 | Gray et al. |
| 8,329,916 B2 | 12/2012 | Gray et al. |
| 8,338,615 B2 | 12/2012 | Gray et al. |
| 8,524,235 B2 | 9/2013 | Rotello et al. |
| 8,569,348 B2 | 10/2013 | Shalwitz et al. |
| 8,846,685 B2 | 9/2014 | Gray et al. |
| 8,883,832 B2 | 11/2014 | Shalwitz et al. |
| 8,895,563 B2 | 11/2014 | Gray et al. |
| 8,946,232 B2 | 2/2015 | Gray et al. |
| 8,968,766 B2 | 3/2015 | Hughes et al. |
| 8,999,325 B2 | 4/2015 | Peters et al. |
| 8,999,953 B2 | 4/2015 | Loftsson et al. |
| 9,096,555 B2 | 8/2015 | Shalwitz et al. |
| 9,126,958 B2 | 9/2015 | Gray et al. |
| 9,174,950 B2 | 11/2015 | Shalwitz et al. |
| 9,248,172 B2 | 2/2016 | Srivastava et al. |
| 9,284,285 B2 | 3/2016 | Gray et al. |
| 9,403,789 B2 | 8/2016 | Eissenstat et al. |
| 9,440,963 B2 | 9/2016 | Peters et al. |
| 9,539,245 B2 | 1/2017 | Peters et al. |
| 9,700,542 B2 | 7/2017 | Breslin et al. |

(Continued)

FOREIGN PATENT DOCUMENTS

| | | |
|---|---|---|
| EP | 1165115 B1 | 5/2003 |
| EP | 1292335 B1 | 5/2007 |

(Continued)

OTHER PUBLICATIONS

Adamsky, et al. Glial tumor cell adhesion is mediated by binding of the FNIII domain of receptor protein tyrosine phosphatase beta (RPTPbeta) to tenascin C. Oncogene. Feb. 1, 2001;20(5):609-18.

(Continued)

*Primary Examiner* — Marianne P Allen
(74) *Attorney, Agent, or Firm* — Wilson Sonsini Goodrich & Rosati

(57) ABSTRACT

Disclosed are methods for treating Vascular Leak Syndrome and preventing cancer metastasis. Further disclosed are methods for treating vascular leakage due to inflammatory diseases, sepsis, cancer or the presence of pathogens.

14 Claims, 7 Drawing Sheets

Specification includes a Sequence Listing.

(56) References Cited

U.S. PATENT DOCUMENTS

| | | |
|---|---|---|
| RE46,592 E | 10/2017 | Gray et al. |
| 9,795,594 B2 | 10/2017 | Gray et al. |
| 9,926,367 B2 | 3/2018 | Rotello et al. |
| 2003/0040463 A1 | 2/2003 | Wiegand et al. |
| 2003/0055006 A1 | 3/2003 | Siemeister et al. |
| 2003/0158083 A1 | 8/2003 | Peters |
| 2004/0077065 A1 | 4/2004 | Evdokimov et al. |
| 2004/0254197 A1 | 12/2004 | Tasaka et al. |
| 2005/0059639 A1 | 3/2005 | Wei |
| 2007/0059762 A1 | 3/2007 | Araki et al. |
| 2007/0154482 A1 | 7/2007 | Sukhatme et al. |
| 2007/0299116 A1 | 12/2007 | Gray et al. |
| 2008/0004267 A1 | 1/2008 | Gray et al. |
| 2008/0076764 A1 | 3/2008 | Peters et al. |
| 2008/0108631 A1 | 5/2008 | Gray et al. |
| 2008/0268051 A1 | 10/2008 | Hughes et al. |
| 2009/0022715 A1 | 1/2009 | Rotello et al. |
| 2009/0227639 A1 | 9/2009 | Gray et al. |
| 2010/0016336 A1 | 1/2010 | Gray et al. |
| 2010/0030487 A1 | 2/2010 | Evdokimov et al. |
| 2010/0056610 A1 | 3/2010 | Peters et al. |
| 2010/0069448 A1 | 3/2010 | Gray et al. |
| 2010/0111894 A1 | 5/2010 | Benny-Ratsaby et al. |
| 2010/0226992 A1 | 9/2010 | Kabra |
| 2010/0256147 A1 | 10/2010 | Hangauer, Jr. |
| 2011/0212951 A1 | 9/2011 | Gray et al. |
| 2011/0268694 A1 | 11/2011 | Shalwitz et al. |
| 2011/0274699 A1 | 11/2011 | Rotello et al. |
| 2012/0077853 A1 | 3/2012 | Gray et al. |
| 2012/0077975 A1 | 3/2012 | Gray et al. |
| 2012/0128625 A1 | 5/2012 | Shalwitz et al. |
| 2012/0129847 A1 | 5/2012 | Peters et al. |
| 2013/0023542 A1 | 1/2013 | Gray et al. |
| 2013/0023543 A1 | 1/2013 | Gray et al. |
| 2013/0095065 A1 | 4/2013 | Peters et al. |
| 2013/0095105 A1 | 4/2013 | Peters et al. |
| 2013/0096140 A1 | 4/2013 | Gray et al. |
| 2013/0137741 A1 | 5/2013 | Kabra et al. |
| 2013/0190324 A1 | 7/2013 | Kompella et al. |
| 2013/0324558 A1 | 12/2013 | Gray et al. |
| 2013/0331386 A1 | 12/2013 | Shalwitz et al. |
| 2014/0010805 A1 | 1/2014 | Hart et al. |
| 2014/0044707 A1 | 2/2014 | Rotello et al. |
| 2014/0066458 A1 | 3/2014 | Shalwitz et al. |
| 2014/0073566 A1 | 3/2014 | Koh et al. |
| 2014/0179693 A1 | 6/2014 | Shalwitz et al. |
| 2014/0221666 A1 | 8/2014 | Gray et al. |
| 2014/0242026 A1 | 8/2014 | Shalwitz et al. |
| 2014/0249100 A1 | 9/2014 | Shalwitz et al. |
| 2014/0275103 A1 | 9/2014 | Peters et al. |
| 2014/0288134 A1 | 9/2014 | Peters et al. |
| 2015/0030603 A1 | 1/2015 | Kim et al. |
| 2015/0050277 A1 | 2/2015 | Peters et al. |
| 2015/0065781 A1 | 3/2015 | Bais et al. |
| 2015/0071941 A1 | 3/2015 | Sodhi et al. |
| 2015/0125455 A1 | 5/2015 | Green et al. |
| 2015/0125542 A1 | 5/2015 | Ohto et al. |
| 2015/0175676 A1 | 6/2015 | Fandl et al. |
| 2015/0190432 A1 | 7/2015 | Doiron et al. |
| 2015/0210656 A1 | 7/2015 | Gray et al. |
| 2015/0232575 A1 | 8/2015 | Peters et al. |
| 2015/0258120 A1 | 9/2015 | Zarnitsyn et al. |
| 2015/0259335 A1 | 9/2015 | Janusz et al. |
| 2015/0290235 A1 | 10/2015 | Gros et al. |
| 2015/0297740 A1 | 10/2015 | Rau et al. |
| 2016/0000871 A1 | 1/2016 | Quaggin |
| 2016/0008327 A1 | 1/2016 | Shalwitz et al. |
| 2016/0015810 A1 | 1/2016 | Deschatelets et al. |
| 2016/0030393 A1 | 2/2016 | Breslin et al. |
| 2016/0038467 A1 | 2/2016 | Peters |
| 2016/0045566 A1 | 2/2016 | Purcell et al. |
| 2016/0058828 A1 | 3/2016 | Dumont et al. |
| 2016/0082129 A1 | 3/2016 | Peters |
| 2016/0130321 A1 | 5/2016 | Burian |
| 2016/0130337 A1 | 5/2016 | Gekkieva et al. |
| 2016/0137717 A1 | 5/2016 | Burian |
| 2016/0144025 A1 | 5/2016 | Vitti et al. |
| 2016/0151410 A1 | 6/2016 | Ma et al. |
| 2016/0151448 A1 | 6/2016 | Van Slyke et al. |
| 2016/0159893 A1 | 6/2016 | Burian et al. |
| 2016/0168240 A1 | 6/2016 | Burian et al. |
| 2016/0220540 A1 | 8/2016 | Peters et al. |
| 2016/0220541 A1 | 8/2016 | Peters et al. |
| 2016/0251421 A1 | 9/2016 | Brown et al. |
| 2016/0252526 A1 | 9/2016 | Bergmann et al. |
| 2016/0374996 A1 | 12/2016 | Gray et al. |
| 2017/0079959 A1 | 3/2017 | Peters |
| 2017/0145416 A1 | 5/2017 | Epstein et al. |
| 2017/0298019 A1 | 10/2017 | Gardner et al. |
| 2018/0092883 A1 | 4/2018 | Peters et al. |

FOREIGN PATENT DOCUMENTS

| | | |
|---|---|---|
| EP | 2004697 A2 | 12/2008 |
| EP | 2371865 A2 | 10/2011 |
| EP | 2385763 A1 | 11/2011 |
| EP | 2451279 A1 | 5/2012 |
| EP | 2142189 B1 | 2/2013 |
| EP | 2592072 A2 | 5/2013 |
| EP | 2592073 A2 | 5/2013 |
| EP | 2624916 A2 | 8/2013 |
| EP | 2766043 A1 | 8/2014 |
| EP | 2766044 A1 | 8/2014 |
| EP | 2041129 B1 | 9/2014 |
| EP | 2041102 B1 | 11/2014 |
| EP | 2803663 A1 | 11/2014 |
| EP | 2038265 B1 | 3/2015 |
| EP | 2967066 A1 | 1/2016 |
| EP | 3168234 A1 | 5/2017 |
| EP | 2371865 B1 | 7/2017 |
| WO | WO-9312227 A1 | 6/1993 |
| WO | WO-9631598 A1 | 10/1996 |
| WO | WO-9818914 A1 | 5/1998 |
| WO | WO-9845331 A2 | 10/1998 |
| WO | WO-0057901 A1 | 10/2000 |
| WO | WO-0065085 A1 | 11/2000 |
| WO | WO-0224782 A1 | 3/2002 |
| WO | WO-03084565 A2 | 10/2003 |
| WO | WO-2006068953 A2 | 6/2006 |
| WO | WO-2006116713 A1 | 11/2006 |
| WO | WO-2007033216 A2 | 3/2007 |
| WO | WO-2007113648 A2 | 10/2007 |
| WO | WO-2007116360 A2 | 10/2007 |
| WO | WO-2008002569 A2 | 1/2008 |
| WO | WO-2008002570 A2 | 1/2008 |
| WO | WO-2008002571 A2 | 1/2008 |
| WO | WO-2008002570 B1 | 4/2008 |
| WO | WO-2008002571 B1 | 4/2008 |
| WO | WO-2009006112 A1 | 1/2009 |
| WO | WO-2009055343 A2 | 4/2009 |
| WO | WO-2009136352 A1 | 11/2009 |
| WO | WO-2010081172 A1 | 7/2010 |
| WO | WO-2011005330 A1 | 1/2011 |
| WO | WO-2011087066 A1 | 7/2011 |
| WO | WO-2012047966 A2 | 4/2012 |
| WO | WO-2013056233 A1 | 4/2013 |
| WO | WO-2013056240 A1 | 4/2013 |
| WO | WO-2014145068 A1 | 9/2014 |
| WO | WO-2015138882 A1 | 9/2015 |
| WO | WO-2015152416 A1 | 10/2015 |
| WO | WO-2016022813 A1 | 2/2016 |
| WO | WO-2016049183 A1 | 3/2016 |
| WO | WO-2017053566 A1 | 3/2017 |

OTHER PUBLICATIONS

Ardelt, et al. Estradiol regulates angiopoietin-1 mRNA expression through estrogen receptor-alpha in a rodent experimental stroke model. Stroke. Feb. 2005;36(2):337-41. Epub Jan. 6, 2005.

Bosse, et al. Only simultaneous blocking of the L- and P-selectin completely inhibits neutrophil migration into mouse peritoneum. Eur J Immunol. Dec. 1994;24(12):3019-24.

(56) References Cited

OTHER PUBLICATIONS

Broermann, et al. Dissociation of VE-PTP from VE-cadherin is required for leukocyte extravasation and for VEGF-induced vascular permeability in vivo. J Exp Med. Nov. 21, 2011;208(12):2393-401. doi: 10.1084/jem.20110525. Epub Oct. 24, 2011.
Bussolino, et al. Molecular mechanisms of blood vessel formation. Trends Biochem Sci. Jul. 1997;22(7):251-6.
Clackson, et al. Making antibody fragments using phage display libraries. Nature. Aug. 15, 1991;352(6336):624-8.
Elias, et al. A literature analysis of prognostic factors for response and quality of response of patients with renal cell carcinoma to interleukin-2-based therapy. Oncology. 2001;61(2):91-101.
European search report and search opinion dated May 11, 2015 for EP Application No. 12840220.3.
Fachinger, et al. Functional interaction of vascular endothelial-protein-tyrosine phosphatase with the angiopoietin receptor Tie-2. Oncogene. Oct. 21, 1999;18(43):5948-53.
Foehr, et al. Targeting of the receptor protein tyrosine phosphatase beta with a monoclonal antibody delays tumor growth in a glioblastoma model. Cancer Res. Feb. 15, 2006;66(4):2271-8.
Folkman. Tumor angiogenesis. The Molecular Basis of Cancer (eds. Mendelsohn, J., Howley, P. M., Israel, M. A. & Liotta, L. A.) Ch. 10. 206-232 (1995).
Fukuhara, et al. Differential function of Tie2 at cell-cell contacts and cell-substratum contacts regulated by angiopoietin-1. Nat Cell Biol. May 2000;10(5):513-26. doi: 10.1038/ncb1714. Epub Apr. 20, 2008.
Gaits, et al. Increase in receptor-like protein tyrosine phosphatase activity and expression level on density-dependent growth arrest of endothelial cells. Biochem J. Oct. 1, 1995;311 ( Pt 1):97-103.
Gallagher et al., Angiopoietin 2 is a Potential Mediator of High-Dose Interleutkin 2-Induced Vascular Leak, Clin Cancer REs (2007);13:2115-2120.
Gotsch, et al. VE-cadherin antibody accelerates neutrophil recruitment in vivo. J Cell Sci. Mar. 1997;110 ( Pt 5):583-8.
Gozes, et al. Anthrax Lethal Toxin Induces Ketotifen-Sensitive Intradermal Vascular Leakage in Certain Inbred Mice Infect Immun. Feb. 2006; 74(2): 1266-1272.
Harder, et al. Characterization and kinetic analysis of the intracellular domain of human protein tyrosine phosphatase 13 (HPTP(3) using synthetic phosphopeptides. Biochem J. 1994; 296:395-401.
Hayashi, et al. VE-PTP regulates VEGFR2 activity in stalk cells to establish endothelial cell polarity and lumen formation. Nat Commun. 2013;4:1672. doi: 10.1038/ncomms2683.
Hudson, et al. Engineered antibodies. Nat Med. Jan. 2003;9(1):129-34.
Imamura, et al. Induction of vascular leakage through release of bradykinin and a novel kinin by cysteine proteinases from *Staphylococcus aureus*. J Exp Med. May 16, 2005;201(10):1669-76.
International search report and written opinion dated Dec. 24, 2012 for PCT/US2012/060273.
Itoh, et al. Purification and characterization of the catalytic domains of the human receptor-linked protein tyrosine phosphatases HPTP beta, leukocyte common antigen (LCA), and leukocyte common antigen-related molecule (LAR). J Biol Chem. Jun. 15, 1992;267(17):12356-63.
Kipriyanov, et al. Generation and production of engineered antibodies. Mol Biotechnol. Jan. 2004;26(1):39-60.
Krueger, et al. Structural diversity and evolution of human receptor-like protein tyrosine phosphatases. EMBO J. Oct. 1990;9(10):3241-52.
Kugathasan, et al. Role of angiopoietin-1 in experimental and human pulmonary arterial hypertension. Chest. Dec. 2005;128(6 Suppl):633S-642S.
Lin, et al. Inhibition of tumor angiogenesis using a soluble receptor establishes a role for Tie2 in pathologic vascular growth. J Clin Invest. Oct. 15, 1997;100(8):2072-8.
Lo. Antibody humanization by CDR grafting. Methods Mol Biol. 2004;248:135-59.

Lorente, et al. Functional comparison of long and short splice forms of RPTPbeta: implications for glioblastoma treatment. Neuro Oncol. Apr. 2005;7(2):154-63.
Luo, et al. Molecular mechanism underlying the action of a novel fusion inhibitor of influenza A virus. J Virol. May 1997;71(5):4062-70.
Marneros, et al. Endogenous endostatin inhibits choroidal neovascularization. FASEB J. Dec. 2007;21(14):3809-18. Epub May 25, 2007.
Mellberg, et al. Transcriptional profiling reveals a critical role for tyrosine phosphatase VE-PTP in regulation of VEGFR2 activity and endothelial cell morphogenesis. FASEB J. May 2009;23(5):1490-502. doi: 10.1096/fj.08-123810. Epub Jan. 9, 2009.
Miles, et al. Vascular reactions to histamine, histamine-liberator and leukotaxine in the skin of guinea-pigs. J Physiol. Oct. 1952;118(2):228-57.
Morrison, et al. Chimeric human antibody molecules: mouse antigen-binding domains with human constant region domains. Proc Natl Acad Sci U S A. Nov. 1984;81(21):6851-5.
Morrissey, et al. Differential expression of angiogenesis associated genes in prostate cancer bone, liver and lymph node metastases. Clin Exp Metastasis. 2008;25(4):377-88. Epub Oct. 31, 2007.
Muller, et al. A role for receptor tyrosine phosphatase zeta in glioma cell migration. Oncogene. Oct. 2, 2003;22(43):6661-8.
Muller, et al. Receptor protein tyrosine phosphatase zeta as a therapeutic target for glioblastoma therapy. Expert Opin Ther Targets. Jun. 2004;8(3):211-20.
Muyldermans. Single domain camel antibodies: current status. J Biotechnol. Jun. 2001;74(4):277-302.
Nguyen, et al. Cellular interactions in vascular growth and differentiation. Int Rev Cytol. 2001;204:1-48.
Nottebaum et al. VE-PTP maintains the endothelial barrier via plakoglobin and becomes dissociated from VE-cadherin by leukocytes and by VEGF. J Exp Med. Nov. 24, 2008;205(12):2929-45. doi: 10.1084/jem.20080406. Epub Nov. 17, 2008.
Oliner, et al. Suppression of angiogenesis and tumor growth by selective inhibition of angiopoietin-2. Cancer Cell. Nov. 2004;6(5):507-16.
O'Reilly, et al. Angiostatin: a novel angiogenesis inhibitor that mediates the suppression of metastases by a Lewis lung carcinoma. Cell. Oct. 21, 1994;79(2):315-28.
O'Reilly, et al. Endostatin: an endogenous inhibitor of angiogenesis and tumor growth. Cell. Jan. 24, 1997;88(2):277-85.
Park, et al. Effect of sorafenib on experimental choroidal neovascularization in the rat. Clin Experiment Ophthalmol. Oct. 2010;38(7):718-26. doi: 10.1111/j.1442-9071.2010.02328.x. Epub Jul. 9, 2010.
Riemer, et al. Matching of trastuzumab (Herceptin) epitope mimics onto the surface of Her-2/neu—a new method of epitope definition. Mol Immunol. May 2005;42(9):1121-4. Epub Jan. 8, 2005.
Saharinen, et al., Angiopoietins assemble distinct Tie2 signalling complexes in endothelial cell-cell and cell-matrix contacts. Nat Cell Biol. May 2008;10(5):527-37. doi: 10.1038/ncb1715. Epub Apr. 20, 2008.
Schindelholz, et al. Regulation of CNS and motor axon guidance in *Drosophila* by the receptor tyrosine phosphatase DPTP52F. Development. Nov. 2001;128(21):4371-82.
Shen, et al. In vivo immunostaining demonstrates macrophages associate with growing and regressing vessels. Invest Ophthalmol Vis Sci. Sep. 2007;48(9):4335-41.
Sidwell, et al. Utilization of pulse oximetry for the study of the inhibitory effects of antiviral agents on influenza virus in mice. Antimicrob Agents Chemother. Feb. 1992;36(2):473-6.
Smith, et al. Oxygen-induced retinopathy in the mouse. Invest Ophthalmol Vis Sci. Jan. 1994;35(1):101-11.
Stancovski, et al. Mechanistic aspects of the opposing effects of monoclonal antibodies to the ERBB2 receptor on tumor growth. Proc Natl Acad Sci U S A. Oct. 1, 1991;88(19):8691-5.
Suri, et al. Increased vascularization in mice overexpressing angiopoietin-1. Science. Oct. 16, 1998;282(5388):468-71.
Thurston. Complementary actions of VEGF and angiopoietin-1 on blood vessel growth and leakage. J Anat. Jun. 2002;200(6):575-80.
Thurston, et al. Angiopoietin-1 protects the adult vasculature against plasma leakage. Nat Med. Apr. 2000;6(4):460-3.

(56) References Cited

OTHER PUBLICATIONS

Tobe, et al. Targeted disruption of the FGF2 gene does not prevent choroidal neovascularization in a murine model. Am J Pathol. Nov. 1998;153(5):1641-6.

Ulbricht, et al. Expression and function of the receptor protein tyrosine phosphatase zeta and its ligand pleiotrophin in human astrocytomas. J Neuropathol Exp Neurol. Dec. 2003;62(12):1265-75.

Van Der Flier, et al. Antibody neutralization of vascular endothelial growth factor (VEGF) fails to attenuate vascular permeability and brain edema in experimental pneumococcal meningitis. J Neuroimmunol. Mar. 2005;160(1-2):170-7.

Varughese, et al. Internalization of a Bacillus anthracis protective antigen-c-Myc fusion protein mediated by cell surface anti-c-Myc antibodies. Mol Med. Feb. 1998;4(2):87-95.

Winderlich, et al. VE-PTP controls blood vessel development by balancing Tie-2 activity. J Cell Biol. May 18, 2009;185(4):657-71. doi: 10.1083/jcb.200811159.

Witte, et al. Monoclonal antibodies targeting the VEGF receptor-2 (FIk1/KDR) as an anti-angiogenic therapeutic strategy. Cancer Metastasis Rev. Jun. 1998;17(2):155-61.

Wright, et al. Protein-tyrosine phosphatases in the vessel wall: differential expression after acute arterial injury. Arterioscler Thromb Vasc Biol. May 2000;20(5):1189-98.

Wu, et al. Humanization of a murine monoclonal antibody by simultaneous optimization of framework and CDR residues. J Mol Biol. Nov. 19, 1999;294(1):151-62.

Yacyshyn, et al. Tyrosine phosphatase beta regulates angiopoietin-Tie2 signaling in human endothelial cells. Angiogenesis. 2009;12(1):25-33. doi: 10.1007/s10456-008-9126-0. Epub Jan. 1, 2009.

Yancopoulos, et al. Vascular-specific growth factors and blood vessel formation. Nature. Sep. 14, 2000; 407(6801):242-8.

Yu, et al. Interaction between bevacizumab and murine VEGF-A: a reassessment. Invest Ophthalmol Vis Sci. Feb. 2008;49(2):522-7. doi: 10.1167/iovs.07-1175.

Jeansson, et al., Angiopoietin-1 is essential in mouse vasculature during development and in response to injury, The Journal of Clinical Investigation, Jun. 2011, 121(6):2278-89.

Nawroth, et al. VE-PTP and VE-cadherin ectodomains interact to facilitate regulation of phosphorylation and cell contacts. EMBO J. Sep. 16, 2002;21(18):4885-95.

Vestweber, et al., Molecular Mechanisms That Control Endothelial Cell Contacts, J. Pathol 2000, 190:281-91.

Shintei, et al., Newly Revised Disease and Drugs, Yakuji Nippo Limited, 1986 (Third print), p. 504-510. (English Translation).

Sone, et al. Effects of intraocular or systemic administration of neutralizing antibody against vascular endothelial growth factor on the murine experimental model of retinopathy. Life Sci. 1999;65(24):2573-80.

Office action dated Sep. 11, 2013 for U.S. Appl. No. 13/652,203.
Office action dated Apr. 17, 2015 for U.S. Appl. No. 13/652,203.
Office action dated May 15, 2014 for U.S. Appl. No. 13/652,203.
Office action dated Aug. 22, 2016 for U.S. Appl. No. 13/652,203.
Office action dated Jan. 4, 2016 for U.S. Appl. No. 13/652,203.

Baumer, et al. Vascular endothelial cell-specific phosphotyrosine phosphatase (VE-PTP) activity is required for blood vessel development. Blood. Jun. 15, 2006;107(12):4754-62. Epub Mar. 2, 2006.

Doukas, et al. Topical administration of a multi-targeted kinase inhibitor suppresses choroidal neovascularization and retinal edema. J Cell Physiol. Jul. 2008;216(1):29-37. doi: 10.1002/jcp.21426.

Fukuhara, et al. Vascular endothelial cells and adjoining cells for their mutual adhesion/interaction for stabilization and angiogenesis. Seikagaku. Apr. 2010;82(4):290-301.

Journal of the Showa Medical Association, 2010, vol. 70, No. 1, pp. 45-51.

Lip, et al. Plasma vascular endothelial growth factor, angiopoietin-2, and soluble angiopoietin receptor tie-2 in diabetic retinopathy: effects of laser photocoagulation and angiotensin receptor blockade. Br J Ophthalmol. Dec. 2004;88(12):1543-6.

Nguyen, et al. Vascular endothelial growth factor is a critical stimulus for diabetic macular edema. Am J Ophthalmol. Dec. 2006;142(6):961-9. Epub Aug. 2, 2006.

Praidou, et al. Angiogenic growth factors and their inhibitors in diabetic retinopathy. Curr Diabetes Rev. Sep. 2010;6(5):304-12.

U.S. Appl. No. 15/463,340 Office Action dated Jul. 9, 2018.

SEQUENCE LISTING

```
<160> NUMBER OF SEQ ID NOS: 7

<210> SEQ ID NO 1
<211> LENGTH: 6045
<212> TYPE: DNA
<213> ORGANISM: Homo sapiens

<400> SEQUENCE: 1
atgctgagcc atggagccgg gttggccttg tggatcacac tgagcctgct gcagactgga      60
ctggcggagc cagagagatg taacttcacc ctggcggagt ccaaggcctc cagccattct     120
gtgtctatcc agtggagaat tttgggctca ccctgtaact ttagcctcat ctatagcagt     180
gacaccctgg gggccgcgtt gtgccctacc tttcggatag acaacaccac atacggatgt     240
aaccttcaag atttacaagc aggaaccatc tataacttca agattatttc tctggatgaa     300
gagagaactg tggtcttgca aacagatcct ttacctcctg ctaggtttgg agtcagtaaa     360
gagaagacga cttcaaccgg cttgcatgtt tggtggactc cttcttccgg aaaagtcacc     420
tcatatgagg tgcaattatt tgatgaaaat aaccaaaaga tacaggggt tcaaattcaa     480 gaaagtactt catggaatga atacactttt ttcaatctca ctgctggtag taaatacaat     540
attgccatca cagctgtttc tggaggaaaa cgttcttttt cagtttatac caatggatca     600
acagtgccat ctccagtgaa agatattggt atttccacaa aagccaattc tctcctgatt     660
tcctggtccc atggttctgg gaatgtggaa cgataccggc tgatgctaat ggataaaggg     720
atcctagttc atgcggtgt tgtggacaaa catgctactt cctatgcttt tcacgggctg     780
tcccctggct acctctacaa cctcactgtt atgactgagg ctgcagggct gcaaaactac     840
aggtggaaac tagtcaggac agcccccatg gaagtctcaa atctgaaggt gacaaatgat     900
ggcagtttga cctctctaaa agtcaaatgg caaagacctc ctggaaatgt ggattcttac     960
aatatcaccc tgtctcacaa agggaccatc aaggaatcca gagtattagc accttggatt    1020
actgaaactc acttaaaga gttagtcccc ggtcgacttt atcaagttac tgtcagctgt    1080
```

```
gtctctggtg aactgtctgc tcagaagatg gcagtgggca gaacatttcc agacaaagtt    1140
gcaaacctgg aggcaaacaa taatggcagg atgaggtctc ttgtagtgag ctggtcgccc    1200
cctgctggag actgggagca gtatcggatc ctactcttca atgattctgt ggtgctgctc    1260
aacatcactg tgggaaagga agaaacacag tatgtcatgg atgacacggg gctcgtaccg    1320
ggaagacagt atgaggtgga agtcattgtt gagagtggaa atttgaagaa ttctgagcgt    1380
tgccaaggca ggacagtccc cctggctgtc ctccagcttc gtgtcaaaca tgccaatgaa    1440
acctcactga gtatcatgtg cagaccccct gtagcagaat gggagaaata catcatttcc    1500
ctagctgaca gagacctctt actgatccac aagtcactct ccaaagatgc caaagaattc    1560
acttttactg acctggtgcc tggacgaaaa tacatggcta cagtcaccag tattagtgga    1620
gacttaaaaa attcctcttc agtaaaagga agaacagtgc ctgcccaagt gactgacttg    1680
catgtggcca accaaggaat gaccagtagt ctgtttacta actggaccca ggcacaagga    1740
gacgtagaat tttaccaagt cttactgatc catgaaaatg tggtcattaa aaatgaaagc    1800
atctccagtg agaccagcag atacagcttc cactctctca gtccggcag cctgtactcc    1860 gtggtggtaa caacagtgag tggagggatc tcttcccgac aagtggttgt ggagggaaga    1920
acagtccctt ccagtgtgag tggagtaacg gtgaacaatt ccggtcgtaa tgactacctc    1980
agcgtttcct ggctcgtggc gcccggagat gtggataact atgaggtaac attgtctcat    2040
gacggcaagg tggttcagtc ccttgtcatt gccaagtctg tcagagaatg ttccttcagc    2100
tccctcaccc caggccgcct ctacaccgtg accataacta aaggagtgg caagtatgaa    2160 aatcactcct tcagccaaga gcggacagtg cctgacaaag tccagggagt cagtgttagc    2220
aactcagcca ggagtgacta tttaagggta tcctgggtgc atgccactgg agactttgat    2280
cactatgaag tcaccattaa aaacaaaaac aacttcattc aaactaaaag cattcccaag    2340
tcagaaaacg aatgtgtatt tgttcagcta gtccctggac ggttgtacag tgtcactgtt    2400
actacaaaaa gtgacaata tgaagccaat gaacaaggga tgggagaac aattccagag    2460 cctgttaagg atctaacatt gcgcaacagg agcactgagg acttgcatgt gacttggtca    2520
ggagctaatg gggatgtcga ccaatatgag atccagctgc tcttcaatga catgaaagta    2580
tttcctcctt ttcaccttgt aaataccgca accgagtatc gatttacttc cctaacacca    2640
ggccgccaat acaaaattct tgtcttgacg attagcgggg atgtacagca gtcagccttc    2700
attgagggct tcacagttcc tagtgctgtc aaaaatattc acatttctcc caatggagca    2760
acagatagcc tgacggtgaa ctggactcct ggtggggag acgttgattc ctacacggtg    2820
tcggcattca ggcacagtca aaaggttgac tctcagacta ttcccaagca cgtctttgag    2880
cacacgttcc acagactgga ggccggggag cagtaccaga tcatgattgc ctcagtcagc    2940
gggtccctga gaatcagat aaatgtggtt gggcggacag ttccagcatc tgtccaagga    3000
gtaattgcag acaatgcata cagcagttat tccttaatag taagttggca aaaagctgct    3060
ggtgtggcag aaagatatga tatcctgctt ctaactgaaa atggaatcct tctgcgcaac    3120
acatcagagc cagccaccac taagcaacac aaatttgaag atctaacacc aggcaagaaa    3180
tacaagatac agatcctaac tgtcagtgga ggcctctta gcaaggaagc ccagactgaa    3240
ggccgaacag tcccagcagc tgtcaccgac ctgaggatca cagagaactc caccaggcac    3300
ctgtccttcc gctggaccgc ctcagagggg gagctcagct ggtacaacat cttttttgtac    3360 aacccagatg ggaatctcca ggagagagct caagttgacc cactagtcca gagcttctct    3420
ttccagaact tgctacaagg cagaatgtac aagatggtga ttgtaactca cagtggggag    3480
```

```
ctgtctaatg agtctttcat atttggtaga acagtcccag cctctgtgag tcatctcagg    3540
gggtccaatc ggaacacgac agacagcctt tggttcaact ggagtccagc ctctggggac    3600
tttgactttt atgagctgat tctctataat cccaatggca caaagaagga aaactggaaa    3660
gacaaggacc tgacggagtg gcggtttcaa ggccttgttc ctggaaggaa gtacgtgctg    3720
tgggtggtaa ctcacagtgg agatctcagc aataaagtca cagcggagag cagaacagct    3780
ccaagtcctc ccagtcttat gtcatttgct gacattgcaa acacatcctt ggccatcacg    3840
tggaaagggc ccccagactg gacagactac aacgactttg agctgcagtg gttgcccaga    3900
gatgcactta ctgtcttcaa cccctacaac aacagaaaat cagaaggacg cattgtgtat    3960
ggtcttcgtc cagggagatc ctatcaattc aacgtcaaga ctgtcagtgg tgattcctgg    4020
aaaacttaca gcaaaccaat ttttggatct gtgaggacaa agcctgacaa gatacaaaac    4080
ctgcattgcc ggcctcagaa ctccacggcc attgctgtt cttggatccc tcctgattct    4140
gactttgatg ttatagtat tgaatgccgg aaaatggaca cccaagaagt tgagttttcc    4200
agaaagctgg agaaagaaaa atctctgctc aacatcatga tgctagtgcc ccataagagg    4260
tacctggtgt ccatcaaagt gcagtcggcc ggcatgacca cgcgaggtgg tgaagacagc    4320
actatcacaa tgatagaccg ccccccctcct ccacccccac acattcgtgt gaatgaaaag    4380
gatgtgctaa ttagcaagtc ttccatcaac tttactgtca actgcagctg gttcagcgac    4440
accaatggag ctgtgaaata cttcacagtg gtggtgagag aggctgatgg cagtgatgag    4500
ctgaagccag aacagcagca ccctctccct tcctacctgg agtacaggca caatgcctcc    4560
attcgggtgt atcagactaa ttattttgcc agcaaatgtg ccgaaaatcc taacagcaac    4620
tccaagagtt ttaacattaa gcttggagca gagatggaga gcttaggtgg aaaacgcgat    4680
cccactcagc aaaaattctg tgatggacca ctgaagccac acactgccta cagaatcagc    4740
attgagctt ttacacagct ctttgatgag gacctgaagg aattcacaaa gccactctat    4800
tcagacacat tttttctttt acccatcact actgaatcag agcccttgtt tggagctatt    4860
gaaggtgtga gtgctggtct gttttttaatt ggcatgctag tggctgttgt tgccttattg    4920
atctgcagac agaaagtgag ccatggtcga gaaagaccct ctgcccgtct gagcattcgt    4980
agggatcgac cattatctgt ccacttaaac ctgggccaga aggtaaccg gaaaacttct    5040
tgtccaataa aaataaatca gtttgaaggg catttcatga agctacaggc tgactccaac    5100
taccttctat ccaaggaata cgaggagtta aaagacgtgg gccgaaacca gtcatgtgac    5160
attgcactct tgccggagaa tagagggaaa aatcgataca caatatatt gccctatgat    5220
gccacgcgag tgaagctctc caatgtagat gatgatcctt gctctgacta catcaatgcc    5280
agctacatcc ctggcaacaa cttcagaaga gaatacattg tcactcaggg accgcttcct    5340
ggcaccaagg atgacttctg gaaaatggtg tgggaacaaa acgttcacaa catcgtcatg    5400
gtgacccagt gtgttgagaa gggccgagta aagtgtgacc attactggcc agcggaccag    5460
gattccctct actatgggga cctcatcctg cagatgctct cagagtccgt cctgcctgag    5520
tggaccatcc gggagtttaa gatatgcggt gaggaacagc ttgatgcaca cagactcatc    5580
cgccactttc actatacggt gtggccagac catgagtcc cagaaccac ccagtctctg    5640
atccagttgt gagaactgt cagggactac atcaacagaa gcccgggtgc tgggcccact    5700
gtggtgcact gcagtgctgg tgtgggtagg actggaacct ttattgcatt ggaccgaatc    5760
ctccagcagt tagactccaa agactctgtg gacatttatg gagcagtgca cgacctaaga    5820
```

-continued

```
cttcacaggg ttcacatggt ccagactgag tgtcagtatg tctacctaca tcagtgtgta      5880
agagatgtcc tcagagcaag aaagctacgg agtgaacaag aaaacccctt gtttccaatc      5940
tatgaaaatg tgaatccaga gtatcacaga gatccagtct attcaaggca ttgagaatgt      6000
acctgaagag ctcctggata aaattattc actgtgtgat ttgtt                      6045
```

<210> SEQ ID NO 2
<211> LENGTH: 1997
<212> TYPE: PRT
<213> ORGANISM: Homo sapiens

<400> SEQUENCE: 2

```
Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
            20                  25                  30

Glu Ser Lys Ala Ser Ser His Ser Val Ser Ile Gln Trp Arg Ile Leu
        35                  40                  45

Gly Ser Pro Cys Asn Phe Ser Leu Ile Tyr Ser Ser Asp Thr Leu Gly
    50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Arg Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Ser Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190

Phe Ser Val Tyr Thr Asn Gly Ser Thr Val Pro Ser Pro Val Lys Asp
        195                 200                 205

Ile Gly Ile Ser Thr Lys Ala Asn Ser Leu Leu Ile Ser Trp Ser His
    210                 215                 220

Gly Ser Gly Asn Val Glu Arg Tyr Arg Leu Met Leu Met Asp Lys Gly
225                 230                 235                 240

Ile Leu Val His Gly Gly Val Val Asp Lys His Ala Thr Ser Tyr Ala
                245                 250                 255

Phe His Gly Leu Thr Pro Gly Tyr Leu Tyr Asn Leu Thr Val Met Thr
            260                 265                 270

Glu Ala Ala Gly Leu Gln Asn Tyr Arg Trp Lys Leu Val Arg Thr Ala
        275                 280                 285

Pro Met Glu Val Ser Asn Leu Lys Val Thr Asn Asp Gly Ser Leu Thr
    290                 295                 300

Ser Leu Lys Val Lys Trp Gln Arg Pro Pro Gly Asn Val Asp Ser Tyr
305                 310                 315                 320

Asn Ile Thr Leu Ser His Lys Gly Thr Ile Lys Glu Ser Arg Val Leu
                325                 330                 335
```

```
Ala Pro Trp Ile Thr Glu Thr His Phe Lys Glu Leu Val Pro Gly Arg
            340                 345                 350

Leu Tyr Gln Val Thr Val Ser Cys Val Ser Gly Glu Leu Ser Ala Gln
        355                 360                 365

Lys Met Ala Val Gly Arg Thr Phe Pro Asp Lys Val Ala Asn Leu Glu
    370                 375                 380

Ala Asn Asn Asn Gly Arg Met Arg Ser Leu Val Val Ser Trp Ser Pro
385                 390                 395                 400

Pro Ala Gly Asp Trp Glu Gln Tyr Arg Ile Leu Leu Phe Asn Asp Ser
                405                 410                 415

Val Val Leu Leu Asn Ile Thr Val Gly Lys Glu Glu Thr Gln Tyr Val
            420                 425                 430

Met Asp Asp Thr Gly Leu Val Pro Gly Arg Gln Tyr Glu Val Glu Val
        435                 440                 445

Ile Val Glu Ser Gly Asn Leu Lys Asn Ser Glu Arg Cys Gln Gly Arg
    450                 455                 460

Thr Val Pro Leu Ala Val Leu Gln Leu Arg Val Lys His Ala Asn Glu
465                 470                 475                 480

Thr Ser Leu Ser Ile Met Trp Gln Thr Pro Val Ala Glu Trp Glu Lys
                485                 490                 495

Tyr Ile Ile Ser Leu Ala Asp Arg Asp Leu Leu Leu Ile His Lys Ser
            500                 505                 510

Leu Ser Lys Asp Ala Lys Glu Phe Thr Phe Thr Asp Leu Val Pro Gly
        515                 520                 525

Arg Lys Tyr Met Ala Thr Val Thr Ser Ile Ser Gly Asp Leu Lys Asn
    530                 535                 540

Ser Ser Ser Val Lys Gly Arg Thr Val Pro Ala Gln Val Thr Asp Leu
545                 550                 555                 560

His Val Ala Asn Gln Gly Met Thr Ser Ser Leu Phe Thr Asn Trp Thr
                565                 570                 575

Gln Ala Gln Gly Asp Val Glu Phe Tyr Gln Val Leu Leu Ile His Glu
            580                 585                 590

Asn Val Val Ile Lys Asn Glu Ser Ile Ser Ser Glu Thr Ser Arg Tyr
        595                 600                 605

Ser Phe His Ser Leu Lys Ser Gly Ser Leu Tyr Ser Val Val Val Thr
    610                 615                 620

Thr Val Ser Gly Gly Ile Ser Ser Arg Gln Val Val Glu Gly Arg
625                 630                 635                 640

Thr Val Pro Ser Ser Val Ser Gly Val Thr Val Asn Asn Ser Gly Arg
                645                 650                 655

Asn Asp Tyr Leu Ser Val Ser Trp Leu Leu Ala Pro Gly Asp Val Asp
            660                 665                 670

Asn Tyr Glu Val Thr Leu Ser His Asp Gly Lys Val Val Gln Ser Leu
        675                 680                 685

Val Ile Ala Lys Ser Val Arg Glu Cys Ser Phe Ser Ser Leu Thr Pro
    690                 695                 700

Gly Arg Leu Tyr Thr Val Thr Ile Thr Thr Arg Ser Gly Lys Tyr Glu
705                 710                 715                 720

Asn His Ser Phe Ser Gln Glu Arg Thr Val Pro Asp Lys Val Gln Gly
                725                 730                 735

Val Ser Val Ser Asn Ser Ala Arg Ser Asp Tyr Leu Arg Val Ser Trp
            740                 745                 750

Val His Ala Thr Gly Asp Phe Asp His Tyr Glu Val Thr Ile Lys Asn
```

-continued

```
            755                 760                 765
Lys Asn Asn Phe Ile Gln Thr Lys Ser Ile Pro Lys Ser Glu Asn Glu
        770                 775                 780
Cys Val Phe Val Gln Leu Val Pro Gly Arg Leu Tyr Ser Val Thr Val
785                 790                 795                 800
Thr Thr Lys Ser Gly Gln Tyr Glu Ala Asn Glu Gln Gly Asn Gly Arg
                805                 810                 815
Thr Ile Pro Glu Pro Val Lys Asp Leu Thr Leu Arg Asn Arg Ser Thr
                820                 825                 830
Glu Asp Leu His Val Thr Trp Ser Gly Ala Asn Gly Asp Val Asp Gln
                835                 840                 845
Tyr Glu Ile Gln Leu Leu Phe Asn Asp Met Lys Val Phe Pro Pro Phe
        850                 855                 860
His Leu Val Asn Thr Ala Thr Glu Tyr Arg Phe Thr Ser Leu Thr Pro
865                 870                 875                 880
Gly Arg Gln Tyr Lys Ile Leu Val Leu Thr Ile Ser Gly Asp Val Gln
                        885                 890                 895
Gln Ser Ala Phe Ile Glu Gly Phe Thr Val Pro Ser Ala Val Lys Asn
                900                 905                 910
Ile His Ile Ser Pro Asn Gly Ala Thr Asp Ser Leu Thr Val Asn Trp
        915                 920                 925
Thr Pro Gly Gly Gly Asp Val Asp Ser Tyr Thr Val Ser Ala Phe Arg
        930                 935                 940
His Ser Gln Lys Val Asp Ser Gln Thr Ile Pro Lys His Val Phe Glu
945                 950                 955                 960
His Thr Phe His Arg Leu Glu Ala Gly Glu Gln Tyr Gln Ile Met Ile
                965                 970                 975
Ala Ser Val Ser Gly Ser Leu Lys Asn Gln Ile Asn Val Gly Arg
                980                 985                 990
Thr Val Pro Ala Ser Val Gln Gly  Val Ile Ala Asp Asn  Ala Tyr Ser
        995                 1000                1005
Ser Tyr  Ser Leu Ile Val Ser  Trp Gln Lys Ala Ala  Gly Val Ala
    1010                1015                1020
Glu Arg  Tyr Asp Ile Leu Leu  Leu Thr Glu Asn Gly  Ile Leu Leu
    1025                1030                1035
Arg Asn  Thr Ser Glu Pro Ala  Thr Thr Lys Gln His  Lys Phe Glu
    1040                1045                1050
Asp Leu  Thr Pro Gly Lys Lys  Tyr Lys Ile Gln Ile  Leu Thr Val
    1055                1060                1065
Ser Gly  Gly Leu Phe Ser Lys  Glu Ala Gln Thr Glu  Gly Arg Thr
    1070                1075                1080
Val Pro  Ala Ala Val Thr Asp  Leu Arg Ile Thr Glu  Asn Ser Thr
    1085                1090                1095
Arg His  Leu Ser Phe Arg Trp  Thr Ala Ser Glu Gly  Glu Leu Ser
    1100                1105                1110
Trp Tyr  Asn Ile Phe Leu Tyr  Asn Pro Asp Gly Asn  Leu Gln Glu
    1115                1120                1125
Arg Ala  Gln Val Asp Pro Leu  Val Gln Ser Phe Ser  Phe Gln Asn
    1130                1135                1140
Leu Leu  Gln Gly Arg Met Tyr  Lys Met Val Ile Val  Thr His Ser
    1145                1150                1155
Gly Glu  Leu Ser Asn Glu Ser  Phe Ile Phe Gly Arg  Thr Val Pro
    1160                1165                1170
```

```
Ala Ser Val Ser His Leu Arg Gly Ser Asn Arg Asn Thr Thr Asp
1175            1180             1185

Ser Leu Trp Phe Asn Trp Ser Pro Ala Ser Gly Asp Phe Asp Phe
1190            1195             1200

Tyr Glu Leu Ile Leu Tyr Asn Pro Asn Gly Thr Lys Lys Glu Asn
1205            1210             1215

Trp Lys Asp Lys Asp Leu Thr Glu Trp Arg Phe Gln Gly Leu Val
1220            1225             1230

Pro Gly Arg Lys Tyr Val Leu Trp Val Val Thr His Ser Gly Asp
1235            1240             1245

Leu Ser Asn Lys Val Thr Ala Glu Ser Arg Thr Ala Pro Ser Pro
1250            1255             1260

Pro Ser Leu Met Ser Phe Ala Asp Ile Ala Asn Thr Ser Leu Ala
1265            1270             1275

Ile Thr Trp Lys Gly Pro Pro Asp Trp Thr Asp Tyr Asn Asp Phe
1280            1285             1290

Glu Leu Gln Trp Leu Pro Arg Asp Ala Leu Thr Val Phe Asn Pro
1295            1300             1305

Tyr Asn Asn Arg Lys Ser Glu Gly Arg Ile Val Tyr Gly Leu Arg
1310            1315             1320

Pro Gly Arg Ser Tyr Gln Phe Asn Val Lys Thr Val Ser Gly Asp
1325            1330             1335

Ser Trp Lys Thr Tyr Ser Lys Pro Ile Phe Gly Ser Val Arg Thr
1340            1345             1350

Lys Pro Asp Lys Ile Gln Asn Leu His Cys Arg Pro Gln Asn Ser
1355            1360             1365

Thr Ala Ile Ala Cys Ser Trp Ile Pro Pro Asp Ser Asp Phe Asp
1370            1375             1380

Gly Tyr Ser Ile Glu Cys Arg Lys Met Asp Thr Gln Glu Val Glu
1385            1390             1395

Phe Ser Arg Lys Leu Glu Lys Glu Lys Ser Leu Leu Asn Ile Met
1400            1405             1410

Met Leu Val Pro His Lys Arg Tyr Leu Val Ser Ile Lys Val Gln
1415            1420             1425

Ser Ala Gly Met Thr Ser Glu Val Val Glu Asp Ser Thr Ile Thr
1430            1435             1440

Met Ile Asp Arg Pro Pro Pro Pro Pro His Ile Arg Val Asn
1445            1450             1455

Glu Lys Asp Val Leu Ile Ser Lys Ser Ser Ile Asn Phe Thr Val
1460            1465             1470

Asn Cys Ser Trp Phe Ser Asp Thr Asn Gly Ala Val Lys Tyr Phe
1475            1480             1485

Thr Val Val Val Arg Glu Ala Asp Gly Asn Asp Glu Leu Lys Pro
1490            1495             1500

Glu Gln Gln His Pro Leu Pro Ser Tyr Leu Glu Tyr Arg His Asn
1505            1510             1515

Ala Ser Ile Arg Val Tyr Gln Thr Asn Tyr Phe Ala Ser Lys Cys
1520            1525             1530

Ala Glu Asn Pro Asn Ser Asn Ser Lys Ser Phe Asn Ile Lys Leu
1535            1540             1545

Gly Ala Glu Met Glu Ser Leu Gly Gly Lys Cys Asp Pro Thr Gln
1550            1555             1560
```

-continued

```
Gln Lys Phe Cys Asp Gly Pro Leu Lys Pro His Thr Ala Tyr Arg
1565                1570                1575

Ile Ser Ile Arg Ala Phe Thr Gln Leu Phe Asp Glu Asp Leu Lys
1580                1585                1590

Glu Phe Thr Lys Pro Leu Tyr Ser Asp Thr Phe Phe Ser Leu Pro
1595                1600                1605

Ile Thr Thr Glu Ser Glu Pro Leu Phe Gly Ala Ile Glu Gly Val
1610                1615                1620

Ser Ala Gly Leu Phe Leu Ile Gly Met Leu Val Ala Val Val Ala
1625                1630                1635

Leu Leu Ile Cys Arg Gln Lys Val Ser His Gly Arg Glu Arg Pro
1640                1645                1650

Ser Ala Arg Leu Ser Ile Arg Arg Asp Arg Pro Leu Ser Val His
1655                1660                1665

Leu Asn Leu Gly Gln Lys Gly Asn Arg Lys Thr Ser Cys Pro Ile
1670                1675                1680

Lys Ile Asn Gln Phe Glu Gly His Phe Met Lys Leu Gln Ala Asp
1685                1690                1695

Ser Asn Tyr Leu Leu Ser Lys Glu Tyr Glu Glu Leu Lys Asp Val
1700                1705                1710

Gly Arg Asn Gln Ser Cys Asp Ile Ala Leu Leu Pro Glu Asn Arg
1715                1720                1725

Gly Lys Asn Arg Tyr Asn Asn Ile Leu Pro Tyr Asp Ala Thr Arg
1730                1735                1740

Val Lys Leu Ser Asn Val Asp Asp Pro Cys Ser Asp Tyr Ile
1745                1750                1755

Asn Ala Ser Tyr Ile Pro Gly Asn Asn Phe Arg Arg Glu Tyr Ile
1760                1765                1770

Val Thr Gln Gly Pro Leu Pro Gly Thr Lys Asp Asp Phe Trp Lys
1775                1780                1785

Met Val Trp Glu Gln Asn Val His Asn Ile Val Met Val Thr Gln
1790                1795                1800

Cys Val Glu Lys Gly Arg Val Lys Cys Asp His Tyr Trp Pro Ala
1805                1810                1815

Asp Gln Asp Ser Leu Tyr Tyr Gly Asp Leu Ile Leu Gln Met Leu
1820                1825                1830

Ser Glu Ser Val Leu Pro Glu Trp Thr Ile Arg Glu Phe Lys Ile
1835                1840                1845

Cys Gly Glu Glu Gln Leu Asp Ala His Arg Leu Ile Arg His Phe
1850                1855                1860

His Tyr Thr Val Trp Pro Asp His Gly Val Pro Glu Thr Thr Gln
1865                1870                1875

Ser Leu Ile Gln Phe Val Arg Thr Val Arg Asp Tyr Ile Asn Arg
1880                1885                1890

Ser Pro Gly Ala Gly Pro Thr Val Val His Cys Ser Ala Gly Val
1895                1900                1905

Gly Arg Thr Gly Thr Phe Ile Ala Leu Asp Arg Ile Leu Gln Gln
1910                1915                1920

Leu Asp Ser Lys Asp Ser Val Asp Ile Tyr Gly Ala Val His Asp
1925                1930                1935

Leu Arg Leu His Arg Val His Met Val Gln Thr Glu Cys Gln Tyr
1940                1945                1950

Val Tyr Leu His Gln Cys Val Arg Asp Val Leu Arg Ala Arg Lys
```

-continued

```
              1955                1960                1965

Leu Arg Ser Glu Gln Glu Asn Pro Leu Phe Pro Ile Tyr Glu Asn
         1970                1975                1980

Val Asn Pro Glu Tyr His Arg Asp Pro Val Tyr Ser Arg His
         1985                1990                1995

<210> SEQ ID NO 3
<211> LENGTH: 1631
<212> TYPE: PRT
<213> ORGANISM: Homo sapiens

<400> SEQUENCE: 3

Met Leu Ser His Gly Ala Gly Leu Ala Leu Trp Ile Thr Leu Ser Leu
 1               5                  10                  15

Leu Gln Thr Gly Leu Ala Glu Pro Glu Arg Cys Asn Phe Thr Leu Ala
             20                  25                  30

Glu Ser Lys Ala Ser Ser His Ser Val Ser Ile Gln Trp Arg Ile Leu
         35                  40                  45

Gly Ser Pro Cys Asn Phe Ser Leu Ile Tyr Ser Ser Asp Thr Leu Gly
     50                  55                  60

Ala Ala Leu Cys Pro Thr Phe Arg Ile Asp Asn Thr Thr Tyr Gly Cys
 65                  70                  75                  80

Asn Leu Gln Asp Leu Gln Ala Gly Thr Ile Tyr Asn Phe Arg Ile Ile
                 85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Ser Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190

Phe Ser Val Tyr Thr Asn Gly Ser Thr Val Pro Ser Pro Val Lys Asp
        195                 200                 205

Ile Gly Ile Ser Thr Lys Ala Asn Ser Leu Leu Ile Ser Trp Ser His
    210                 215                 220

Gly Ser Gly Asn Val Glu Arg Tyr Arg Leu Met Leu Met Asp Lys Gly
225                 230                 235                 240

Ile Leu Val His Gly Gly Val Val Asp Lys His Ala Thr Ser Tyr Ala
                245                 250                 255

Phe His Gly Leu Thr Pro Gly Tyr Leu Tyr Asn Leu Thr Val Met Thr
            260                 265                 270

Glu Ala Ala Gly Leu Gln Asn Tyr Arg Trp Lys Leu Val Arg Thr Ala
        275                 280                 285

Pro Met Glu Val Ser Asn Leu Lys Val Thr Asn Asp Gly Ser Leu Thr
    290                 295                 300

Ser Leu Lys Val Lys Trp Gln Arg Pro Pro Gly Asn Val Asp Ser Tyr
305                 310                 315                 320

Asn Ile Thr Leu Ser His Lys Gly Thr Ile Lys Glu Ser Arg Val Leu
                325                 330                 335
```

```
Ala Pro Trp Ile Thr Glu Thr His Phe Lys Glu Leu Val Pro Gly Arg
            340                 345                 350

Leu Tyr Gln Val Thr Val Ser Cys Val Ser Gly Glu Leu Ser Ala Gln
    355                 360                 365

Lys Met Ala Val Gly Arg Thr Phe Pro Asp Lys Val Ala Asn Leu Glu
370                 375                 380

Ala Asn Asn Asn Gly Arg Met Arg Ser Leu Val Val Ser Trp Ser Pro
385                 390                 395                 400

Pro Ala Gly Asp Trp Glu Gln Tyr Arg Ile Leu Leu Phe Asn Asp Ser
                405                 410                 415

Val Val Leu Leu Asn Ile Thr Val Gly Lys Glu Thr Gln Tyr Val
            420                 425                 430

Met Asp Asp Thr Gly Leu Val Pro Gly Arg Gln Tyr Glu Val Glu Val
            435                 440                 445

Ile Val Glu Ser Gly Asn Leu Lys Asn Ser Glu Arg Cys Gln Gly Arg
        450                 455                 460

Thr Val Pro Leu Ala Val Leu Gln Leu Arg Val Lys His Ala Asn Glu
465                 470                 475                 480

Thr Ser Leu Ser Ile Met Trp Gln Thr Pro Val Ala Glu Trp Glu Lys
                485                 490                 495

Tyr Ile Ile Ser Leu Ala Asp Arg Asp Leu Leu Ile His Lys Ser
            500                 505                 510

Leu Ser Lys Asp Ala Lys Glu Phe Thr Phe Thr Asp Leu Val Pro Gly
        515                 520                 525

Arg Lys Tyr Met Ala Thr Val Thr Ser Ile Ser Gly Asp Leu Lys Asn
530                 535                 540

Ser Ser Ser Val Lys Gly Arg Thr Val Pro Ala Gln Val Thr Asp Leu
545                 550                 555                 560

His Val Ala Asn Gln Gly Met Thr Ser Ser Leu Phe Thr Asn Trp Thr
                565                 570                 575

Gln Ala Gln Gly Asp Val Glu Phe Tyr Gln Val Leu Leu Ile His Glu
            580                 585                 590

Asn Val Val Ile Lys Asn Glu Ser Ile Ser Ser Glu Thr Ser Arg Tyr
        595                 600                 605

Ser Phe His Ser Leu Lys Ser Gly Ser Leu Tyr Ser Val Val Thr
    610                 615                 620

Thr Val Ser Gly Gly Ile Ser Ser Arg Gln Val Val Glu Gly Arg
625                 630                 635                 640

Thr Val Pro Ser Ser Val Ser Gly Val Thr Val Asn Asn Ser Gly Arg
                645                 650                 655

Asn Asp Tyr Leu Ser Val Ser Trp Leu Leu Ala Pro Gly Asp Val Asp
            660                 665                 670

Asn Tyr Glu Val Thr Leu Ser His Asp Gly Lys Val Val Gln Ser Leu
        675                 680                 685

Val Ile Ala Lys Ser Val Arg Glu Cys Ser Phe Ser Ser Leu Thr Pro
    690                 695                 700

Gly Arg Leu Tyr Thr Val Thr Ile Thr Thr Arg Ser Gly Lys Tyr Glu
705                 710                 715                 720

Asn His Ser Phe Ser Gln Glu Arg Thr Val Pro Asp Lys Val Gln Gly
                725                 730                 735

Val Ser Val Ser Asn Ser Ala Arg Ser Asp Tyr Leu Arg Val Ser Trp
            740                 745                 750

Val His Ala Thr Gly Asp Phe Asp His Tyr Glu Val Thr Ile Lys Asn
```

```
              755                 760                 765
Lys Asn Asn Phe Ile Gln Thr Lys Ser Ile Pro Lys Ser Glu Asn Glu
    770                 775                 780

Cys Val Phe Val Gln Leu Val Pro Gly Arg Leu Tyr Ser Val Thr Val
785                 790                 795                 800

Thr Thr Lys Ser Gly Gln Tyr Glu Ala Asn Glu Gln Gly Asn Gly Arg
                805                 810                 815

Thr Ile Pro Glu Pro Val Lys Asp Leu Thr Leu Arg Asn Arg Ser Thr
            820                 825                 830

Glu Asp Leu His Val Thr Trp Ser Gly Ala Asn Gly Asp Val Asp Gln
        835                 840                 845

Tyr Glu Ile Gln Leu Leu Phe Asn Asp Met Lys Val Phe Pro Pro Phe
    850                 855                 860

His Leu Val Asn Thr Ala Thr Glu Tyr Arg Phe Thr Ser Leu Thr Pro
865                 870                 875                 880

Gly Arg Gln Tyr Lys Ile Leu Val Leu Thr Ile Ser Gly Asp Val Gln
                885                 890                 895

Gln Ser Ala Phe Ile Glu Gly Phe Thr Val Pro Ser Ala Val Lys Asn
            900                 905                 910

Ile His Ile Ser Pro Asn Gly Ala Thr Asp Ser Leu Thr Val Asn Trp
        915                 920                 925

Thr Pro Gly Gly Gly Asp Val Asp Ser Tyr Thr Val Ser Ala Phe Arg
    930                 935                 940

His Ser Gln Lys Val Asp Ser Gln Thr Ile Pro Lys His Val Phe Glu
945                 950                 955                 960

His Thr Phe His Arg Leu Glu Ala Gly Glu Gln Tyr Gln Ile Met Ile
                965                 970                 975

Ala Ser Val Ser Gly Ser Leu Lys Asn Gln Ile Asn Val Gly Arg
            980                 985                 990

Thr Val Pro Ala Ser Val Gln Gly  Val Ile Ala Asp Asn  Ala Tyr Ser
        995                 1000                1005

Ser Tyr  Ser Leu Ile Val Ser  Trp Gln Lys Ala Ala  Gly Val Ala
    1010                1015                1020

Glu Arg  Tyr Asp Ile Leu Leu  Thr Glu Asn Gly  Ile Leu Leu
    1025                1030                1035

Arg Asn  Thr Ser Glu Pro Ala  Thr Thr Lys Gln His  Lys Phe Glu
    1040                1045                1050

Asp Leu  Thr Pro Gly Lys Lys  Tyr Lys Ile Gln Ile  Leu Thr Val
    1055                1060                1065

Ser Gly  Gly Leu Phe Ser Lys  Glu Ala Gln Thr Glu  Gly Arg Thr
    1070                1075                1080

Val Pro  Ala Ala Val Thr Asp  Leu Arg Ile Thr Glu  Asn Ser Thr
    1085                1090                1095

Arg His  Leu Ser Phe Arg Trp  Thr Ala Ser Glu Gly  Glu Leu Ser
    1100                1105                1110

Trp Tyr  Asn Ile Phe Leu Tyr  Asn Pro Asp Gly Asn  Leu Gln Glu
    1115                1120                1125

Arg Ala  Gln Val Asp Pro Leu  Val Gln Ser Phe Ser  Phe Gln Asn
    1130                1135                1140

Leu Leu  Gln Gly Arg Met Tyr  Lys Met Val Ile Val  Thr His Ser
    1145                1150                1155

Gly Glu  Leu Ser Asn Glu Ser  Phe Ile Phe Gly Arg  Thr Val Pro
    1160                1165                1170
```

```
Ala Ser Val Ser His Leu Arg Gly Ser Asn Arg Asn Thr Thr Asp
    1175            1180                1185
Ser Leu Trp Phe Asn Trp Ser Pro Ala Ser Gly Asp Phe Asp Phe
    1190            1195                1200
Tyr Glu Leu Ile Leu Tyr Asn Pro Asn Gly Thr Lys Lys Glu Asn
    1205            1210                1215
Trp Lys Asp Lys Asp Leu Thr Glu Trp Arg Phe Gln Gly Leu Val
    1220            1225                1230
Pro Gly Arg Lys Tyr Val Leu Trp Val Val Thr His Ser Gly Asp
    1235            1240                1245
Leu Ser Asn Lys Val Thr Ala Glu Ser Arg Thr Ala Pro Ser Pro
    1250            1255                1260
Pro Ser Leu Met Ser Phe Ala Asp Ile Ala Asn Thr Ser Leu Ala
    1265            1270                1275
Ile Thr Trp Lys Gly Pro Pro Asp Trp Thr Asp Tyr Asn Asp Phe
    1280            1285                1290
Glu Leu Gln Trp Leu Pro Arg Asp Ala Leu Thr Val Phe Asn Pro
    1295            1300                1305
Tyr Asn Asn Arg Lys Ser Glu Gly Arg Ile Val Tyr Gly Leu Arg
    1310            1315                1320
Pro Gly Arg Ser Tyr Gln Phe Asn Val Lys Thr Val Ser Gly Asp
    1325            1330                1335
Ser Trp Lys Thr Tyr Ser Lys Pro Ile Phe Gly Ser Val Arg Thr
    1340            1345                1350
Lys Pro Asp Lys Ile Gln Asn Leu His Cys Arg Pro Gln Asn Ser
    1355            1360                1365
Thr Ala Ile Ala Cys Ser Trp Ile Pro Pro Asp Ser Asp Phe Asp
    1370            1375                1380
Gly Tyr Ser Ile Glu Cys Arg Lys Met Asp Thr Gln Glu Val Glu
    1385            1390                1395
Phe Ser Arg Lys Leu Glu Lys Glu Lys Ser Leu Leu Asn Ile Met
    1400            1405                1410
Met Leu Val Pro His Lys Arg Tyr Leu Val Ser Ile Lys Val Gln
    1415            1420                1425
Ser Ala Gly Met Thr Ser Glu Val Val Glu Asp Ser Thr Ile Thr
    1430            1435                1440
Met Ile Asp Arg Pro Pro Pro Pro Pro Pro His Ile Arg Val Asn
    1445            1450                1455
Glu Lys Asp Val Leu Ile Ser Lys Ser Ser Ile Asn Phe Thr Val
    1460            1465                1470
Asn Cys Ser Trp Phe Ser Asp Thr Asn Gly Ala Val Lys Tyr Phe
    1475            1480                1485
Thr Val Val Val Arg Glu Ala Asp Gly Asn Asp Glu Leu Lys Pro
    1490            1495                1500
Glu Gln Gln His Pro Leu Pro Ser Tyr Leu Glu Tyr Arg His Asn
    1505            1510                1515
Ala Ser Ile Arg Val Tyr Gln Thr Asn Tyr Phe Ala Ser Lys Cys
    1520            1525                1530
Ala Glu Asn Pro Asn Ser Asn Ser Lys Ser Phe Asn Ile Lys Leu
    1535            1540                1545
Gly Ala Glu Met Glu Ser Leu Gly Gly Lys Cys Asp Pro Thr Gln
    1550            1555                1560
```

```
Gln Lys Phe Cys Asp Gly Pro Leu Lys Pro His Thr Ala Tyr Arg
    1565                1570                1575

Ile Ser Ile Arg Ala Phe Thr Gln Leu Phe Asp Glu Asp Leu Lys
    1580                1585                1590

Glu Phe Thr Lys Pro Leu Tyr Ser Asp Thr Phe Phe Ser Leu Pro
    1595                1600                1605

Ile Thr Thr Glu Ser Glu Pro Leu Phe Gly Ala Ile Glu Arg Gly
    1610                1615                1620

Arg His His His His His His Gly
    1625                1630

<210> SEQ ID NO 4
<211> LENGTH: 1621
<212> TYPE: PRT
<213> ORGANISM: Homo sapiens

<400> SEQUENCE: 4

Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
            20                  25                  30

Glu Ser Lys Ala Ser Ser His Ser Val Ser Ile Gln Trp Arg Ile Leu
        35                  40                  45

Gly Ser Pro Cys Asn Phe Ser Leu Ile Tyr Ser Ser Asp Thr Leu Gly
    50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Arg Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Ser Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190

Phe Ser Val Tyr Thr Asn Gly Ser Thr Val Pro Ser Pro Val Lys Asp
        195                 200                 205

Ile Gly Ile Ser Thr Lys Ala Asn Ser Leu Leu Ile Ser Trp Ser His
    210                 215                 220

Gly Ser Gly Asn Val Glu Arg Tyr Arg Leu Met Leu Met Asp Lys Gly
225                 230                 235                 240

Ile Leu Val His Gly Gly Val Val Asp Lys His Ala Thr Ser Tyr Ala
                245                 250                 255

Phe His Gly Leu Thr Pro Gly Tyr Leu Tyr Asn Leu Thr Val Met Thr
            260                 265                 270

Glu Ala Ala Gly Leu Gln Asn Tyr Arg Trp Lys Leu Val Arg Thr Ala
        275                 280                 285

Pro Met Glu Val Ser Asn Leu Lys Val Thr Asn Asp Gly Ser Leu Thr
    290                 295                 300
```

```
Ser Leu Lys Val Lys Trp Gln Arg Pro Pro Gly Asn Val Asp Ser Tyr
305                 310                 315                 320

Asn Ile Thr Leu Ser His Lys Gly Thr Ile Lys Glu Ser Arg Val Leu
            325                 330                 335

Ala Pro Trp Ile Thr Glu Thr His Phe Lys Glu Leu Val Pro Gly Arg
            340                 345                 350

Leu Tyr Gln Val Thr Val Ser Cys Val Ser Gly Glu Leu Ser Ala Gln
            355                 360                 365

Lys Met Ala Val Gly Arg Thr Phe Pro Asp Lys Val Ala Asn Leu Glu
            370                 375                 380

Ala Asn Asn Asn Gly Arg Met Arg Ser Leu Val Val Ser Trp Ser Pro
385                 390                 395                 400

Pro Ala Gly Asp Trp Glu Gln Tyr Arg Ile Leu Leu Phe Asn Asp Ser
                405                 410                 415

Val Val Leu Leu Asn Ile Thr Val Gly Lys Glu Glu Thr Gln Tyr Val
            420                 425                 430

Met Asp Asp Thr Gly Leu Val Pro Gly Arg Gln Tyr Glu Val Glu Val
            435                 440                 445

Ile Val Glu Ser Gly Asn Leu Lys Asn Ser Glu Arg Cys Gln Gly Arg
450                 455                 460

Thr Val Pro Leu Ala Val Leu Gln Leu Arg Val Lys His Ala Asn Glu
465                 470                 475                 480

Thr Ser Leu Ser Ile Met Trp Gln Thr Pro Val Ala Glu Trp Glu Lys
                485                 490                 495

Tyr Ile Ile Ser Leu Ala Asp Arg Asp Leu Leu Leu Ile His Lys Ser
                500                 505                 510

Leu Ser Lys Asp Ala Lys Glu Phe Thr Phe Thr Asp Leu Val Pro Gly
            515                 520                 525

Arg Lys Tyr Met Ala Thr Val Thr Ser Ile Ser Gly Asp Leu Lys Asn
            530                 535                 540

Ser Ser Ser Val Lys Gly Arg Thr Val Pro Ala Gln Val Thr Asp Leu
545                 550                 555                 560

His Val Ala Asn Gln Gly Met Thr Ser Ser Leu Phe Thr Asn Trp Thr
                565                 570                 575

Gln Ala Gln Gly Asp Val Glu Phe Tyr Gln Val Leu Leu Ile His Glu
            580                 585                 590

Asn Val Val Ile Lys Asn Glu Ser Ile Ser Ser Glu Thr Ser Arg Tyr
            595                 600                 605

Ser Phe His Ser Leu Lys Ser Gly Ser Leu Tyr Ser Val Val Val Thr
            610                 615                 620

Thr Val Ser Gly Gly Ile Ser Ser Arg Gln Val Val Glu Gly Arg
625                 630                 635                 640

Thr Val Pro Ser Val Ser Gly Val Thr Val Asn Asn Ser Gly Arg
                645                 650                 655

Asn Asp Tyr Leu Ser Val Ser Trp Leu Leu Ala Pro Gly Asp Val Asp
            660                 665                 670

Asn Tyr Glu Val Thr Leu Ser His Asp Gly Lys Val Val Gln Ser Leu
            675                 680                 685

Val Ile Ala Lys Ser Val Arg Glu Cys Ser Phe Ser Ser Leu Thr Pro
            690                 695                 700

Gly Arg Leu Tyr Thr Val Thr Ile Thr Thr Arg Ser Gly Lys Tyr Glu
705                 710                 715                 720
```

```
Asn His Ser Phe Ser Gln Glu Arg Thr Val Pro Asp Lys Val Gln Gly
                725                 730                 735
Val Ser Val Ser Asn Ser Ala Arg Ser Asp Tyr Leu Arg Val Ser Trp
            740                 745                 750
Val His Ala Thr Gly Asp Phe Asp His Tyr Glu Val Thr Ile Lys Asn
        755                 760                 765
Lys Asn Asn Phe Ile Gln Thr Lys Ser Ile Pro Lys Ser Glu Asn Glu
    770                 775                 780
Cys Val Phe Val Gln Leu Val Pro Gly Arg Leu Tyr Ser Val Thr Val
785                 790                 795                 800
Thr Thr Lys Ser Gly Gln Tyr Glu Ala Asn Glu Gln Gly Asn Gly Arg
                805                 810                 815
Thr Ile Pro Glu Pro Val Lys Asp Leu Thr Leu Arg Asn Arg Ser Thr
            820                 825                 830
Glu Asp Leu His Val Thr Trp Ser Gly Ala Asn Gly Asp Val Asp Gln
        835                 840                 845
Tyr Glu Ile Gln Leu Leu Phe Asn Asp Met Lys Val Phe Pro Pro Phe
    850                 855                 860
His Leu Val Asn Thr Ala Thr Glu Tyr Arg Phe Thr Ser Leu Thr Pro
865                 870                 875                 880
Gly Arg Gln Tyr Lys Ile Leu Val Leu Thr Ile Ser Gly Asp Val Gln
                885                 890                 895
Gln Ser Ala Phe Ile Glu Gly Phe Thr Val Pro Ser Ala Val Lys Asn
            900                 905                 910
Ile His Ile Ser Pro Asn Gly Ala Thr Asp Ser Leu Thr Val Asn Trp
        915                 920                 925
Thr Pro Gly Gly Gly Asp Val Asp Ser Tyr Thr Val Ser Ala Phe Arg
    930                 935                 940
His Ser Gln Lys Val Asp Ser Gln Thr Ile Pro Lys His Val Phe Glu
945                 950                 955                 960
His Thr Phe His Arg Leu Glu Ala Gly Glu Gln Tyr Gln Ile Met Ile
                965                 970                 975
Ala Ser Val Ser Gly Ser Leu Lys Asn Gln Ile Asn Val Val Gly Arg
            980                 985                 990
Thr Val Pro Ala Ser Val Gln Gly Val Ile Ala Asp Asn Ala Tyr Ser
        995                 1000                1005
Ser Tyr Ser Leu Ile Val Ser Trp Gln Lys Ala Ala Gly Val Ala
    1010                1015                1020
Glu Arg Tyr Asp Ile Leu Leu Leu Thr Glu Asn Gly Ile Leu Leu
    1025                1030                1035
Arg Asn Thr Ser Glu Pro Ala Thr Thr Lys Gln His Lys Phe Glu
    1040                1045                1050
Asp Leu Thr Pro Gly Lys Lys Tyr Lys Ile Gln Ile Leu Thr Val
    1055                1060                1065
Ser Gly Gly Leu Phe Ser Lys Glu Ala Gln Thr Glu Gly Arg Thr
    1070                1075                1080
Val Pro Ala Ala Val Thr Asp Leu Arg Ile Thr Glu Asn Ser Thr
    1085                1090                1095
Arg His Leu Ser Phe Arg Trp Thr Ala Ser Glu Gly Glu Leu Ser
    1100                1105                1110
Trp Tyr Asn Ile Phe Leu Tyr Asn Pro Asp Gly Asn Leu Gln Glu
    1115                1120                1125
Arg Ala Gln Val Asp Pro Leu Val Gln Ser Phe Ser Phe Gln Asn
```

-continued

|      |      |      |      | 1130 |      |      |      |      | 1135 |      |      |      |      | 1140 |
|------|------|------|------|------|------|------|------|------|------|------|------|------|------|------|

Leu Leu Gln Gly Arg Met Tyr Lys Met Val Ile Val Thr His Ser
    1145            1150                1155

Gly Glu Leu Ser Asn Glu Ser Phe Ile Phe Gly Arg Thr Val Pro
    1160            1165                1170

Ala Ser Val Ser His Leu Arg Gly Ser Asn Arg Asn Thr Thr Asp
    1175            1180                1185

Ser Leu Trp Phe Asn Trp Ser Pro Ala Ser Gly Asp Phe Asp Phe
    1190            1195                1200

Tyr Glu Leu Ile Leu Tyr Asn Pro Asn Gly Thr Lys Lys Glu Asn
    1205            1210                1215

Trp Lys Asp Lys Asp Leu Thr Glu Trp Arg Phe Gln Gly Leu Val
    1220            1225                1230

Pro Gly Arg Lys Tyr Val Leu Trp Val Val Thr His Ser Gly Asp
    1235            1240                1245

Leu Ser Asn Lys Val Thr Ala Glu Ser Arg Thr Ala Pro Ser Pro
    1250            1255                1260

Pro Ser Leu Met Ser Phe Ala Asp Ile Ala Asn Thr Ser Leu Ala
    1265            1270                1275

Ile Thr Trp Lys Gly Pro Pro Asp Trp Thr Asp Tyr Asn Asp Phe
    1280            1285                1290

Glu Leu Gln Trp Leu Pro Arg Asp Ala Leu Thr Val Phe Asn Pro
    1295            1300                1305

Tyr Asn Asn Arg Lys Ser Glu Gly Arg Ile Val Tyr Gly Leu Arg
    1310            1315                1320

Pro Gly Arg Ser Tyr Gln Phe Asn Val Lys Thr Val Ser Gly Asp
    1325            1330                1335

Ser Trp Lys Thr Tyr Ser Lys Pro Ile Phe Gly Ser Val Arg Thr
    1340            1345                1350

Lys Pro Asp Lys Ile Gln Asn Leu His Cys Arg Pro Gln Asn Ser
    1355            1360                1365

Thr Ala Ile Ala Cys Ser Trp Ile Pro Pro Asp Ser Asp Phe Asp
    1370            1375                1380

Gly Tyr Ser Ile Glu Cys Arg Lys Met Asp Thr Gln Glu Val Glu
    1385            1390                1395

Phe Ser Arg Lys Leu Glu Lys Glu Lys Ser Leu Leu Asn Ile Met
    1400            1405                1410

Met Leu Val Pro His Lys Arg Tyr Leu Val Ser Ile Lys Val Gln
    1415            1420                1425

Ser Ala Gly Met Thr Ser Glu Val Val Glu Asp Ser Thr Ile Thr
    1430            1435                1440

Met Ile Asp Arg Pro Pro Pro Pro Pro His Ile Arg Val Asn
    1445            1450                1455

Glu Lys Asp Val Leu Ile Ser Lys Ser Ser Ile Asn Phe Thr Val
    1460            1465                1470

Asn Cys Ser Trp Phe Ser Asp Thr Asn Gly Ala Val Lys Tyr Phe
    1475            1480                1485

Thr Val Val Val Arg Glu Ala Asp Gly Asn Asp Glu Leu Lys Pro
    1490            1495                1500

Glu Gln Gln His Pro Leu Pro Ser Tyr Leu Glu Tyr Arg His Asn
    1505            1510                1515

Ala Ser Ile Arg Val Tyr Gln Thr Asn Tyr Phe Ala Ser Lys Cys
    1520            1525                1530

```
Ala Glu Asn Pro Asn Ser Asn  Ser Lys Ser Phe Asn  Ile Lys Leu
    1535             1540                  1545

Gly Ala Glu Met Glu Ser Leu  Gly Gly Lys Cys Asp  Pro Thr Gln
1550             1555                  1560

Gln Lys Phe Cys Asp Gly Pro  Leu Lys Pro His Thr  Ala Tyr Arg
    1565             1570                  1575

Ile Ser Ile Arg Ala Phe Thr  Gln Leu Phe Asp Glu  Asp Leu Lys
    1580             1585                  1590

Glu Phe Thr Lys Pro Leu Tyr  Ser Asp Thr Phe Phe  Ser Leu Pro
    1595             1600                  1605

Ile Thr Thr Glu Ser Glu Pro  Leu Phe Gly Ala Ile  Glu
    1610             1615                  1620

<210> SEQ ID NO 5
<211> LENGTH: 6199
<212> TYPE: DNA
<213> ORGANISM: Mus musculus

<400> SEQUENCE: 5
```

| | | | | |
|---|---|---|---|---|
| ggcacgaggg | cggctgccac | ggcccttgag | catcgccagc | cccgagggta gcgcgctgcg | 60 |
| cccgcccgca | gggcgcgctg | agcgctcaac | aagtggtacc | agaagtgcc ctggctggcc | 120 |
| tcccagcgag | atgctgaggc | atggagccct | aacggccttg | tggataacac tgagcgtcgt | 180 |
| gcagactgga | gtggcagagc | aagtgaaatg | taacttcaca | ctgttggagt ccagggtctc | 240 |
| tagcttgtca | gcgtctatcc | agtggaggac | tttcgcgtca | ccctgtaact ttagcctcat | 300 |
| ctacagcagt | gatacctcgg | ggcccatgtg | gtgccatcct | attcggatag acaactttac | 360 |
| ctacggatgt | aaccccaagg | atttacaagc | agggaccgtc | tataacttca ggattgtttc | 420 |
| tctggatgga | gaagagagca | ctctggtctt | acagacagat | ccgttgcctc ctgccaggtt | 480 |
| tgaagtcaat | cgggagaaaa | cagcatcaac | caccctgcag | gtccggtgga ctccctcttc | 540 |
| tggaaaagtc | tcctggtatg | aggtgcaatt | atttgatcat | aacaatcaaa agatacaaga | 600 |
| agtccaagtt | caagaaagta | ccacctggag | ccaatatact | tttctgaacc tcactgaggg | 660 |
| taacagttac | aaagttgcca | tcacagctgt | ttcgggagaa | aagcgctcct ttccggtgta | 720 |
| tatcaatggc | tctacagtac | catctccagt | gaaagatctt | ggcatttccc ccaatcctaa | 780 |
| ttctctccta | atttcctggt | ctcgtggttc | tgggaatgtg | aacaataca ggctggtgct | 840 |
| aatggataaa | ggggccatcg | ttcaagacac | aaacgtggac | aggcgtgata cttcttatgc | 900 |
| ttttcacgag | ctgaccccctg | gccacctcta | caacctcact | attgtcacca tggcctcggg | 960 |
| actgcaaaac | tccaggtgga | aactggtgag | gaccgctccc | atggaagtct caaatctgaa | 1020 |
| ggtgacaaat | gacgggaggt | tgacctctct | aaatgtgaag | tggcagaaac ccctggggaa | 1080 |
| tgtagattcc | tacagcatta | ccctgtctca | ccaagggacc | atcaaagaat ccaaaacatt | 1140 |
| agcacctcct | gttactgaaa | ctcaatttaa | ggacttagtc | cctggacggc tttaccaagt | 1200 |
| gaccatcagc | tgcatctctg | gtgagctctc | tgctgagaag | tcagcagcgg ggagaacagt | 1260 |
| tccagaaaaa | gtgaggaatc | tggtttccta | caacgagatt | tggatgaagt cctttacagt | 1320 |
| gaactggacg | cccccctgctg | gagattggga | gcattatcgt | atcgtgctct tcaatgaatc | 1380 |
| cttggtcttg | ctcaacacca | cagtgggaaa | ggaagaaacg | cactatgcct ggatggcttt | 1440 |
| ggagctcata | ccaggaagac | agtatgagat | agaagtcatt | gttgagagcg aaatctgcg | 1500 |
| gaattccgag | cgctgtcaag | gcaggacagt | acccctggct | gtcctccagc ttcgcgtcaa | 1560 |

```
acacgctaac gaaacttcac tgggcatcac gtggcgggcc cctctaggcg aatgggagaa    1620
atacatcatt tcgttgatgg acagagagct cttggtcatc cacaagtcac tctccaaaga    1680
tgccaaagaa ttcactttta cagacctgat gcctggacgg aattacaagg ctactgtcac    1740
tagcatgagt ggagatttaa aacagtcatc ttcaatcaaa ggaagaacag tgcctgccca    1800
ggtgactgac ctgcacgtca acaaccaagg gatgaccagt agtctgttca ctaactggac    1860
aaaggcactg ggagatgtag agttctacca agttttactg atccatgaaa atgtggttgt    1920
caagaacgag agtgtttcca gtgataccag cagatacagc ttccgcgccc tgaaacccgg    1980
cagcctctac tccgtggtgg tgaccacggt gagtggaggg atctcctccc ggcaggtggt    2040
ggcggaagga agaacagtcc cgtccagcgt gagtggggtg acagtcaaca attctggccg    2100
gaatgactac ctcagcgttt cctggctgcc ggcgcctgga gaagtggatc actacgtggt    2160
gagcctctcc cacgagggca aggtggatca gttcctcatc atcgccaaat ctgtcagcga    2220
gtgttccttc agctccctca ccccgggccg cctctacaac gtcactgtaa ccaccaagag    2280
cggcaattat gcaagccact ccttcaccga ggaacggaca gtgccagaca aggtccaggg    2340
aatcagtgtt agcaactctg ccagaagcga ctacttaaag gtgtcctggg tgcatgccac    2400
tggagacttt gaccactatg aagtcaccat caaaaacaga gaaagcttca ttcaaaccaa    2460
aaccatcccc aagtcagaaa atgagtgtga atttattgag ctggttcctg acgcctgta    2520 cagcgtcact gtcagtacaa agagtggaca atatgaagcc agtgaacagg gacagggag    2580 aacgatccca gagcctgtga aggatctcac ccttctcaac aggagtacgg aggatctcca    2640
tgtgacttgg tcaagagcca atggggatgt tgatcagtac gaggtccagc tgctcttcaa    2700
cgacatgaaa gtcttccctc atattcacct tgtgaacaca gcaactgagt ataagttcac    2760
ggcgctcacg ccggggcgcc attacaaaat cctcgtcctg accatcagtg gcgatgtcca    2820
gcagtcagcc ttcattgaag gcctcccagt tcccagcact gtcaaaaaca ttcacatttc    2880
tgccaatgga gccacggata ggctgatggt aacctggagc cctggtggcg gggatgtgga    2940
ctcctatgtg gtgtctgcat tcagacagga cgagaaggtt gactctcaga ccattcccaa    3000
gcatgcctcg gagcacacgt tccacaggct ggaggccgga gccaagtaca ggatcgccat    3060
tgtttctgtc agtgggtccc tgagaaacca gatagatgcg ctcggacaga cagtcccagc    3120
gtctgtccag ggagtcgtcg cagccaatgc atacagcagt aattccttaa cagtaagttg    3180
gcagaaagcc cttggtgtgg cagaaagata cgatatcctg cttctaaacg agaatgggct    3240 tctttgagc aacgtgtcag agccagctac ggcaagacag cacaaatttg aagatctaac    3300
gccaggcaag aaatacaaga tgcagatcct gactgtcagc ggaggcctct tcagtaaaga    3360
atctcaggct gaaggccgaa cagtcccagc agctgtcacc aatctgagga tcacagagaa    3420
ctccagtaga tacctgtcct tcggctggac cgcctcggag ggtgaactca gctggtacaa    3480
catcttcctc tacaacccag acaggactct tcaggagcga gctcaagttg acccgctagt    3540
ccagagcttc tctttccaga acttgctaca aggcagaatg tacaagatgg tgattgtcac    3600
tcacagtggg gagctgtcca atgagtcatt tatattcggc agaacagttc ctgctgccgt    3660
gaaccatctc aaaggctccc atcggaacac gacagacagc ctgtggttca gctggagccc    3720
agcctccggg gactttgact tctatgagct gattctttac aatcccaacg gcacgaagaa    3780
ggagaactgg aaagaaaagg acgtgacaga gtggcgtttc caaggtcttg ttcctggaag    3840
gaaatacacc ctgtatgtgg tgactcacag tgggacctc agcaataaag tcacagggga    3900
gggcagaaca gccccaagtc ctccgagtct tttgtcattc gctgatgttg caaacacctc    3960
```

```
cttggctatc acctggaagg gaccoccaga ctggacagat tacaatgact ttgagctgca    4020
gtggttccct ggagatgcac ttaccatctt caaccoctac agcagcagaa agtcagaagg    4080
acgcattgtg tacgggcttc acccagggag gtcctatcaa ttcagtgtca agactgtgag    4140
cggggactcc tggaaaacct acagcaaacc aatttctggg tctgtgagga caaagccaga    4200
caagatacaa aacctgcatt gccgccccca gaactccacg gccattgcct gctcttggat    4260
acctcctgac tccgactttg atggctacag cattgagtgc cgaaaaatgg atacccaaga    4320
aatcgagttt tccagaaagc tggagaaaga aaaatcactg ctcaacatca tgatgttagt    4380
acctcataag aggtacctgg tgtccatcaa ggtgcagtcg gccggcatga ccagtgaggt    4440
ggttgaagat agcaccatca ccatgataga ccgcccgcct caaccgcctc cacacatccg    4500
tgtgaatgaa aaggatgtgc taatcagcaa atcttccatc aactttactg tcaactgcag    4560
ctggttcagc gacaccaacg gagcggttaa atactttgct gtggtggtga gagaggccga    4620
cagcatggat gagttgaagc cagaacagca gcaccctctc ccttcctacc tggagtacag    4680
acacaacgcc tccatccgag tctaccagac caattatttt gccagcaaat gtgctgaaag    4740
tcccgacagc agttctaaaa gtttcaacat taagcttgga gcagagatgg acagcctcgg    4800
tggcaaatgt gatcccagtc agcagaaatt ctgtgatgga ccgctgaagc cacacaccgc    4860
ctacagaatc agcatccggg cttttacaca gctatttgac gaggacttga aagagttcac    4920
caaacctctc tactcggata cgttcttctc tatgcccatc accacagagt cagagccctt    4980
gtttggagtt attgaaggtg tgagtgctgg cctgtttcta attggcatgc tggtggccct    5040
tgttgccttc ttcatctgca gacagaaagc tagccacagc agggaaaggc catctgcccg    5100
gctcagcatt cgtagggacc ggcctttgtc tgtccatctg aatctgggcc agaaaggcaa    5160
ccggaaaact tcttgcccca taaagatcaa tcagtttgaa gggcatttca tgaagctgca    5220
ggcagactcc aactaccttc tatccaagga atatgaggac ttaaaagacg tgggtagaag    5280
ccagtcatgt gacattgccc tcttgcctga gaatcgaggg aaaaatcgat acaacaacat    5340
attgccttat gatgcctcaa gagtgaagct ctcgaatgtc gatgacgacc cttgctctga    5400
ctacatcaac gccagctaca tcccocggtaa caacttcaga cgagaataca tcgccactca    5460
gggaccgctt ccaggcacca aggatgactt ctggaagatg gcgtgggagc agaacgttca    5520
caacatcgtc atggtgaccc agtgtgttga aaagggccga gtgaagtgtg accattactg    5580
gccagcagac caggaccccc tctactacgg tgatctcatc ctacagatgg tctcggagtc    5640
cgtgctcccc gagtggacca tcagggagtt taaggatatgc agtgaagaac agttggatgc    5700
acacagactc atccgtcact ttcactacac ggtgtggcca gaccatgggg tcccagagac    5760
cacccagtcc ctgatccaat tgtgaggac agtcagggac tacatcaaca gaagcccgg    5820 ggctgggccc accgtagtgc actgcagcgc tggtgtgggc agaacaggga cgttcgttgc    5880
cctggaccgg atcctccagc agttggactc taaggactcc gtggacattt atggggcagt    5940
gcatgaccta agactccaca gggttcacat ggtccagacc gagtgtcaat atgtgtatct    6000
gcatcagtgt gtaagagacg tcctcagagc aaagaaactg cggaacgagc aagagaaccc    6060
cctgtttccg atttatgaga atgtgaatcc agagtatcac agagatgcaa tctactcgag    6120
acattaagaa ttcacctgaa gatccoctgg ataaaagcgt ttcactgtgt gacttttaaaa    6180 aaaaaaaaaa aaaaaaaaa                                                 6199
```

<210> SEQ ID NO 6

<211> LENGTH: 1998
<212> TYPE: PRT
<213> ORGANISM: Mus musculus

<400> SEQUENCE: 6

```
Met Leu Arg His Gly Ala Leu Thr Ala Leu Trp Ile Thr Leu Ser Val
1               5                   10                  15

Val Gln Thr Gly Val Ala Glu Gln Val Lys Cys Asn Phe Thr Leu Leu
            20                  25                  30

Glu Ser Arg Val Ser Ser Leu Ala Ser Ile Gln Trp Arg Thr Phe
        35                  40                  45

Ala Ser Pro Cys Asn Phe Ser Leu Ile Tyr Ser Ser Asp Thr Ser Gly
    50                  55                  60

Pro Met Trp Cys His Pro Ile Arg Ile Asp Asn Phe Thr Tyr Gly Cys
65              70                  75                  80

Asn Pro Lys Asp Leu Gln Ala Gly Thr Val Tyr Asn Phe Arg Ile Val
                85                  90                  95

Ser Leu Asp Gly Glu Glu Ser Thr Leu Val Leu Gln Thr Asp Pro Leu
            100                 105                 110

Pro Pro Ala Arg Phe Glu Val Asn Arg Glu Lys Thr Ala Ser Thr Thr
        115                 120                 125

Leu Gln Val Arg Trp Thr Pro Ser Ser Gly Lys Val Ser Trp Tyr Glu
    130                 135                 140

Val Gln Leu Phe Asp His Asn Asn Gln Lys Ile Gln Glu Val Gln Val
145                 150                 155                 160

Gln Glu Ser Thr Thr Trp Ser Gln Tyr Thr Phe Leu Asn Leu Thr Glu
                165                 170                 175

Gly Asn Ser Tyr Lys Val Ala Ile Thr Ala Val Ser Gly Glu Lys Arg
            180                 185                 190

Ser Phe Pro Val Tyr Ile Asn Gly Ser Thr Val Pro Ser Pro Val Lys
        195                 200                 205

Asp Leu Gly Ile Ser Pro Asn Pro Asn Ser Leu Leu Ile Ser Trp Ser
    210                 215                 220

Arg Gly Ser Gly Asn Val Glu Gln Tyr Arg Leu Val Leu Met Asp Lys
225                 230                 235                 240

Gly Ala Ile Val Gln Asp Thr Asn Val Asp Arg Arg Asp Thr Ser Tyr
                245                 250                 255

Ala Phe His Glu Leu Thr Pro Gly His Leu Tyr Asn Leu Thr Ile Val
            260                 265                 270

Thr Met Ala Ser Gly Leu Gln Asn Ser Arg Trp Lys Leu Val Arg Thr
        275                 280                 285

Ala Pro Met Glu Val Ser Asn Leu Lys Val Thr Asn Asp Gly Arg Leu
    290                 295                 300

Thr Ser Leu Asn Val Lys Trp Gln Lys Pro Pro Gly Asp Val Asp Ser
305                 310                 315                 320

Tyr Ser Ile Thr Leu Ser His Gln Gly Thr Ile Lys Glu Ser Lys Thr
                325                 330                 335

Leu Ala Pro Pro Val Thr Glu Thr Gln Phe Lys Asp Leu Val Pro Gly
            340                 345                 350

Arg Leu Tyr Gln Val Thr Ile Ser Cys Ile Ser Gly Glu Leu Ser Ala
        355                 360                 365

Glu Lys Ser Ala Ala Gly Arg Thr Val Pro Glu Lys Val Arg Asn Leu
    370                 375                 380

Val Ser Tyr Asn Glu Ile Trp Met Lys Ser Phe Thr Val Asn Trp Thr
```

-continued

```
            385                 390                 395                 400
Pro Pro Ala Gly Asp Trp Glu His Tyr Arg Ile Val Leu Phe Asn Glu
                    405                 410                 415
Ser Leu Val Leu Leu Asn Thr Thr Val Gly Lys Glu Thr His Tyr
                420                 425                 430
Ala Leu Asp Gly Leu Glu Leu Ile Pro Gly Arg Gln Tyr Glu Ile Glu
            435                 440                 445
Val Ile Val Glu Ser Gly Asn Leu Arg Asn Ser Glu Arg Cys Gln Gly
            450                 455                 460
Arg Thr Val Pro Leu Ala Val Leu Gln Leu Arg Val Lys His Ala Asn
465                 470                 475                 480
Glu Thr Ser Leu Gly Ile Thr Trp Arg Ala Pro Leu Gly Glu Trp Glu
                485                 490                 495
Lys Tyr Ile Ile Ser Leu Met Asp Arg Glu Leu Leu Val Ile His Lys
                500                 505                 510
Ser Leu Ser Lys Asp Ala Lys Glu Phe Thr Phe Thr Asp Leu Met Pro
            515                 520                 525
Gly Arg Asn Tyr Lys Ala Thr Val Thr Ser Met Ser Gly Asp Leu Lys
            530                 535                 540
Gln Ser Ser Ser Ile Lys Gly Arg Thr Val Pro Ala Gln Val Thr Asp
545                 550                 555                 560
Leu His Val Asn Asn Gln Gly Met Thr Ser Ser Leu Phe Thr Asn Trp
                565                 570                 575
Thr Lys Ala Leu Gly Asp Val Glu Phe Tyr Gln Val Leu Leu Ile His
                580                 585                 590
Glu Asn Val Val Lys Asn Glu Ser Val Ser Ser Asp Thr Ser Arg
                595                 600                 605
Tyr Ser Phe Arg Ala Leu Lys Pro Gly Ser Leu Tyr Ser Val Val Val
            610                 615                 620
Thr Thr Val Ser Gly Gly Ile Ser Ser Arg Gln Val Val Ala Glu Gly
625                 630                 635                 640
Arg Thr Val Pro Ser Ser Val Ser Gly Val Thr Val Asn Asn Ser Gly
                645                 650                 655
Arg Asn Asp Tyr Leu Ser Val Ser Trp Leu Pro Ala Pro Gly Glu Val
                660                 665                 670
Asp His Tyr Val Val Ser Leu Ser His Glu Gly Lys Val Asp Gln Phe
            675                 680                 685
Leu Ile Ile Ala Lys Ser Val Ser Glu Cys Ser Phe Ser Ser Leu Thr
            690                 695                 700
Pro Gly Arg Leu Tyr Asn Val Thr Val Thr Thr Lys Ser Gly Asn Tyr
705                 710                 715                 720
Ala Ser His Ser Phe Thr Glu Glu Arg Thr Val Pro Asp Lys Val Gln
                725                 730                 735
Gly Ile Ser Val Ser Asn Ser Ala Arg Ser Asp Tyr Leu Lys Val Ser
                740                 745                 750
Trp Val His Ala Thr Gly Asp Phe Asp His Tyr Glu Val Thr Ile Lys
                755                 760                 765
Asn Arg Glu Ser Phe Ile Gln Thr Lys Thr Ile Pro Lys Ser Glu Asn
                770                 775                 780
Glu Cys Glu Phe Ile Glu Leu Val Pro Gly Arg Leu Tyr Ser Val Thr
785                 790                 795                 800
Val Ser Thr Lys Ser Gly Gln Tyr Glu Ala Ser Glu Gln Gly Thr Gly
                805                 810                 815
```

```
Arg Thr Ile Pro Glu Pro Val Lys Asp Leu Thr Leu Leu Asn Arg Ser
            820                 825                 830

Thr Glu Asp Leu His Val Thr Trp Ser Arg Ala Asn Gly Asp Val Asp
        835                 840                 845

Gln Tyr Glu Val Gln Leu Leu Phe Asn Asp Met Lys Val Phe Pro His
    850                 855                 860

Ile His Leu Val Asn Thr Ala Thr Glu Tyr Lys Phe Thr Ala Leu Thr
865                 870                 875                 880

Pro Gly Arg His Tyr Lys Ile Leu Val Leu Thr Ile Ser Gly Asp Val
                885                 890                 895

Gln Gln Ser Ala Phe Ile Glu Gly Leu Pro Val Pro Ser Thr Val Lys
        900                 905                 910

Asn Ile His Ile Ser Ala Asn Gly Ala Thr Asp Arg Leu Met Val Thr
            915                 920                 925

Trp Ser Pro Gly Gly Gly Asp Val Asp Ser Tyr Val Val Ser Ala Phe
    930                 935                 940

Arg Gln Asp Glu Lys Val Asp Ser Gln Thr Ile Pro Lys His Ala Ser
945                 950                 955                 960

Glu His Thr Phe His Arg Leu Glu Ala Gly Ala Lys Tyr Arg Ile Ala
                965                 970                 975

Ile Val Ser Val Ser Gly Ser Leu Arg Asn Gln Ile Asp Ala Leu Gly
            980                 985                 990

Gln Thr Val Pro Ala Ser Val Gln Gly Val Val Ala Ala Asn Ala Tyr
        995                 1000                1005

Ser Ser Asn Ser Leu Thr Val Ser Trp Gln Lys Ala Leu Gly Val
    1010                1015                1020

Ala Glu Arg Tyr Asp Ile Leu Leu Leu Asn Glu Asn Gly Leu Leu
    1025                1030                1035

Leu Ser Asn Val Ser Glu Pro Ala Thr Ala Arg Gln His Lys Phe
    1040                1045                1050

Glu Asp Leu Thr Pro Gly Lys Lys Tyr Lys Met Gln Ile Leu Thr
    1055                1060                1065

Val Ser Gly Gly Leu Phe Ser Lys Glu Ser Gln Ala Glu Gly Arg
    1070                1075                1080

Thr Val Pro Ala Ala Val Thr Asn Leu Arg Ile Thr Glu Asn Ser
    1085                1090                1095

Ser Arg Tyr Leu Ser Phe Gly Trp Thr Ala Ser Glu Gly Glu Leu
    1100                1105                1110

Ser Trp Tyr Asn Ile Phe Leu Tyr Asn Pro Asp Arg Thr Leu Gln
    1115                1120                1125

Glu Arg Ala Gln Val Asp Pro Leu Val Gln Ser Phe Ser Phe Gln
    1130                1135                1140

Asn Leu Leu Gln Gly Arg Met Tyr Lys Met Val Ile Val Thr His
    1145                1150                1155

Ser Gly Glu Leu Ser Asn Glu Ser Phe Ile Phe Gly Arg Thr Val
    1160                1165                1170

Pro Ala Ala Val Asn His Leu Lys Gly Ser His Arg Asn Thr Thr
    1175                1180                1185

Asp Ser Leu Trp Phe Ser Trp Ser Pro Ala Ser Gly Asp Phe Asp
    1190                1195                1200

Phe Tyr Glu Leu Ile Leu Tyr Asn Pro Asn Gly Thr Lys Lys Glu
    1205                1210                1215
```

| | | | | | | | | | | | |
|---|---|---|---|---|---|---|---|---|---|---|---|
|Asn|Trp|Lys|Glu|Lys|Asp|Val|Thr|Glu|Trp|Arg|Phe|Gln|Gly|Leu|
| |1220| | | |1225| | | |1230| | | | | |

Val Pro Gly Arg Lys Tyr Thr Leu Tyr Val Val Thr His Ser Gly
    1235             1240            1245

Asp Leu Ser Asn Lys Val Thr Gly Glu Gly Arg Thr Ala Pro Ser
    1250            1255            1260

Pro Pro Ser Leu Leu Ser Phe Ala Asp Val Ala Asn Thr Ser Leu
    1265            1270            1275

Ala Ile Thr Trp Lys Gly Pro Pro Asp Trp Thr Asp Tyr Asn Asp
    1280            1285            1290

Phe Glu Leu Gln Trp Phe Pro Gly Asp Ala Leu Thr Ile Phe Asn
    1295            1300            1305

Pro Tyr Ser Ser Arg Lys Ser Glu Gly Arg Ile Val Tyr Gly Leu
    1310            1315            1320

His Pro Gly Arg Ser Tyr Gln Phe Ser Val Lys Thr Val Ser Gly
    1325            1330            1335

Asp Ser Trp Lys Thr Tyr Ser Lys Pro Ile Ser Gly Ser Val Arg
    1340            1345            1350

Thr Lys Pro Asp Lys Ile Gln Asn Leu His Cys Arg Pro Gln Asn
    1355            1360            1365

Ser Thr Ala Ile Ala Cys Ser Trp Ile Pro Pro Asp Ser Asp Phe
    1370            1375            1380

Asp Gly Tyr Ser Ile Glu Cys Arg Lys Met Asp Thr Gln Glu Ile
    1385            1390            1395

Glu Phe Ser Arg Lys Leu Glu Lys Glu Lys Ser Leu Leu Asn Ile
    1400            1405            1410

Met Met Leu Val Pro His Lys Arg Tyr Leu Val Ser Ile Lys Val
    1415            1420            1425

Gln Ser Ala Gly Met Thr Ser Glu Val Val Glu Asp Ser Thr Ile
    1430            1435            1440

Thr Met Ile Asp Arg Pro Pro Gln Pro Pro Pro His Ile Arg Val
    1445            1450            1455

Asn Glu Lys Asp Val Leu Ile Ser Lys Ser Ser Ile Asn Phe Thr
    1460            1465            1470

Val Asn Cys Ser Trp Phe Ser Asp Thr Asn Gly Ala Val Lys Tyr
    1475            1480            1485

Phe Ala Val Val Val Arg Glu Ala Asp Ser Met Asp Glu Leu Lys
    1490            1495            1500

Pro Glu Gln Gln His Pro Leu Pro Ser Tyr Leu Glu Tyr Arg His
    1505            1510            1515

Asn Ala Ser Ile Arg Val Tyr Gln Thr Asn Tyr Phe Ala Ser Lys
    1520            1525            1530

Cys Ala Glu Ser Pro Asp Ser Ser Ser Lys Ser Phe Asn Ile Lys
    1535            1540            1545

Leu Gly Ala Glu Met Asp Ser Leu Gly Gly Lys Cys Asp Pro Ser
    1550            1555            1560

Gln Gln Lys Phe Cys Asp Gly Pro Leu Lys Pro His Thr Ala Tyr
    1565            1570            1575

Arg Ile Ser Ile Arg Ala Phe Thr Gln Leu Phe Asp Glu Asp Leu
    1580            1585            1590

Lys Glu Phe Thr Lys Pro Leu Tyr Ser Asp Thr Phe Phe Ser Met
    1595            1600            1605

Pro Ile Thr Thr Glu Ser Glu Pro Leu Phe Gly Val Ile Glu Gly

```
                 1610                  1615                  1620

Val  Ser  Ala  Gly  Leu  Phe  Leu  Ile  Gly  Met  Leu  Val  Ala  Leu  Val
                 1625                  1630                  1635

Ala  Phe  Phe  Ile  Cys  Arg  Gln  Lys  Ala  Ser  His  Ser  Arg  Glu  Arg
                 1640                  1645                  1650

Pro  Ser  Ala  Arg  Leu  Ser  Ile  Arg  Arg  Asp  Arg  Pro  Leu  Ser  Val
                 1655                  1660                  1665

His  Leu  Asn  Leu  Gly  Gln  Lys  Gly  Asn  Arg  Lys  Thr  Ser  Cys  Pro
                 1670                  1675                  1680

Ile  Lys  Ile  Asn  Gln  Phe  Glu  Gly  His  Phe  Met  Lys  Leu  Gln  Ala
                 1685                  1690                  1695

Asp  Ser  Asn  Tyr  Leu  Leu  Ser  Lys  Glu  Tyr  Glu  Asp  Leu  Lys  Asp
                 1700                  1705                  1710

Val  Gly  Arg  Ser  Gln  Ser  Cys  Asp  Ile  Ala  Leu  Leu  Pro  Glu  Asn
                 1715                  1720                  1725

Arg  Gly  Lys  Asn  Arg  Tyr  Asn  Asn  Ile  Leu  Pro  Tyr  Asp  Ala  Ser
                 1730                  1735                  1740

Arg  Val  Lys  Leu  Ser  Asn  Val  Asp  Asp  Pro  Cys  Ser  Asp  Tyr
                 1745                  1750                  1755

Ile  Asn  Ala  Ser  Tyr  Ile  Pro  Gly  Asn  Asn  Phe  Arg  Arg  Glu  Tyr
                 1760                  1765                  1770

Ile  Ala  Thr  Gln  Gly  Pro  Leu  Pro  Gly  Thr  Lys  Asp  Asp  Phe  Trp
                 1775                  1780                  1785

Lys  Met  Ala  Trp  Glu  Gln  Asn  Val  His  Asn  Ile  Val  Met  Val  Thr
                 1790                  1795                  1800

Gln  Cys  Val  Glu  Lys  Gly  Arg  Val  Lys  Cys  Asp  His  Tyr  Trp  Pro
                 1805                  1810                  1815

Ala  Asp  Gln  Asp  Pro  Leu  Tyr  Tyr  Gly  Asp  Leu  Ile  Leu  Gln  Met
                 1820                  1825                  1830

Val  Ser  Glu  Ser  Val  Leu  Pro  Glu  Trp  Thr  Ile  Arg  Glu  Phe  Lys
                 1835                  1840                  1845

Ile  Cys  Ser  Glu  Glu  Gln  Leu  Asp  Ala  His  Arg  Leu  Ile  Arg  His
                 1850                  1855                  1860

Phe  His  Tyr  Thr  Val  Trp  Pro  Asp  His  Gly  Val  Pro  Glu  Thr  Thr
                 1865                  1870                  1875

Gln  Ser  Leu  Ile  Gln  Phe  Val  Arg  Thr  Val  Arg  Asp  Tyr  Ile  Asn
                 1880                  1885                  1890

Arg  Ser  Pro  Gly  Ala  Gly  Pro  Thr  Val  Val  His  Cys  Ser  Ala  Gly
                 1895                  1900                  1905

Val  Gly  Arg  Thr  Gly  Thr  Phe  Val  Ala  Leu  Asp  Arg  Ile  Leu  Gln
                 1910                  1915                  1920

Gln  Leu  Asp  Ser  Lys  Asp  Ser  Val  Asp  Ile  Tyr  Gly  Ala  Val  His
                 1925                  1930                  1935

Asp  Leu  Arg  Leu  His  Arg  Val  His  Met  Val  Gln  Thr  Glu  Cys  Gln
                 1940                  1945                  1950

Tyr  Val  Tyr  Leu  His  Gln  Cys  Val  Arg  Asp  Val  Leu  Arg  Ala  Lys
                 1955                  1960                  1965

Lys  Leu  Arg  Asn  Glu  Gln  Glu  Asn  Pro  Leu  Phe  Pro  Ile  Tyr  Glu
                 1970                  1975                  1980

Asn  Val  Asn  Pro  Glu  Tyr  His  Arg  Asp  Ala  Ile  Tyr  Ser  Arg  His
                 1985                  1990                  1995

<210> SEQ ID NO 7
```

<211> LENGTH: 1619
<212> TYPE: PRT
<213> ORGANISM: Mus musculus

<400> SEQUENCE: 7

```
Met Leu Arg His Gly Ala Leu Thr Ala Leu Trp Ile Thr Leu Ser Val
1               5                   10                  15

Val Gln Thr Gly Val Ala Glu Gln Val Lys Cys Asn Phe Thr Leu Leu
            20                  25                  30

Glu Ser Arg Val Ser Ser Leu Ala Ser Ile Gln Trp Arg Thr Phe
        35                  40                  45

Ala Ser Pro Cys Asn Phe Ser Leu Ile Tyr Ser Ser Asp Thr Ser Gly
    50                  55                  60

Pro Met Trp Cys His Pro Ile Arg Ile Asp Asn Phe Thr Tyr Gly Cys
65                  70                  75                  80

Asn Pro Lys Asp Leu Gln Ala Gly Thr Val Tyr Asn Phe Arg Ile Val
                85                  90                  95

Ser Leu Asp Gly Glu Ser Thr Leu Val Leu Gln Thr Asp Pro Leu
            100                 105                 110

Pro Pro Ala Arg Phe Glu Val Asn Arg Glu Lys Thr Ala Ser Thr Thr
        115                 120                 125

Leu Gln Val Arg Trp Thr Pro Ser Ser Gly Lys Val Ser Trp Tyr Glu
130                 135                 140

Val Gln Leu Phe Asp His Asn Asn Gln Lys Ile Gln Glu Val Gln Val
145                 150                 155                 160

Gln Glu Ser Thr Thr Trp Ser Gln Tyr Thr Phe Leu Asn Leu Thr Glu
                165                 170                 175

Gly Asn Ser Tyr Lys Val Ala Ile Thr Ala Val Ser Gly Glu Lys Arg
            180                 185                 190

Ser Phe Pro Val Tyr Ile Asn Gly Ser Thr Val Pro Ser Pro Val Lys
        195                 200                 205

Asp Leu Gly Ile Ser Pro Asn Pro Asn Ser Leu Leu Ile Ser Trp Ser
210                 215                 220

Arg Gly Ser Gly Asn Val Glu Gln Tyr Arg Leu Val Leu Met Asp Lys
225                 230                 235                 240

Gly Ala Ile Val Gln Asp Thr Asn Val Asp Arg Arg Asp Thr Ser Tyr
                245                 250                 255

Ala Phe His Glu Leu Thr Pro Gly His Leu Tyr Asn Leu Thr Ile Val
            260                 265                 270

Thr Met Ala Ser Gly Leu Gln Asn Ser Arg Trp Lys Leu Val Arg Thr
        275                 280                 285

Ala Pro Met Glu Val Ser Asn Leu Lys Val Thr Asn Asp Gly Arg Leu
290                 295                 300

Thr Ser Leu Asn Val Lys Trp Gln Lys Pro Pro Gly Asp Val Asp Ser
305                 310                 315                 320

Tyr Ser Ile Thr Leu Ser His Gln Gly Thr Ile Lys Glu Ser Lys Thr
                325                 330                 335

Leu Ala Pro Pro Val Thr Glu Thr Gln Phe Lys Asp Leu Val Pro Gly
            340                 345                 350

Arg Leu Tyr Gln Val Thr Ile Ser Cys Ile Ser Gly Glu Leu Ser Ala
        355                 360                 365

Glu Lys Ser Ala Ala Gly Arg Thr Val Pro Glu Lys Val Arg Asn Leu
370                 375                 380

Val Ser Tyr Asn Glu Ile Trp Met Lys Ser Phe Thr Val Asn Trp Thr
```

```
385                 390                 395                 400
Pro Pro Ala Gly Asp Trp Glu His Tyr Arg Ile Val Leu Phe Asn Glu
                405                 410                 415
Ser Leu Val Leu Leu Asn Thr Thr Val Gly Lys Glu Glu Thr His Tyr
                420                 425                 430
Ala Leu Asp Gly Leu Glu Leu Ile Pro Gly Arg Gln Tyr Glu Ile Glu
                435                 440                 445
Val Ile Val Glu Ser Gly Asn Leu Arg Asn Ser Glu Arg Cys Gln Gly
                450                 455                 460
Arg Thr Val Pro Leu Ala Val Leu Gln Leu Arg Val Lys His Ala Asn
465                 470                 475                 480
Glu Thr Ser Leu Gly Ile Thr Trp Arg Ala Pro Leu Gly Glu Trp Glu
                485                 490                 495
Lys Tyr Ile Ile Ser Leu Met Asp Arg Glu Leu Leu Val Ile His Lys
                500                 505                 510
Ser Leu Ser Lys Asp Ala Lys Glu Phe Thr Phe Thr Asp Leu Met Pro
                515                 520                 525
Gly Arg Asn Tyr Lys Ala Thr Val Thr Ser Met Ser Gly Asp Leu Lys
                530                 535                 540
Gln Ser Ser Ser Ile Lys Gly Arg Thr Val Pro Ala Gln Val Thr Asp
545                 550                 555                 560
Leu His Val Asn Asn Gln Gly Met Thr Ser Ser Leu Phe Thr Asn Trp
                565                 570                 575
Thr Lys Ala Leu Gly Asp Val Glu Phe Tyr Gln Val Leu Leu Ile His
                580                 585                 590
Glu Asn Val Val Lys Asn Glu Ser Val Ser Ser Asp Thr Ser Arg
                595                 600                 605
Tyr Ser Phe Arg Ala Leu Lys Pro Gly Ser Leu Tyr Ser Val Val Val
                610                 615                 620
Thr Thr Val Ser Gly Gly Ile Ser Ser Arg Gln Val Val Ala Glu Gly
625                 630                 635                 640
Arg Thr Val Pro Ser Ser Val Ser Gly Val Thr Val Asn Asn Ser Gly
                645                 650                 655
Arg Asn Asp Tyr Leu Ser Val Ser Trp Leu Pro Ala Pro Gly Glu Val
                660                 665                 670
Asp His Tyr Val Val Ser Leu Ser His Glu Gly Lys Val Asp Gln Phe
675                 680                 685
Leu Ile Ile Ala Lys Ser Val Ser Glu Cys Ser Phe Ser Ser Leu Thr
                690                 695                 700
Pro Gly Arg Leu Tyr Asn Val Thr Val Thr Thr Lys Ser Gly Asn Tyr
705                 710                 715                 720
Ala Ser His Ser Phe Thr Glu Glu Arg Thr Val Pro Asp Lys Val Gln
                725                 730                 735
Gly Ile Ser Val Ser Asn Ser Ala Arg Ser Asp Tyr Leu Lys Val Ser
                740                 745                 750
Trp Val His Ala Thr Gly Asp Phe Asp His Tyr Glu Val Thr Ile Lys
                755                 760                 765
Asn Arg Glu Ser Phe Ile Gln Thr Lys Thr Ile Pro Lys Ser Glu Asn
                770                 775                 780
Glu Cys Glu Phe Ile Glu Leu Val Pro Gly Arg Leu Tyr Ser Val Thr
785                 790                 795                 800
Val Ser Thr Lys Ser Gly Gln Tyr Glu Ala Ser Glu Gln Gly Thr Gly
                805                 810                 815
```

```
Arg Thr Ile Pro Glu Pro Val Lys Asp Leu Thr Leu Leu Asn Arg Ser
            820                 825                 830

Thr Glu Asp Leu His Val Thr Trp Ser Arg Ala Asn Gly Asp Val Asp
        835                 840                 845

Gln Tyr Glu Val Gln Leu Leu Phe Asn Asp Met Lys Val Phe Pro His
    850                 855                 860

Ile His Leu Val Asn Thr Ala Thr Glu Tyr Lys Phe Thr Ala Leu Thr
865                 870                 875                 880

Pro Gly Arg His Tyr Lys Ile Leu Val Leu Thr Ile Ser Gly Asp Val
                885                 890                 895

Gln Gln Ser Ala Phe Ile Glu Gly Leu Pro Val Pro Ser Thr Val Lys
            900                 905                 910

Asn Ile His Ile Ser Ala Asn Gly Ala Thr Asp Arg Leu Met Val Thr
        915                 920                 925

Trp Ser Pro Gly Gly Gly Asp Val Asp Ser Tyr Val Val Ser Ala Phe
    930                 935                 940

Arg Gln Asp Glu Lys Val Asp Ser Gln Thr Ile Pro Lys His Ala Ser
945                 950                 955                 960

Glu His Thr Phe His Arg Leu Glu Ala Gly Ala Lys Tyr Arg Ile Ala
                965                 970                 975

Ile Val Ser Val Ser Gly Ser Leu Arg Asn Gln Ile Asp Ala Leu Gly
            980                 985                 990

Gln Thr Val Pro Ala Ser Val Gln  Gly Val Val Ala Ala  Asn Ala Tyr
        995                 1000                 1005

Ser Ser  Asn Ser Leu Thr Val  Ser Trp Gln Lys Ala  Leu Gly Val
    1010                 1015                 1020

Ala Glu  Arg Tyr Asp Ile Leu  Leu Leu Asn Glu Asn  Gly Leu Leu
    1025                 1030                 1035

Leu Ser  Asn Val Ser Glu Pro  Ala Thr Ala Arg Gln  His Lys Phe
    1040                 1045                 1050

Glu Asp  Leu Thr Pro Gly Lys  Lys Tyr Lys Met Gln  Ile Leu Thr
    1055                 1060                 1065

Val Ser  Gly Gly Leu Phe Ser  Lys Glu Ser Gln Ala  Glu Gly Arg
    1070                 1075                 1080

Thr Val  Pro Ala Ala Val Thr  Asn Leu Arg Ile Thr  Glu Asn Ser
    1085                 1090                 1095

Ser Arg  Tyr Leu Ser Phe Gly  Trp Thr Ala Ser Glu  Gly Glu Leu
    1100                 1105                 1110

Ser Trp  Tyr Asn Ile Phe Leu  Tyr Asn Pro Asp Arg  Thr Leu Gln
    1115                 1120                 1125

Glu Arg  Ala Gln Val Asp Pro  Leu Val Gln Ser Phe  Ser Phe Gln
    1130                 1135                 1140

Asn Leu  Leu Gln Gly Arg Met  Tyr Lys Met Val Ile  Val Thr His
    1145                 1150                 1155

Ser Gly  Glu Leu Ser Asn Glu  Ser Phe Ile Phe Gly  Arg Thr Val
    1160                 1165                 1170

Pro Ala  Ala Val Asn His Leu  Lys Gly Ser His Arg  Asn Thr Thr
    1175                 1180                 1185

Asp Ser  Leu Trp Phe Ser Trp  Ser Pro Ala Ser Gly  Asp Phe Asp
    1190                 1195                 1200

Phe Tyr  Glu Leu Ile Leu Tyr  Asn Pro Asn Gly Thr  Lys Lys Glu
    1205                 1210                 1215
```

-continued

```
Asn Trp Lys Glu Lys Asp Val Thr Glu Trp Arg Phe Gln Gly Leu
1220                1225                1230

Val Pro Gly Arg Lys Tyr Thr Leu Tyr Val Val Thr His Ser Gly
1235                1240                1245

Asp Leu Ser Asn Lys Val Thr Gly Glu Gly Arg Thr Ala Pro Ser
1250                1255                1260

Pro Pro Ser Leu Leu Ser Phe Ala Asp Val Ala Asn Thr Ser Leu
1265                1270                1275

Ala Ile Thr Trp Lys Gly Pro Pro Asp Trp Thr Asp Tyr Asn Asp
1280                1285                1290

Phe Glu Leu Gln Trp Phe Pro Gly Asp Ala Leu Thr Ile Phe Asn
1295                1300                1305

Pro Tyr Ser Ser Arg Lys Ser Glu Gly Arg Ile Val Tyr Gly Leu
1310                1315                1320

His Pro Gly Arg Ser Tyr Gln Phe Ser Val Lys Thr Val Ser Gly
1325                1330                1335

Asp Ser Trp Lys Thr Tyr Ser Lys Pro Ile Ser Gly Ser Val Arg
1340                1345                1350

Thr Lys Pro Asp Lys Ile Gln Asn Leu His Cys Arg Pro Gln Asn
1355                1360                1365

Ser Thr Ala Ile Ala Cys Ser Trp Ile Pro Pro Asp Ser Asp Phe
1370                1375                1380

Asp Gly Tyr Ser Ile Glu Cys Arg Lys Met Asp Thr Gln Glu Ile
1385                1390                1395

Glu Phe Ser Arg Lys Leu Glu Lys Glu Lys Ser Leu Leu Asn Ile
1400                1405                1410

Met Met Leu Val Pro His Lys Arg Tyr Leu Val Ser Ile Lys Val
1415                1420                1425

Gln Ser Ala Gly Met Thr Ser Glu Val Val Glu Asp Ser Thr Ile
1430                1435                1440

Thr Met Ile Asp Arg Pro Pro Gln Pro Pro His Ile Arg Val
1445                1450                1455

Asn Glu Lys Asp Val Leu Ile Ser Lys Ser Ser Ile Asn Phe Thr
1460                1465                1470

Val Asn Cys Ser Trp Phe Ser Asp Thr Asn Gly Ala Val Lys Tyr
1475                1480                1485

Phe Ala Val Val Val Arg Glu Ala Asp Ser Met Asp Glu Leu Lys
1490                1495                1500

Pro Glu Gln Gln His Pro Leu Pro Ser Tyr Leu Glu Tyr Arg His
1505                1510                1515

Asn Ala Ser Ile Arg Val Tyr Gln Thr Asn Tyr Phe Ala Ser Lys
1520                1525                1530

Cys Ala Glu Ser Pro Asp Ser Ser Ser Lys Ser Phe Asn Ile Lys
1535                1540                1545

Leu Gly Ala Glu Met Asp Ser Leu Gly Gly Lys Cys Asp Pro Ser
1550                1555                1560

Gln Gln Lys Phe Cys Asp Gly Pro Leu Lys Pro His Thr Ala Tyr
1565                1570                1575
```

-continued

```
Arg Ile Ser Ile Arg Ala Phe Thr Gln Leu Phe Asp Glu Asp Leu
    1580            1585            1590

Lys Glu Phe Thr Lys Pro Leu Tyr Ser Asp Thr Phe Phe Ser Met
    1595            1600            1605

Pro Ile Thr Thr Glu Ser Glu Pro Leu Phe Gly
    1610            1615
```

METHODS FOR TREATING VASCULAR LEAK SYNDROME AND CANCER

CROSS-REFERENCE TO RELATED APPLICATION

This application is a Continuation Application of U.S. application Ser. No. 13/652,203, filed Oct. 15, 2012, which claims priority to U.S. Provisional Application Ser. No. 61/546,748 filed Oct. 13, 2011 and to U.S. Provisional Application Ser. No. 61/546,697 filed Oct. 13, 2011, each of which is in incorporated by reference in their entirety.

INCORPORATION BY REFERENCE OF MATERIAL SUBMITTED ELECTRONICALLY

Incorporated by reference in its entirety is a computer-readable sequence listing submitted concurrently herewith and identified as follows: One 93,959 Bytes ASCII (Text) file named "45725711301 SL," created on Feb. 15, 2017.

FIELD

Methods for treating cancer, preventing metastasis and vascular leak syndrome by administration of a HPTPβ inhibitor.

BACKGROUND

Vascular leak syndrome (VLS) is characterized by hypotension, peripheral edema and hypoalbuminemia. VLS can occur as a side effect of illness especially illnesses due to pathogens, inter alia, viruses and bacteria. Vascular leak complicates the healing process and can itself be a direct result of certain therapies. For example, patients suffering from malignant renal carcinoma are given Interleukin-2 (IL-2) to help boost their immune system. However, this treatment must be withdrawn in many patients due to the onset of severe VLS well before the full course of treatment can be administered. VLS restricts the doses of IL-2 which can be administered to humans and, in some cases, necessitates the cessation of therapy before the therapy is maximally effective.

VLS is characterized by an increase in vascular permeability accompanied by extravasation of fluids and proteins resulting in interstitial edema and organ failure. Manifestations of VLS include fluid retention, increase in body weight, peripheral edema, pleural and pericardial effusions, ascites, anasarca and, in severe form, signs of pulmonary and cardiovascular failure. Symptoms are highly variable among patients and the causes are poorly understood. Endothelial cell modifications or damage are thought to be important is vascular leak. The pathogenesis of endothelial cell (EC) damage is complex and can involve activation or damage to ECs and leukocytes, release of cytokines and of inflammatory mediators, alteration in cell-cell and cell-matrix adhesion and in cytoskeleton function.

One of the most frightening aspects of cancer is its ability to spread, or metastasize. Initially, cancer cells are found grouped together thereby forming one or more tumors. After formation of the primary tumor, cancer cells can gain the ability to separate from the original tumor and travel to other areas of the body. Lung cancer cells that take up in the liver and form tumors are still lung cancer cells. Thus, the propensity for one particular form of cancer to metastasize is dependent on many factors, including type of cancer; however, the overall process of how cells begin the process of metastasis is still not completely understood.

If a single localized tumor is discovered before it has had a chance to metastasize, then the prognosis of patient survival is higher. This is because the tumor can be effectively excised or destroyed by radiation or chemotherapy. There is, therefore, a difference between tumor growth and metastasis of the tumor cells; the first does not always lead to the other. Cancers that have metastasized, however, are difficult to cure because of extent to which they have spread throughout the body.

In order to metastasize, a cancer cell must break away from its tumor and invade either the circulatory or lymph system. The free cells are then carried to a new location where they establish themselves. Although the body has natural safeguards that prevent cell from surviving after being detached from their natural location, some cancer cells have the ability to overcome these safeguards. Therefore, if metastasis is stopped or significantly reduced, the extent of cancer can be determined and subsequently treated. As such, a follow up treatment to cancer therapy wherein a tumor has been excised or radiation/chemotherapy has been used, would be the treatment of the patient to an anti-metastasizing agent. There is a long felt need for methods of preventing cancer cell metastasis.

The growth of primary tumors also presents a challenge to treatment. If the growth of a primary tumor goes unchecked, the initial tumor can grow to a size that adversely effects organ function at the primary site and in nearby tissues. Metastasis of the primary tumor are also more likely if the primary tumor's growth is uncontrolled. There is a need for methods of slowing or preventing tumor growth.

During the course of antiviral and antibacterial infections, patients can develop vascular leak that is induced as result of the initial infection. There is now a long felt need for a method of preventing vascular leak due to viral or bacterial infection, and for providing methods of increasing the survival of humans or other mammals infected with one or more pathogens. In addition, there is a long felt need for a method of preventing vascular leakage due to certain anti-cancer drugs or other anticancer therapies such that the administration of anticancer drugs or anticancer therapies can be given to humans or other mammals for a longer course of treatment or therapy.

SUMMARY

The present disclosure provides methods for treating a patient having vascular leak syndrome comprising administering to the patient a composition comprising an effective amount of an HPTPβ-ECD binding agent or a pharmaceutically acceptable salt thereof.

Also provided are methods for treating a patient having vascular leak syndrome comprising administering to the patient, a composition comprising an effective amount of an HPTPβ-ECD binding agent or a pharmaceutically acceptable salt thereof, and one or more pharmaceutically acceptable excipient.

The present disclosure provides for methods of treating vascular leak wherein the patient being treated is suffering from an inflammatory disease or condition, trauma, shock, adult respiratory distress syndrome, acute lung injury, or sepsis comprising administering to the patient, a composition comprising an effective amount of an HPTPβ-ECD binding agent or a pharmaceutically acceptable salt thereof.

The present disclosure also provides for methods of treating vascular leak wherein the patient being treated is suffering from an inflammatory disease or condition, trauma, shock, adult respiratory distress syndrome, acute lung injury, or sepsis comprising administering to the patient, a composition comprising an effective amount of an HPTPβ-ECD binding agent or a pharmaceutically acceptable salt thereof, and one or more pharmaceutically acceptable excipient.

Another method provided by the present disclosure, is a method for determining the course of treatment for a patient suffering from vascular leak syndrome, comprising: a) administering to a patient a composition comprising an effective amount of an HPTPβ-ECD binding agent; b) monitoring the level of angiopoietin-2 present in the patient during the course of treatment; and c) discontinuing treatment when the angiopoietin-2 level returns to within a normal range.

A further method provided by the present disclosure is a method for treating cancer in a patient, comprising administering to a patient a composition comprising an effective amount of an HPTPβ-ECD binding agent or a pharmaceutically acceptable salt thereof.

A further method provided by the present is a method for treating cancer in a patient, comprising administering to a patient a composition comprising an effective amount of an HPTPβ-ECD binding agent or a pharmaceutically acceptable salt thereof, and a pharmaceutically acceptable excipient.

Still another method provided by the present disclosure is a method for preventing metastasis in a patient with cancer, by administering to a patient a composition comprising an effective amount of an HPTPβ-ECD binding agent or a pharmaceutically acceptable salt thereof.

Still another method provided by the present disclosure is a method for preventing metastasis in a patient with cancer, by administering to a patient a composition comprising an effective amount of an HPTPβ-ECD binding agent or a pharmaceutically acceptable salt thereof, and a pharmaceutically acceptable excipient.

In the methods of the present disclosure, HPTPβ-ECD binding agents include, but are not limited to antibodies, proteins, peptides, aptamers, peptibodies, adnectins, or nucleic acids, that binds to the extracellular portion of HPTPβ.

DETAILED DESCRIPTION

General Definitions

Figure 1:
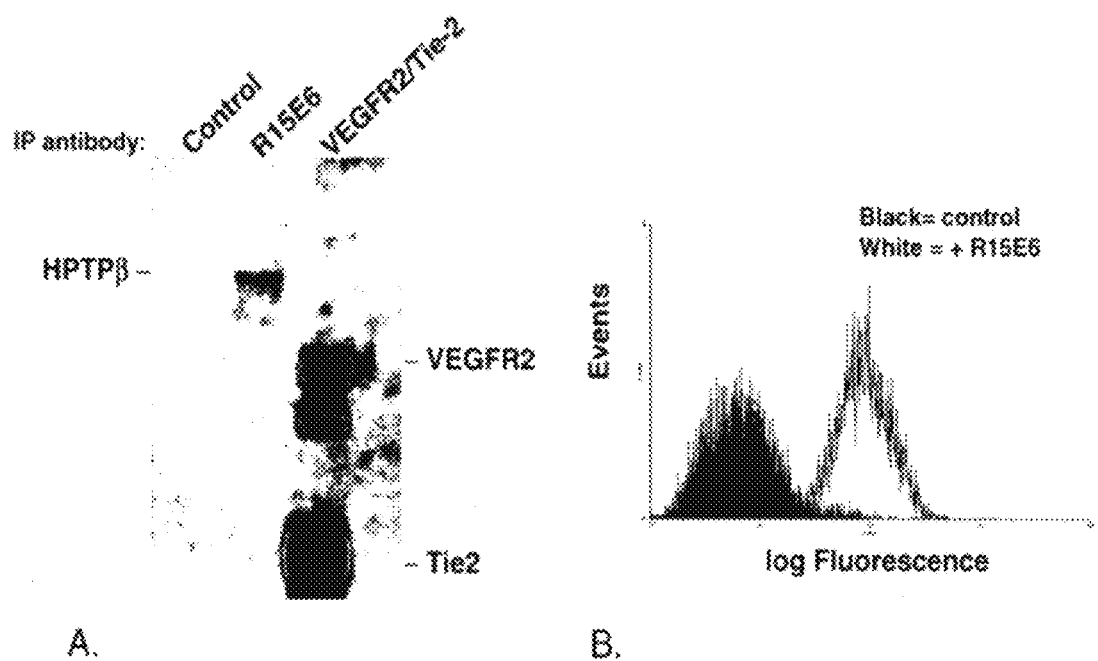
FIG. 1. The monoclonal antibody R15E6 recognizes endogenous HPTPβ on endothelial Cells. (Panel A) Endothelial cell lysates are immunoprecipitated with a control antibody (Lane 1), with R15E6 (Lane 2), or with a mixture of anti-Tie2 and anti-VEGFR2 antibodies (Lane 3). Immunoprecipitates are resolved by SDS-PAGE, transferred to a PVDF membrane and probed by western blot with a mixture of R15E6, anti-Tie2 and anti-VEGFR2 antibodies. A single major high molecular weight band consistent with HPTPβ is seen with R15E6 (Lane 2), and not with the control antibody (Lane 1), or the mixture of anti-Tie2 and anti-VEGFR2 (Lane 3). (Panel B) Endothelial cells are subjected to FACS analysis with R15E6 (white peak) or a no primary antibody control (black peak). The robust shift in fluorescence indicates that R15E6 binds to HPTPβ on the surface of intact endothelial cells.

In this specification and in the claims that follow, reference will be made to a number of terms, which shall be defined to have the following meanings:

The term "HPTPβ-ECD binding agent" and "specific binding agent" are used interchangeably herein and refer to a molecule that specifically binds to the extracellular portion of HPTPβ, and variants and derivatives thereof, as defined herein, that inhibits the Tie2 dephosphorylase activity of HPTPβ.

"Agent" as used herein refers to an "HPTPβ binding agent" or unless otherwise noted.

"Specifically binds HPTPβ-ECD" refers to the ability of a specific binding agent of the present invention to recognize and bind to an epitope of the extracellular domain of HPTPβ with higher affinity than to other related and/or unrelated molecules. Specific binding agents preferentially bind to HPTPβ in a complex mixture of proteins and/or macromolecules. The specific binding agent is preferably selective for HPTPβ. "Selective" means that the agent has significantly greater activity toward HPTPβ compared with other related and/or unrelated molecules, not that it is completely inactive with regard to other molecules. For example, a selective agent may show 10-fold, 100-fold, or 1000-fold selectivity toward HPTPβ than to other related or unrelated molecules.

The term "anti-HPTPβ-ECD antibodies" refers to antibodies or antibody fragments that bind to the extracellular domain of HPTPβ. Anti-HPTPβ-ECD antibodies are a type of HPTPβ-ECD binding agent as defined herein.

The term "VE-PTP" refers to the mouse ortholog of HPTPβ.

All percentages, ratios and proportions herein are by weight, unless otherwise specified. All temperatures are in degrees Celsius (° C.) unless otherwise specified.

Ranges may be expressed herein as from one particular value to another particular value, the endpoints are included in the range. For example for the range from "1 mg to 50 mg" includes the specific values 1 mg and 50 mg. The antecedent "about" indicates that the values are approximate. For example for the range from "about 1 mg to about 50 mg" indicates that the values are approximate values. Additionally, when such a range is expressed, the range includes the range "from 1 mg to 50 mg". It will be further understood that the endpoints of each of the ranges are significant both in relation to the other endpoint, and independently of the other endpoint. For example the range "from 1 mg to 50 mg", includes the range "from 30 mg to 40 mg."

As used herein, the term "in combination" refers to the use of more than one prophylactic and/or therapeutic agent. The use of the term "in combination" does not restrict the order in which prophylactic and/or therapeutic agents are administered to a patient. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a patient which had, has, or is susceptible to a disorder. The prophylactic or therapeutic agents are administered to a patient in a sequence and within a time interval such that the agent of the present disclosure can act together with the other agent to provide an increased benefit than if they were administered otherwise. Any additional prophylactic or therapeutic agent can be administered in any order with the other additional prophylactic or therapeutic agents "Effective amount" means an amount of an active agent or combination of agents effective to ameliorate or prevent the symptoms, or prolong the survival of the patient being treated. An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of this disclosure can be administered as frequently as necessary to achieve a therapeutic amount. Determination of a therapeutically effective amount is well within the capabilities of those skilled in the art, especially in light of the detailed disclosure provided herein.

As used herein the term "inhibit" or "inhibiting" refers to a statistically significant and measurable reduction in activity, preferably a reduction of at least about 10% versus control, more preferably a reduction of about 50% or more, still more preferably a reduction of about 80% or more.

As used herein the term "increase" or "increasing" refers to a statistically significant and measurable increase in activity, preferably an increase of at least about 10% versus control, more preferably an increase of about 50% or more, still more preferably an increase of about 80% or more.

"HPTP beta" or "HPTPβ" are used interchangeably herein and are abbreviations for human protein tyrosine phosphatase beta.

As used herein, "subject" means an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Patient" can also include a mammal, such as a primate or a human. "Subject" and "patient" are used interchangeably herein. Preferably the subject is a human.

By "reduce" or other forms of the word, such as "reducing" or "reduction," is meant lowering of an event or characteristic (e.g., vascular leakage). It is understood that this is typically in relation to some standard or expected value, in other words it is relative, but that it is not always necessary for the standard or relative value to be referred to.

The terms "treatment", "treating", "treat" and the like, refer to obtaining a desired pharmacologic and/or physiologic effect such as mitigating a disease or a disorder in a host and/or reducing, inhibiting, or eliminating a particular characteristic or event associated with a disorder (e.g., vascular leak). Thus, the term "treatment" includes, preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the HPTPβ-ECD binding agents of the disclosure may occur prior to onset of a disease. The term does not imply that the disease state is completely avoided.

As used herein, the term "cancer treatment" means any treatment for cancer known in the art including, but not limited to, chemotherapy and radiation therapy.

As used herein, the term "cancer treatment" means any treatment for cancer known in the art including, but not limited to, chemotherapy and radiation therapy.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions.

"Optional" or "optionally" means that the subsequently described event or circumstance can or cannot occur, and that the description includes instances where the event or circumstance occurs and instances where it does not.

"Specifically binds HPTPβ" refers to the ability of an agent of the present invention to recognize and bind to an epitope of the extracellular domain of HPTPβ with higher affinity than to the other related and/or unrelated molecules. The agent is preferably selective for HPTPβ. "Specific" means that the agent has significantly greater activity toward HPTPβ compared with other related and/or unrelated molecules, not that it is completely inactive with regard to other molecules. For example, a selective agent may show 10-fold, 100-fold, or 1000-fold selectivity toward HPTPβ than to other related or unrelated molecules.

The term "epitope" refers to any portion of any molecule capable of being recognized by and bound by an agent at one or more of the agent's antigen binding regions. Epitopes usually consist of distinct surface groupings such as amino acids, sugars, lipids, phosphoryl, or sulfonyl, and, in certain embodiments, may have specific three dimensional structural characteristics, and/or specific charge characteristics. Epitopes as used herein may be conformational or linear.

"Peptibody" is a molecule comprising an antibody Fc domain attached to at least one peptide. The production of peptibodies is generally described in WO2002/24782.

"Fragment" refers to a portion of an agent. A fragment may retain the desired biological activity of the agent and may be considered to be an agent itself. For example a truncated protein in which the amino terminus and/or carboxy terminus and/or an internal amino acid residue is deleted is a fragment of the protein and an Fab of an immunoglobulin molecule is a fragment of the immunoglobulin. Such fragments may also be connected to another molecule by way of a direct connection (e.g. a peptide or disulfide bond) or by way of a linker.

"Protein" is used herein interchangeably with peptide and polypeptide.

Peptides of the present invention include, but are not limited to amino acid sequences having from about 3 to about 75 amino acids, or from about 5 to about 50 amino acids, or from about 10 to about 25 amino acids. Peptides may be naturally occurring or artificial amino acid sequences.

A protein of the invention may be obtained by methods well known in the art, for example, using standard direct peptide synthesizing techniques such as via solid-phase synthesis. If the gene sequence is known or can be deduced then the protein may be produced by standard recombinant methods. The proteins may be isolated or purified in a variety of ways known to one skilled in the art. Standard purification methods include precipitation with salts, electrophoretic, chromatographic techniques and the like.

"Derivatives" include those binding agents that have been chemically modified in some manner distinct from insertion, deletion, or substitution variants. For example, wherein the binding agent is a protein, the carboxyl terminus may be capped with an amino group, such as $NH_2$.

In some embodiments one or more molecules are linked together to form the agent. For example antibody fragments may be connected by a linker. In general the chemical structure of the linker is not critical as it serves primarily as a space. In one embodiment the linker is made of amino acids linked together by way of peptide bonds. In another embodiment the linker is a non-peptide linker such as a non-sterically hindering $C_1$-$C_6$ alkyl group. In another embodiment the linker is a PEG linker. It will further be appreciated that the linker can be inserted in a number of locations on the molecule.

Variants of an agent are included within the scope of the present invention. "Variant" or "Variants" as used herein means an agent having a protein or nucleotide sequence which is substantially similar to the protein or nucleotide sequence of the non-variant agent and which shares a similar activity of the non-variant agent. A protein or nucleotide sequence may be altered in various ways to yield a variant encompassed by the present invention, including substitutions, deletions, truncations, insertions and other modifications. Methods for such manipulations are well known in the art. See, for example, Current Protocols in Molecular Biology (and updates) Ausubel et al., Eds (1996), John Wiley and Sons, New York: Methods in Molecular Biology, Vol. 182, In vitro Mutagenesis Protocols, 2nd Edition, Barman Ed. (2002), Humana Press), and the references cited therein. For example, variants include peptides and polypeptides wherein amino acid residues are inserted into, deleted from and/or substituted into the known amino acid sequence for the binding agent. In one embodiment, the substitution of the amino acid is conservative in that it minimally alters the biochemical properties of the variant. In other embodiments, the variant may be an active fragment of a full-length protein, a chemically modified protein, a protein modified by addition of affinity or epitope tags, or fluorescent or other labeling moieties, whether accomplished by in vivo or in vitro enzymatic treatment of the protein, by chemical modification, or by the synthesis of the protein using modified amino acids.

Fusions proteins are also contemplated herein. Using known methods, one of skill in the art would be able to make fusion proteins of the proteins of the invention; that, while different from native form, may be useful. For example, the fusion partner may be a signal (or leader) polypeptide sequence that co-translationally or post-translationally directs transfer of the protein from its site of synthesis to another site (e.g., the yeast alpha-factor leader). Alternatively, it may be added to facilitate purification or identification of the protein of the invention (e.g., poly-His, Flag peptide, or fluorescent proteins).

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The techniques and procedures are generally performed according to conventional methods known in the art and as described in various general and more specific references that are cited and discussed throughout the present specification. Unless specific definitions are provided, the nomenclature utilized in connection with, and the laboratory procedures and techniques of, analytical chemistry, synthetic organic chemistry, and medicinal and pharmaceutical chemistry described herein are those known and commonly used in the art. Standard techniques may be used for chemical syntheses, chemical analyses, pharmaceutical preparation, formulation, delivery, and treatment of patients.

SEQUENCE LISTING

TABLE 1

| | |
|---|---|
| SEQ ID NO: 1 | Full length Human HPTPβ nucleotide sequence (X54131) |
| SEQ ID NO: 2 | Full length Human HPTPβ amino acid sequence (P23467) |
| SEQ ID NO: 3 | Extracellular Portion of Human HPTPβ with (His)$_6$Gly Tag |
| SEQ ID NO: 4 | Extracellular Portion of Human HPTPβ |
| SEQ ID NO: 5 | Full length mouse VE-PTP nucleotide sequence (AY077755) |
| SEQ ID NO: 6 | Full length mouse VE-PTP amino acid sequence (AAL75813) |
| SEQ ID NO: 7 | Extracellular portion of mouse VE-PTP amino acid sequence |

HPTPβ-ECD Binding Agents

Agents useful in the present invention include, but are not limited to, antibodies, proteins, darpins, peptides, aptamers, adnectins, peptibodies, or nucleic acids that bind specifically to the extracellular portion of HPTPβ and inhibit at least one phosphatase activity of HPTPβ. As used herein, "phosphatase activity" includes enzymatic activity and biologic activity where biological activity is measured by assessing Tie2 phosphorylation.

Agents useful in the present invention further include: antibodies, or antigen binding fragments thereof which bind to the extracellular portion of HPTPβ wherein the antibody or antigen-binding fragment inhibits at least one phosphatase activity of HPTPβ. These agents include monoclonal and polyclonal antibodies. An agent may be a fragment of an antibody, wherein the fragment comprises the heavy and light chain variable regions, or the fragment is an F(ab')$_2$, or the fragment is a dimer or trimer of an Fab, Fv, scFv, or a dia-, tria-, or tetrabody derived from the antibody.

For example, the agent may be, without limitation, an antibody or antibody fragment that binds the extracellular portion of HPTPβ; or in particular an antibody that binds an FN3 repeat of HPTPβ, or more specifically an antibody that binds the first FN3 repeat of HPTPβ.

Agents further include: the monoclonal antibody R15E6 which is described in U.S. Pat. No. 7,973,142, which is hereby incorporated in its entirety. (The mouse hybridoma, Balbc spleen cells (B cells) which may be used to produce the antibody are deposited with American Type Culture Collection (ATCC), P.O. Box 1549, Manassas, Va. 20108 USA on 4 May 2006, assigned ATCC No. PTA-7580) (Referred to herein as R15E6)), antibodies having the same or substantially the same biological characteristics of R15E6; antibody fragments of R15E6, wherein the fragment comprises the heavy and light chain variable regions; an F(ab')$_2$ of R15E6; dimers or trimers of an Fab, Fv, scFv; and dia-, tria-, or tetrabodies derived from R15E6.

In particular, an agent suitable for use in the present invention is an antibody, antibody fragment, variant or derivatives thereof, either alone or in combination with other amino acid sequences, provided by known techniques. Such techniques include, but are not limited to enzymatic cleavage, chemical cleavage, peptide synthesis or recombinant techniques. The invention further embraces derivative agents, e.g. peptibodies.

Thus, one embodiment of an HPTPβ-ECD binding agent is an antibody, another embodiment is a protein, yet another embodiment is a peptide, and another embodiment is a darpin, another embodiment is an aptamer, another embodiment is a peptibody, still another embodiment is an adnectin, another embodiment is a nucleic acid. In some embodiments the HPTPβ-ECD binding agent is a monoclonal antibody, or is a polyclonal antibody. In particular embodiments, the HPTPβ-ECD binding agent is an antibody fragment that is capable of binding to HPTPβ-ECD. Preferably the HPTPβ-ECD binding agent is an antibody, or an antibody fragment, including but not limited to, an F(ab')$_2$, an Fab, a dimer of an Fab, an Fv, a dimer of an Fv, a scFv, a dimer of a scFv, a dimer an Fab, an Fv, a dimer of an Fv, a scFv, a dimer of a scFv, a trimer of an Fab, a trimer of an Fv, a trimer of a scFv, minibodies, a diabody, a triabody, a tetrabody, a linear antibody, a protein, a peptide, an aptamer, a peptibody, an adnectin, or a nucleic acid, that binds to the extracellular portion of HPTPβ. In certain embodiments the HPTPβ-ECD binding agent is and F(ab')$_2$ of a monoclonal antibody. In some embodiments the HPTPβ-ECD binding agent comprises a plurality of HPTPβ-ECD binding sites, for example where the HPTPβ-ECD binding agent is an intact antibody or an F(ab')$_2$, or a dimer of an Fab, or a trimer of an Fab. For example, in some embodiments an HPTPβ-ECD binding agent is able to bind to two HPTPβ molecules simultaneously at the same or different epitope, thereby bringing the two HPTPβ molecules into close proximity with one and other. In other embodiments the HPTPβ-ECD binding agent is able to bind to three HPTPβ molecules simultaneously at the same or different epitope, thereby bringing the three HPTPβ molecules into close proximity with one and other. In another embodiment, the HPTPβ-ECD binding agent is the monoclonal antibody produced by hybridoma cell line ATCC No. PTA 7680 PTA-7580. In yet another embodiment, the HPTPβ-ECD binding agent is an antigen binding fragment of the monoclonal antibody produced by hybridoma cell line ATCC No. PTA 7680 PTA-7580. In still another embodiment, the HPTPβ-ECD binding agent is an antibody having the same or substantially the same biological characteristics the monoclonal antibody produced by hybridoma cell line ATCC No. PTA 7680 PTA-7580 or an antigen binding fragment thereof.

Any of the embodiments of HPTPβ-ECD binding agents disclosed in the present application, may be covalently or non-covalently conjugated to a vehicle. The term "vehicle" refers to a molecule that affects a biological property of an agent. For example, a vehicle may prevent degradation, and/or increase half-life, absorption, reduce toxicity, reduce immunogenicity, or increase biological activity of the agent. Exemplary vehicles include, but are not limited to, Fc domains of immunoglobulins; polymers, for example: polyethylene glycol (PEG), polylysine, dextran; lipids; cholesterol groups (such as a steroid); carbohydrates, dendrimers, oligosaccharides, or peptides that binds to a salvage receptor. In some embodiments the vehicle is polyethylene glycol (PEG), in other embodiments the vehicle is polylysine, in yet other embodiments the vehicle is dextran, in still other embodiments the vehicle is a lipid Water soluble polymer attachments, such as polyethylene glycol, polyoxyethylene glycol, or polypropylene glycol, as described U.S. Pat. Nos. 4,640,835, 4,496,689, 4,301,144, 4,670,417, 4,791,192, and 4,179,337, which are incorporated herein in their entirety. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers. Particularly preferred are peptibodies covalently modified with polyethylene glycol (PEG) subunits. Water soluble polymers may be bonded at specific positions, for example at the amino terminus of the peptibodies, or randomly attached to one or more side chains of the polypeptide. The use of PEG for improving the therapeutic capacity for agents, e.g. peptibodies, and for humanized antibodies in particular, is described in U.S. Pat. No. 6,133,426. The invention also contemplates derivatizing the peptide and/or vehicle portion of the agents. Such derivatives may improve the solubility, absorption, biological half-life, and the like of the agents. The moieties may alternatively eliminate or attenuate any undesirable side-effect of the agents and the like.

The term "antibody" (Ab) as used herein includes monoclonal antibodies, polyclonal antibodies, multi-specific antibodies (e.g. bispecific antibodies), single chain antibodies, e.g., antibodies from llama and camel, antibody fragments, e.g., variable regions and/or constant region fragments, so long as they exhibit a desired biological activity, e.g., antigen-binding activity. The term "immunoglobulin" (Ig) is used interchangeably with "antibody" herein.

An "antigen binding fragment" as used herein is a fragment of an agent that binds to a portion of HPTPβ and inhibits at least one phosphatase activity of HPTPβ.

The basic four-chain antibody unit is a heterotetrameric glycoprotein composed of two identical light (L) chains and two identical heavy (H) chains (an IgM antibody consists of 5 of the basic heterotetramer units along with an additional polypeptide called J chain, and therefore contain 10 antigen binding sites, while secreted IgA antibodies may polymerize to form polyvalent assemblages comprising 2-5 of the basic 4-chain units along with J chain). In the case of IgGs, the four-chain unit is generally about 150 kilo Daltons (kDa). Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the alpha and gamma chains and four $C_H$ domains for mu and epsilon isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Ten and Tristram G. Parslow (eds.), Appleton & Lange, 1994, page 71 and Chapter 6.

The L chain from any vertebrate species may be assigned to one of two clearly distinct types, called kappa and lambda, based on the amino acid sequences of their constant domains. Depending on the amino acid sequence of the constant domain of their heavy chains ($C_H$), immunoglobulins may be assigned to different classes or isotypes. There are five classes of immunoglobulins: IgA, IgD, IgE, IgG and IgM, having heavy chains designated alpha, delta, epsilon, gamma and mu, respectively. The gamma and alpha classes are further divided into subclasses on the basis of relatively minor differences in $C_H$ sequence and function, e.g., humans express the following subclasses: IgG1, IgG2, IgG3, IgG4, IgA1 and IgA2.

Members of the Camelidae family, e.g., llama, camel, and dromedaries, contain a unique type of antibody, that are devoid of light chains, and further lack the $C_{H1}$ domain (Muyldermans, S., Rev. Mol. Biotechnol., 74, 277-302 (2001)). The variable region of these heavy chain antibodies are termed $V_{HH}$ or VHH, and constitute the smallest available intact antigen binding fragment (15 kDa) derived from a functional immunoglobulin.

The term "variable" refers to the fact that certain segments of the variable domains differ extensively in sequence among antibodies. The V domain mediates antigen binding and defines specificity of a particular antibody for its antigen. However, the variability is not evenly distributed across the 110-amino acid span of the variable domains. Instead, the V regions consist of relatively invariant stretches called framework regions (FR) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies. The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., Sequences of Proteins of Immunological Interest, 5th Ed. Public Health Service, National Institutes of Health, Bethesda, Md. (1991)) and/or those residues from a "hypervariable loop".

The term "monoclonal antibody" as used herein refers to an antibody obtained from a population of substantially homogeneous antibodies, i.e., the individual antibodies comprising the population are identical except for possible naturally occurring mutations that may be present in minor amounts. In contrast to polyclonal antibody preparations which include different antibodies directed against different epitopes, each monoclonal antibody is directed against a single epitope, i.e., a single antigenic determinant. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology or may be made using recombinant DNA methods in bacterial, eukaryotic animal or plant cells (see, e.g., U.S. Pat. No. 4,816,567). The "monoclonal antibodies" may also be isolated from phage antibody libraries, using the available techniques, e.g., Clackson et al., Nature, Vol. 352, pp. 624-628 (1991).

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81, 6851-6855 (1984)).

An "antibody fragment" comprises a portion of a multimeric antibody, preferably the antigen binding or variable region of the intact antibody. Examples of antibody fragments include Fab, Fab', F(ab')$_2$, dimers and trimers of Fabs, Fv, scFv, minibodies; dia-, tria-, and tetrabodies; linear antibodies (See Hudson et al., Nature Med. 9, 129-134 (2003)).

"Fv" is the minimum antibody fragment which contains a complete antigen binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, and are therefore included in the definition of Fv.

A single-chain variable fragment (scFv) is a fusion protein of the variable regions of the heavy ($V_H$) and light chains ($V_L$) of immunoglobulins, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker.

Divalent (or bivalent) single-chain variable fragments (di-scFvs, bi-scFvs) can be engineered by linking two scFvs. This can be done by producing a single peptide chain with two $V_H$ and two $V_L$ regions, yielding tandem scFvs. Another possibility is the creation of scFvs with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Consequently, diabody drugs could be dosed much lower than other therapeutic antibodies and are capable of highly specific targeting of tumors in vivo. Still shorter linkers (one or two amino acids) lead to the formation of trimers, so-called triabodies or tribodies. Tetrabodies are known and have been shown to exhibit an even higher affinity to their targets than diabodies.

The term "humanized antibody" or "human antibody" refers to antibodies which comprise heavy and light chain variable region sequences from a non-human species (e.g., a mouse) but in which at least a portion of the $V_H$ and/or $V_L$ sequence has been altered to be more "human-like", i.e., more similar to human germline variable sequences. One type of humanized antibody is a CDR-grafted antibody, in which human CDR sequences are introduced into non-human $V_H$ and $V_L$ sequences to replace the corresponding nonhuman CDR sequences. Means for making chimeric, CDR-grafted and humanized antibodies are known to those of ordinary skill in the art (see, e.g., U.S. Pat. Nos. 4,816,567 and 5,225,539). One method for making human antibodies employs the use of transgenic animals, such as a transgenic mouse. These transgenic animals contain a substantial portion of the human antibody producing genome inserted into their own genome and the animal's own endogenous antibody production is rendered deficient in the production of antibodies. Methods for making such transgenic animals are known in the art. Such transgenic animals may be made using XenoMouse® technology or by using a "minilocus" approach. Methods for making XenoMice® are described in U.S. Pat. Nos. 6,162,963, 6,150,584, 6,114,598 and 6,075,181. Methods for making transgenic animals using the "minilocus" approach are described in U.S. Pat. Nos. 5,545,807, 5,545,806, 5,625,825, and WO 93/12227.

Humanization of a non-human antibody has become routine in recent years, and is now within the knowledge of one skilled in the art. Several companies provide services to make a humanized antibody, e.g., Xoma, Aries, Medarex, PDL, and Cambridge Antibody Technologies. Humanization protocols are extensively described in technical literature, e.g., Kipriyanov and Le Gall, Molecular Biotechnol., Vol. 26, pp. 39-60 (2004), Humana Press, Totowa, N.J.; Lo, Methods Mol. Biol., Vol. 248, pp. 135-159 (2004), Humana Press, Totowa, N.J.; Wu et al., J. Mol. Biol., 294, pp. 151-162 (1999).

In certain embodiments, antibodies useful in the present invention may be expressed in cell lines other than hybridoma cell lines. Sequences encoding particular antibodies may be used for transformation of a suitable mammalian host cell by known methods for introducing polynucleotides into a host cell, including, for example packaging the polynucleotide in a virus (or into a viral vector) and transducing a host cell with the virus (or vector), or by transfection procedures known in the art, as exemplified by U.S. Pat. Nos. 4,399,216, 4,912,040, 4,740,461 and 4,959,455. The transformation procedure used may depend upon the host to be transformed. Methods for introduction of heterologous polynucleotides into mammalian cells are known in the art and include; but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

A nucleic acid molecule encoding the amino acid sequence of a heavy chain constant region, a heavy chain variable region, a light chain constant region, or a light chain variable region of an antibody, or a fragment thereof in a suitable combination if desired, is/are inserted into an appropriate expression vector using standard ligation techniques. The antibody heavy chain or light chain constant region may be appended to the C-terminus of the appropriate variable region and is ligated into an expression vector. The vector is typically selected to be functional in the particular host cell employed (i.e., the vector is compatible with the host cell machinery such that amplification of the gene and/or expression of the gene may occur). For a review of expression vectors, see Methods Enzymol. Vol. 185 (Goeddel, ed.), 1990, Academic Press.

Identification of Specific Binding Agents

Suitable selective binding agents may be identified using a variety of techniques known in the art. For example candidate agents can be screened for binding to HPTPβ, and screened for activity. Generally the candidate agents will first be screened for binding and those that show selective binding will then be screened to determine ability to inhibit the HPTPβ-mediated dephosphorylation of Tie2. In some cases however the candidate agents may be first screened in vitro for activity.

Determination of Binding Activity

The selection of a suitable assay for use in identification of a specific binding agent depends on the nature of the candidate agent to be screened. One of skill in the art would be able to choose the appropriate assays for the particular candidate agent.

For example, where the candidates are antibodies or peptibodies which comprises an Fc moiety, FACS analysis as described in Example 3 B allows the candidate agent to be selected based on its ability to bind to cells which express HPTPβ. The cell may endogenously express HPTPβ or may be genetically engineered to express HPTPβ.

For other candidate agents such as aptamers, other techniques are known in the art. For example, aptamers which specifically bind to HPTPβ can be selected using a technique known as SELEX (systematic evolution of ligands by exponential enrichment) which selects specific aptamers through repeated rounds of in vitro selection.

Determination of Inhibitor Activity by Western Blot

As exemplified in Example 4, in one suitable assay HUVECs are cultured in serum-free media in the presence or absence of various concentrations of candidate agent and lysates of the cells are prepared, immunoprecipitated with a Tie2 antibody, resolved by polyacrylamide gel electrophoresis and transferred to a PVDF membrane. Membrane-bound immunoprecipitated proteins are then serially western blotted with an antiphosphotyrosine antibody to quantify Tie2 phosphorylation followed by a Tie2 antibody to quantify total Tie2. Tie2 phosphorylation is expressed as the ratio of the anti-phosphotyrosine signal over the total Tie2 signal. Greater levels of the anti-phosphotyrosine signal indicate greater HPTPβ inhibition by the candidate agent.

Candidate agents that can be screened include, but are not limited to, libraries of known agents, including natural products, such as plant or animal extracts, biologically active molecules including proteins, peptides including but not limited to members of random peptide libraries and combinatorial chemistry derived molecular library made of D- or L-configuration amino acids, antibodies including, but not limited to, polyclonal, monoclonal, chimeric, human, single chain antibodies, Fab, F(ab)$_2$ and Fab expression library fragments and eptiope-binding fragments thereof).

As used herein "antibody fragments" include, but are not limited, to an F(ab')$_2$, a dimer or trimer of an Fab, Fv, scFv, or a dia-, tria-, or tetrabody derived from an antibody.

Throughout this application, various publications are referenced. The disclosures of these publications in their entireties are hereby incorporated by reference into this application in order to more fully describe the state of the art.

The vascular endothelium lines the inside of all blood vessels, forming a non-thrombogenic surface that controls the entry and exit of plasma and white blood cells to and from the bloodstream. The quiescent endothelium has turn-over rates of months to years, and proliferates only following angiogenic activation. The loss of endothelial quiescence is a common feature of conditions such as inflammation, atherosclerosis, restenosis, angiogenesis and various types of vasculopathies.

Vasculogenesis and angiogenesis are down-regulated in the healthy adult and are, except for the organs of the female reproductive system, almost exclusively associated with pathology when angiogenesis is induced by microenvironmental factors such as hypoxia or inflammation. These pathological processes associated with, or induced by, angiogenesis include diseases as diverse as cancer, psoriasis, macular degeneration, diabetic retinopathy, thrombosis, and inflammatory disorders including arthritis and atherosclerosis. However, in certain instances insufficient angiogenesis can lead to diseases such as ischemic heart disease and pre-eclampsia.

The quiescent vascular endothelium forms a tight barrier that controls the passage of plasma and cells from the bloodstream to the underlying tissues. Endothelial cells adhere to each other through junctional transmembrane proteins that are linked to specific intracellular structural and signaling complexes. The endothelial layer can undergo a transition from the resting state to the active state wherein activation of the endothelium results in the expression of adhesion molecules. This endothelium activation is a prerequisite for initiating angiogeniesis, inflammation and inflammation associated diseases.

Tie-2, a receptor-like tyrosine kinase exclusively expressed in endothelial cells that controls endothelial differentiation. Tie-2 binds and is activated by the stimulatory ligand angiopoeitin-1 (Ang-1) which promotes autophosphorylation of the Tie-2 receptor leading to a cascade of events that results in stabilization of vascular structures by promoting endothelial cell viability and preventing basement membrane dissolution. As such, Tie-2 activation is a method for attenuating leaking vasculature by maintaining a quiescent, intact vascular endothelium. Tie-2 activation is inhibited by Ang-2, which exhibits Ang-1 antagonism by competitively binding to Tie-2 and thus blocking phosphorylation of Tie-2. Elevated levels of Ang-2 have been found to be associated with inflammatory diseases, inter alia, sepsis, lupus, inflammatory bowel disease and metastatic diseases such as cancer.

During periods of high Ang-2 levels, fissures or breaks in the endothelium form which results in vascular leak syndrome. Vascular leak syndrome results in life-threatening effects such as tissue and pulmonary edema. For many disease states elevated Ang-2 levels are clear markers that a disease state or condition exists. Once a disease state has been resolved, the Ang-1/Ang-2 balance returns and the vascular endothelium is stabilized. In conditions wherein the normal balance between Ang-1 and Ang-2 has been disrupted, the disclosed agents have been found to amplify Tie-2 signaling by inhibiting dephosphorylation of phosphorylated Tie-2 via inhibition of Human Protein Tyrosine Phosphatase-β (HPTP-β). In addition, the disclosed agents can be used in varying amounts to increase the Tie-2 signaling in a very controlled manner, and to therefore titrate the level of Tie-2 amplification.

The present disclosure provides methods for treating a patient having vascular leak syndrome comprising administering to the patient a composition comprising effective amount of an HPTPβ-ECD binding agent or a pharmaceutically acceptable salt thereof. The compositions of the present disclosure may also comprise one or more pharmaceutically acceptable excipients.

Disclosed herein, are compositions comprising an HPTPβ-ECD binding agent wherein the compositions are useful for treatment of the disclosed conditions, illness, injuries, courses of treatment, cellular treatments and the like.

In one embodiment, the method comprises treating vascular leak in a patient wherein the patient suffers from an inflammatory disease or condition which comprises administering to the patient a composition comprising an effective amount of an HPTPβ-ECD binding agent. Another embodiment is a method of treating a patient suffering from a physical trauma comprising administering to the patient a composition comprising an effective amount of an HPTPβ-ECD binding agent. In a particular embodiment the trauma is surgical trauma. In one embodiment the method is a method of treating a patient suffering from shock comprising administering to the patient a composition comprising an effective amount of an HPTPβ-ECD binding agent.

Particular embodiments include post-hemorrhagic shock, or post-traumatic shock or septic shock. The present disclosure also provides for a method of treating a patient suffering from adult respiratory distress syndrome by administering to the patient a composition comprising an effective amount of an HPTPβ-ECD binding agent. Another embodiment is a method of treating a patient with an acute lung injury comprising administering to the patient a composition comprising an effective amount of an HPTPβ-ECD binding agent. Cancer metastasis and bacterial and viral infections are covered below.

In some embodiments an HPTPβ-ECD binding agent is administered prophylactically to stabilize the patient's vasculature prior to an event that places the patient at risk for vascular leak. In one embodiment the HPTPβ-ECD binding agent is administered prophylactically to stabilize the patient's vasculature prior to surgery. Still another embodiment is a method of preventing vascular leak syndrome in a patient wherein an effective amount of an HPTPβ-ECD binding agent is administered to the patient prior to undergoing chemotherapy. Another embodiment is a method of treating a patient at risk of shock comprising administering to the patient an effective amount of an HPTPβ-ECD binding agent.

The disclosed HPTPβ-ECD binding agents can be used to prevent, abate, minimize, control, and/or lessen tumor metastasis in humans and animals. The disclosed HPTPβ-ECD binding agents can also be used to slow the rate of primary tumor growth. As such, the agents disclosed herein can be administered as part of a combination therapy with one or more drugs or other pharmaceutical agents. When used as part of the combination therapy, the decrease in metastasis and reduction in primary tumor growth afforded by the disclosed agents allows for a more effective and efficient use of any pharmaceutical or drug therapy being used to treat the patient. In addition, control of metastasis by the disclosed agent affords the subject a greater ability to concentrate the disease in one location.

Thus, one embodiment of the present disclosure is a method of treating cancer in a patient comprising administering a composition comprising an effective amount of an HPTPβ-ECD binding agent or a pharmaceutically acceptable salt thereof. Another embodiment is a method of preventing metastasis in a patient suffering from cancer comprising administering a composition comprising an effective amount of an HPTPβ-ECD binding agent or a pharmaceutically acceptable salt thereof. Yet another embodiment is a method of minimizing tumor metastasis in a patient suffering from cancer comprising administering a composition comprising an effective amount of an HPTPβ-ECD binding agent or a pharmaceutically acceptable salt thereof. Disclosed herein are methods for preventing metastasis of malignant tumors or to reduce the rate of tumor growth. Thus, another embodiment is a method of treating a patient diagnosed with a malignant tumor comprising administering to the patient a composition comprising an effective amount of an HPTPβ-ECD binding agent or a pharmaceutically acceptable salt thereof. Another embodiment is a method of preventing metastasis in a patient diagnosed with a malignant tumor comprising administering to the patient a composition comprising an effective amount of an HPTPβ-ECD binding agent or a pharmaceutically acceptable salt thereof. Yet another embodiment is a method of reducing the rate of tumor growth in a patient diagnosed with a tumor comprising administering to the patient a composition comprising an effective amount of an HPTPβ-ECD binding agent or a pharmaceutically acceptable salt thereof.

The following are non-limiting examples of cancers that can be treated by the disclosed methods and compositions: leukemia, for example, chronic myelogenous leukemia; acute lymphoblastic leukemia, acute childhood myeloid leukemia; adult acute myeloid leukemia, hairy cell leukemia; lymphoma, for example, Burkitt's lymphoma, Hodgkin's lymphoma, non-Hodgkin's lymphoma, cutaneous t-cell lymphoma, central nervous system lymphoma; astrocytomas, for example, cerebellar astrocytoma, childhood astrocytoma, pilocytic astrocytoma, diffuse astrocytoma, anaplastic astrocytoma, gliomas, oligodendroglioma, cerebral astrocytoma visual pathway glioma and hypothalamic glioma, brain stem glioma, visual pathway, hypothalamic glioma, cerebral astrocytoma/malignant glioma; carcinoma, for example, thymoma carcinoma, thymic carcinoma, squamous cell carcinoma, skin carcinoma, Merkel cell carcinoma, adrenocortical carcinoma, adrenocortical carcinoma, basal cell carcinoma; sarcoma, for example, rhabdomyosarcoma sarcoma, Ewing sarcoma, Kaposi sarcoma, soft tissue sarcoma, uterine sarcoma, osteosarcoma, malignant fibrous histiocytoma of the bone; appendix cancer; extrahepatic bile duct cancer; bladder cancer; bone cancer; salivary gland cancer; brain tumor; childhood central nervous system atypical teratoid/rhabdoid tumor; central nervous system embryonal tumors; craniopharyngioma; ependymoblastoma; ependymoma; medulloblastoma; medulloepithelioma; pineal parenchymal tumors of intermediate differentiation; supratentorial primitive neuroectodermal tumors and pineoblastoma; brain and spinal cord tumors; breast cancer; bronchial tumors; carcinoid tumor; gastrointestinal carcinoid tumor; central nervous system embryonal tumors; cervical cancer; chordoma, childhood; chronic myeloproliferative disorders; colon cancer; colorectal cancer; craniopharyngioma; extragonadal germ cell tumor; testicular germ cell tumor; retinoblastoma; gallbladder cancer; gastric (stomach) cancer; gastrointestinal carcinoid tumor; gastrointestinal stromal tumor (gist); extracranial germ cell tumor; gestational trophoblastic tumor; glioblastoma; head and neck cancer; hepatocellular (liver) cancer; Langerhans cell histiocytosis; hypopharyngeal cancer; islet cell tumors; kidney (renal cell) cancer; laryngeal cancer; lip and oral cavity cancer; liver cancer; non-small cell lung cancer; small-cell lung cancer; mesothelioma; metastatic squamous neck cancer with occult primary; mouth cancer; childhood multiple endocrine neoplasia syndrome; multiple myeloma/plasma cell neoplasm; mycosis fungoides; myelodysplastic syndromes; multiple myeloma; myeloproliferative disorders, chronic; nasal cavity and paranasal sinus cancer; neuroblastoma; oral cancer; oropharyngeal cancer; ovarian cancer, for example, ovarian epithelial cancer, ovarian germ cell tumor, ovarian low malignant potential tumor; pancreatic cancer; islet cell tumors; papillomatosis; thyroid cancer; parathyroid cancer; penile cancer; esophageal cancer; pharyngeal cancer; nasopharyngeal cancer; pheochromocytoma; pineal parenchymal tumors; pituitary tumor; plasma cell neoplasm/multiple myeloma; pleuropulmonary blastoma; prostate cancer; rectal cancer; renal cell (kidney) cancer; renal pelvis and ureter cancer; Sézary syndrome; skin cancer (nonmelanoma); skin cancer (melanoma); intraocular melanoma; malignant melanoma, small intestine cancer; metastatic squamous neck cancer; stomach (gastric) cancer; testicular cancer; throat cancer; transitional cell cancer of the renal pelvis and ureter; gestational trophoblastic tumor; urethral cancer; uterine cancer, endometrial; vaginal cancer; vulvar cancer; Waldenström macroglobulinemia; and Wilms tumor.

The HPTPβ-ECD binding agents can be administered in combination with one or more chemotherapeutic agent.

A "chemotherapeutic agent" or "chemotherapeutic compound" is a chemical compound useful in the treatment of cancer. Chemotherapeutic cancer agents that can be used in combination with an HPTPβ-ECD binding agent disclosed herein, include but are not limited to, mitotic inhibitors (*vinca* alkaloids). These include vincristine, vinblastine, vindesine and Navelbine™ (vinorelbine-5'-noranhydroblastine). In yet other embodiments, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that may be used in the methods and compositions of the present disclosure are podophyllotoxin derivatives, such as etoposide, teniposide and mitopodozide. The present disclosure further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin and dacarbazine. The present disclosure encompasses antimetabolites as chemotherapeutic agents. Examples of these types of agents include cytosine arabinoside, fluorouracil, methotrexate, mercaptopurine, azathioprime and procarbazine. An additional category of chemotherapeutic cancer agents that may be used in the methods and compositions of the present disclosure include antibiotics. Examples include without limitation doxorubicin, bleomycin, dactinomycin, daunorubicin, mithramycin, mitomycin, mytomycin C and daunomycin. There are numerous liposomal formulations commercially available for these compounds. The present disclosure further encompasses other chemotherapeutic cancer agents including without limitation anti-tumor antibodies, dacarbazine, azacytidine, amsacrine, melphalan, VM-26, ifosfamide, taxol and its derivatives, L-asparaginase, mitoxantrone, IF-2, gemcitabine, erlotinib, doxil, irinortecan and bevacizumab.

Other anti-cancer agents that can be used in combination with the disclosed HPTPβ-ECD binding agent include, but are not limited to: acivicin, aclarubicin, acodazole hydrochloride, acronine, adozelesin, aldesleukin, altretamine, ambomycin, ametantrone acetate, aminoglutethimide, anastrozole, anthramycin, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, cactinomycin, calusterone, caracemide, carbetimer, carboplatin, carubicin hydrochloride, carzelesin, cedefingol, cirolemycin, cladribine, crisnatol mesylate, cytarabine, daunorubicin hydrochloride, decitabine, dexormaplatin, dezaguanine, dezaguanine mesylate, diaziquone, docetaxel, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide phosphate, etoprine, fadrozole hydrochloride, fazarabine, fenretinide, floxuridine, fludarabine phosphate, flurocitabine, fosquidone, fostriecin sodium, gemcitabine hydrochloride, hydroxyurea, idarubicin hydrochloride, ilmofosine, interleukin 2 (including recombinant interleukin 2, or rIL2), interferon alfa-2a, interferon alfa-2b, interferon alfa-n1, interferon alfa-n3, interferon beta-1a, interferon gamma-1b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, menogaril, methotrexate sodium, metoprine, meturedepa, mitindomide, mitocarcin, mitocromin, mitogillin, mitomalcin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uredepa, vapreotide, verteporfin, vinblastine sulfate, vincristine sulfate, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride. Other anti-cancer drugs include, but are not limited to: 20-epi-1,25 dihydroxyvitamin D3, 5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, anti-dorsalizing morphogenetic protein-1, antiandrogen, prostatic carcinoma, antiestrogen, antineoplaston, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, canarypox IL-2, capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexamethasone, dexifosfamide, dexrazoxane, dexverapamil, diaziquone, didemnin B, didox, diethylnorspermine, dihydro-5-azacytidine, dihydrotaxol, 9-, dioxamycin, diphenyl spiromustine, docetaxel, docosanol, dolasetron, doxifluridine, droloxifene, dronabinol, duocarmycin SA, ebselen, ecomustine, edelfosine, edrecolomab, eflornithine, elemene, emitefur, epirubicin, epristeride, estramustine analogue, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, iobenguane, iododoxorubicin, ipomeanol, 4-, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor-saporin, mofarotene, molgramostim, monoclonal antibody, human chorionic gonadotrophin, monophosphoryl lipid A+myobacterium cell wall sk, mopidamol, multiple drug resistance gene inhibitor, multiple tumor suppressor 1-based therapy, mustard anticancer agent, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, prednisone, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, RII retinamide, rogletimide, rohitukine, romurtide, roquinimex, rubiginone B 1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofiran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, tetrachlorodecaoxide, tetrazomine, thaliblastine, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene bichloride, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinxaltine, vitaxin, vorozole, zanoterone, zeniplatin, zilascorb, and zinostatin stimalamer. In one embodiment, the anti-cancer drug is 5-fluorouracil or leucovorin.

Anti-angiogenic agents are also useful in the treatment of cancer. Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including α and β) interleukin 12, retinoic acid, and tissue inhibitors of metalloproteinase-1 and metalloproteinase-2. (TIMP-1 and -2). Small molecules, including topoisomerases such as razoxane, a topoisomerase II inhibitor with anti-angiogenic activity, can also be used.

One embodiment of the disclosure is a method for treating a patient diagnosed with a carcinoma, comprising administering to the patient a composition comprising an effective amount of an HPTPβ-ECD binding agent. Yet another embodiment is a method for treating a patient diagnosed with a carcinoma, comprising administering to the patient a composition comprising an effective amount of an HPTPβ-ECD binding agent in combination with an effective amount of a chemotherapeutic agent, wherein the HPTPβ-ECD binding agent and chemotherapeutic agent are administered together or in any order.

One embodiment of the disclosure is a method for preventing or reducing metastasis in a patient diagnosed with a carcinoma, comprising administering to the patient a composition comprising an effective amount of an HPTPβ-ECD binding agent. Yet another embodiment is a method for preventing or reducing metastasis in a patient diagnosed with a carcinoma, comprising administering to the patient a composition comprising an effective amount of an HPTPβ-ECD binding agent in combination with an effective amount of a chemotherapeutic agent, wherein the HPTPβ-ECD binding agent and chemotherapeutic agent are administered together or in any order.

In yet another embodiment of the disclosure is a method for treating a patient diagnosed with a sarcoma, comprising administering to the patient a composition comprising an effective amount of an HPTPβ-ECD binding agent. Yet another embodiment is a method for treating a patient diagnosed with a sarcoma, comprising administering to the patient a composition comprising an effective amount of an HPTPβ-ECD binding agent in combination with an effective amount of a chemotherapeutic agent, wherein the HPTPβ-ECD binding agent and the chemotherapeutic agent are administered together or in any order.

Yet another embodiment of the disclosure is a method for preventing or reducing metastasis in a patient diagnosed with a sarcoma, comprising administering to the patient a composition comprising an effective amount of an HPTPβ-ECD binding agent. Yet another embodiment is a method for preventing or reducing metastasis in a patient diagnosed with a sarcoma, comprising administering to the patient a composition comprising an effective amount of an HPTPβ-ECD binding agent in combination with an effective amount of one or more chemotherapeutic agent, wherein the HPTPβ-ECD binding agent and one or more chemotherapeutic agent are administered together or in any order.

Yet another embodiment of the disclosure is a method for treating a patient diagnosed with pancreatic cancer, comprising administering to the patient a composition comprising an effective amount of an HPTPβ-ECD binding agent. Still another embodiment is a method for treating a patient diagnosed with pancreatic cancer, comprising administering to the patient a composition comprising an effective amount of an HPTPβ-ECD binding agent in combination with an effective amount of one or more chemotherapeutic agents, wherein the HPTPβ-ECD binding agent and one or more chemotherapeutic agents are administered together or in any order.

Yet another embodiment of the disclosure is a method for preventing or reducing metastasis in a patient diagnosed with pancreatic cancer, comprising administering to the patient a composition comprising an effective amount of an HPTPβ-ECD binding agent. Still another embodiment is a method for preventing or reducing metastasis in a patient diagnosed with pancreatic cancer, comprising administering to the patient a composition comprising an effective amount of an HPTPβ-ECD binding agent in combination with an effective amount of one or more chemotherapeutic agent, wherein the HPTPβ-ECD binding agent and one or more chemotherapeutic agents are administered together or in any order.

In some embodiments the chemotherapeutic agent used in the treatment of pancreatic cancer is gemcitabine, or 5-flourouracil, or cisplatin or capecitabine, or oxaliplatin, or mitomycin, or any combination thereof.

Still another embodiment is a method for treating a patient diagnosed with malignant melanoma, comprising administering to the patient a composition comprising an effective amount of an HPTPβ-ECD binding agent. Yet another embodiment is a method for treating a patient diagnosed with metastatic melanoma, comprising administering to the patient a composition comprising an effective amount of an HPTPβ-ECD binding agent in combination with an effective amount of one or more chemotherapeutic agent, wherein the HPTPβ-ECD binding agent and one or more chemotherapeutic agents are administered together or in any order.

Still another embodiment is a method for preventing or reducing metastasis in a patient diagnosed with malignant melanoma, comprising administering to the patient a composition comprising an effective amount of an HPTPβ-ECD binding agent. Yet another embodiment is a method for preventing or reducing metastasis in a patient diagnosed with metastatic melanoma, comprising administering to the patient a composition comprising an effective amount of an HPTPβ-ECD binding agent in combination with an effective amount of one or more chemotherapeutic agent, wherein the HPTPβ-ECD binding agent and one or more chemotherapeutic agents are administered together or in any order.

In some embodiments the chemotherapeutic agent is used to treat melanoma is cisplatin, or vinblastine, or dacarbazine, or any combination thereof.

Still another embodiment is a method for treating a patient diagnosed with breast cancer comprising administering to the patient a composition comprising an effective amount of an HPTPβ-ECD binding agent. Yet another embodiment is a method for treating a patient diagnosed with breast cancer comprising administering to the patient a composition comprising an effective amount of an HPTPβ-ECD binding agent in combination with an effective amount of one or more chemotherapeutic agent, wherein the HPTPβ-ECD binding agent and one or more chemotherapeutic agents are administered together or in any order. Yet another embodiment is a method for preventing or reducing metastasis in a patient diagnosed with breast cancer comprising administering to the patient a composition comprising an effective amount of an HPTPβ-ECD binding agent. Yet another embodiment is a method for preventing or reducing metastasis in a patient diagnosed with breast cancer comprising administering to the patient a composition comprising an effective amount of an HPTPβ-ECD binding agent in combination with an effective amount of one or more chemotherapeutic agent, wherein the HPTPβ-ECD binding agent and one or more chemotherapeutic agent are administered together or in any order. In some embodiments the chemotherapeutic agent is used in the treatment of breast cancer is taxol or an analog of taxol.

In particular embodiments the HPTPβ-ECD binding agent is administered in combination with IL-2.

IL-2 Induced Vascular Leak: Treatment of Metastatic Cancers

Immunotherapy is one method of treating cancer. Up-regulation of the body's own immune system is one aspect of immunotherapy. Among the many immune system signaling molecules is interleukin-2 (IL-2) which is instrumental in the body's natural response to microbial infection and in discriminating between foreign (non-self) and self. High-dose interleukin-2 is an FDA approved treatment for patients with metastatic renal cell carcinoma and metastatic melanoma. Although it has been reported that only 23% of those subjects given this therapy show a tumor response, the duration of this response can exceed 10 years (Elias L. et al., "A literature analysis of prognostic factors for response and quality of response of patients with renal cell carcinoma to interleukin-2-based therapy." Oncology, (2001), Vol. 61, pp. 91-101). As such, IL-2 therapy is the only available treatment that offers the potential for cure.

Gallagher (Gallagher, D. C. et al., "Angiopoietin 2 Is a Potential Mediator of High-Dose Interleukin 2-Induced Vascular Leak" Clin. Cancer Res., (2007), Vol. 13, No. 7, pp. 2115-2120) reports that elevated levels of angiopoietin-2 are found in patients treated with high doses of IL-2 and suggests that overcoming Ang-2 blockade of Tie-2 signaling might be curative for vascular leak syndrome which is a side effect of this therapy.

IL-2 is known to cause endothelial cell activation, however, with loss of proper barrier function. Amplification of Tie-2 signaling during high dose IL-2 immunotherapy would lead to attenuation of vascular leakage since Tie-2 stimulation promotes endothelial cell stability. As such, by administering an agent that can amplify Tie-2 signaling, vascular stability can be increased and, hence, the side effects of high IL-2 dosing mitigated. The disclosed HPTPβ-ECD binding agents can amplify Tie-2 signaling under the conditions of low angiopoietin-1 concentrations or when high concentrations of angiopoietin-2 are present as in IL-2 treated patients.

By amplifying Tie-2 signaling without affecting Ang-2 levels, the use of elevated levels of Ang-2 as a potential pathology marker is retained. For example, a patient suffering from an inflammatory disease such as sepsis will normally have an elevated Ang-2 level that acts to suppress Ang-1 stimulation of Tie-2. This elevated Ang-2 results in edema which is a symptom of vascular leakage. The present methods, by amplifying Tie-2 signaling without affecting the Ang-2 level, provide a method for alleviating the symptoms that are associated with vascular leak while retaining the ability to use Ang-2 levels as a measure of disease progress and resolution.

As many as 65% of patients receiving this IL-2 therapy will necessarily interrupt or discontinue treatment due to VLS. The major dose-limiting toxicity of interleukin-2 (IL-2) and of immunotoxin (IT) therapies is vascular leak syndrome (VLS). VLS is characterized by an increase in vascular permeability accompanied by extravasation of fluids and proteins resulting in interstitial edema and organ failure. Manifestations of VLS include fluid retention, hypotension, increase in body weight, peripheral edema, pulmonary edema, pleural and pericardial effusions, ascites, anasarca and, in severe form, signs of pulmonary and cardiovascular failure.

The disclosed HPTPβ-ECD binding agents can be used as an effective therapy to reduce vascular leak caused by treatment with IL-2. Therefore an embodiment of the present invention is a method of treating, reducing or preventing vascular leak in a patient being administered IL-2 wherein the method comprises administering to the patient a composition comprising an effective amount of an HPTPβ-ECD binding agent. The HPTPβ-ECD binding agent can be co-administered with IL-2 or administered separately. The IL-2 and the HPTPβ-ECD binding agent may be administered in any order and by any method, for example, intravenously, orally, by patch, subcutaneous injection and the like.

One embodiment of the present disclosure is a method for treating renal cell carcinoma comprising administering to a patient a composition comprising: a) an effective amount of interleukin-2 such that an immune response is provided; and b) an effective amount of an HPTPβ-ECD binding agent; wherein the interleukin-2 and the HPTPβ-ECD binding agent can be administered together or in any order. Another embodiment disclosed herein is a method for treating renal cell carcinoma comprising administering to a patient a composition comprising: a) a high dose of interleukin-2; and b) an effective amount of an HPTPβ-ECD binding agent.

Further disclosed is a method for treating metastatic melanoma comprising administering to a patient a series of compositions, wherein the compositions can be administered in any order and at any effective amount, a first composition comprising, a high dose of interleukin-2 and the second composition comprising an effective amount of an HPTPβ-ECD binding agent.

Still further disclosed is a method for treating renal cell carcinoma comprising administering to a patient a series of compositions, wherein the compositions can be administered in any order and at any effective amount, a first composition comprising a high dose of interleukin-2 and the second composition comprising an effective amount of an HPTPβ-ECD binding agent.

Disclosed herein is a method for treating metastatic melanoma by administering to a patient in need of treatment a therapy that comprises: a) an effective amount of interleukin-2 such that an immune response is provided; and b) an effective amount of an HPTPβ-ECD binding agent; wherein the interleukin-2 and the HPTPβ-ECD binding agent can be administered together or in any order.

Also disclosed herein is a method for treating metastatic melanoma by administering to a patient in need of treatment a therapy that comprises: a) an effective amount of interleukin-2 such that an immune response is provided; and b) an effective amount of an HPTPβ-ECD binding agent; wherein the interleukin-2 and the HPTPβ-ECD binding agent can be administered together or in any order.

Disclosed herein are compositions which can be used to treat patients with cancer, wherein the patient having cancer is treated with one or more cancer agents that induce vascular leak syndrome in the patient. As such, disclosed herein are compositions effective in reducing vascular leak resulting from a cancer treatment, the compositions comprising an effective amount of an HPTPβ-ECD binding agent.

Another aspect disclosed herein are compositions effective for treating humans or other mammals having a medical condition or disease state wherein the treatment for the medical condition or disease state induces vascular leak syndrome, the composition comprising: a) an effective amount of an HPTPβ-ECD binding agent; and b) one or more pharmaceutical drugs; wherein at least one of the pharmaceutical drugs induces vascular leak syndrome.

In a further aspect, disclosed herein are compositions comprising: a) an effective amount of an HPTPβ-ECD binding agent; and b) one or more chemotherapeutic agent.

Also disclosed herein are compositions which can be used to control vascular leakage, the compositions comprising an effective amount of one or more of the agents disclosed herein. Still further disclosed herein are compositions which can be used to treat patients with an inflammatory disease, non-limiting examples of which include sepsis, lupus, and inflammatory bowel disease, the compositions comprising an effective amount of an HPTPβ-ECD binding agents disclosed herein. The HPTPβ-ECD binding agents inhibit the Tie2 dephosphorylase activity of HPTPβ acting as Tie-2 signaling amplifiers.

Tumor growth is often a multi-step process that starts with the loss of control of cell proliferation. The cancerous cell then begins to divide rapidly, resulting in a microscopically small, spheroid tumor: an in situ carcinoma. As the tumor mass grows, the cells will find themselves further and further away from the nearest capillary. Finally the tumor stops growing and reaches a steady state, in which the number of proliferating cells counterbalances the number of dying cells. The restriction in size is caused by the lack of nutrients and oxygen. In tissues, the oxygen diffusion limit corresponds to a distance of 100 μm between the capillary and the cells, which is in the range of 3-5 lines of cells around a single vessel. In situ carcinomas may remain dormant and undetected for many years and metastasis are rarely associated with these small (2 to 3 $mm^2$), avascular tumors.

When a tumor's growth is stopped due to a lack of nutrients and/or oxygen, this reduction in tumor vasculature also limits the ability of anti-tumor drugs to be delivered to the malignant cells. Moreover, if there is a slight increase in tumor vasculature, this will allow delivery of anti-tumor therapies to the malignant cells without initiating metastasis. As such, the disclosed agents when used to slightly amplify Tie-2 signaling can be used to increase blood flow to the tumor cells without setting off metastasis or uncontrolled tumor cell proliferation while providing a method for delivering anti-cancer drugs to malignant cells.

Disclosed herein, is a method for treating cancer comprising administering to a patient in need an effective amount of an HPTPβ-ECD binding agent in conjunction with one or more chemotherapeutic compound or immunotherapeutic compound. To "slightly amplify Tie-2 signaling" means that a sufficient amount of a disclosed compound is administered to a patient such that the amount of tumor cell vasculature is increased such that the increased circulation allows for delivery of the anti-tumor compound or therapy without instigating tumor growth wherein the rate of tumor cell growth is less than the rate of tumor cell death. It is recognized that amplifying Tie2 signaling would stabilize the tumor vasculature making it resistant to angiogenic signals reducing tumor angiogenesis and tumor growth while improving tumor blood flow and the delivery of chemotherapeutic agents.

Angiopoietin-2 is significantly correlated to Gleason Score, metastasis and to cancer specific survival (Lind A. J. et al., "Angiopoietin-2 expression is related to histological grade, vascular density, metastasis and outcome in prostate cancer" Prostate, (2005), Vol. 62, pp. 394-299). Angiopoietin-2 was found to be expressed in prostate cancer bone, liver and lymph node metastasis, but with little to no angiopoietin-1 expression in prostate cancer tumor cells in bone, liver and lymph nodes (Morrissey C. et al., "Differential expression of angiogenesis associated genes in prostate cancer bone, live and lymph node metastasis" Clin. Exp. Metastasis, (2008), Vol. 25, pp. 377-388). As such, monitoring the level of Ang-2 provides a method for evaluating the presence of prostate cancer and the spread of prostate cancer cells throughout the body due to vascular leakage.

Thus, another embodiment of the disclosure is a method of evaluating efficacy of treatment comprising monitoring the Ang-2 level of the patient while the patient is undergoing treatment.

Vasculature Stabilization in Diseases Caused by Pathogens

Disclosed herein is a method for preventing or treating vascular leak syndrome caused by one or more pathogens, comprising administering to a human or other mammal in need of treatment an effective amount of one or more HPTPβ-ECD binding agent.

One embodiment is a method for treating vascular leak syndrome caused by one or more pathogens, comprising administering to a human or other mammal in need of treatment a composition comprising: a) an effective amount of one or more compounds effective against a pathogen present in the human or mammal; and b) an effective amount of an HPTPβ-ECD binding agent; wherein the one or more compounds effective against a pathogen and the HPTPβ-ECD binding agent can be administered together or in any order.

Further disclosed is a method for preventing vascular leak syndrome in a human or other mammal diagnosed with a pathogen infection that can produce vascular leak syndrome in a human or mammal, comprising administering to a human or mammal a composition comprising: a) an effective amount of one or more compounds effective against a pathogen present in the human or mammal; and b) an effective amount of one or more HPTPβ-ECD binding agent; wherein the one or more compounds effective against a pathogen and the one or more HPTPβ-ECD binding agent can be administered together or in any order.

The following are non-limiting examples of viruses, bacteria and other pathogens where virulence can be controlled by mitigating the degree of vascular leak that is induced by the organism. *Staphylococcus aureus, Bacillus anthracis, Pseudomonas, Streptococcus pyogenes*, and dengue virus.

One embodiment is a method for treating vascular leak syndrome in a patient suffering from a bacterial infection by administering to the patient a composition comprising an effective amount of an HPTPβ-ECD binding agent. Further disclosed is a method for preventing vascular leak syndrome in a human or other mammal diagnosed with a bacterial infection.

Thus one embodiment of the present disclosure is a method of treating a patient suffering from a bacterial infection by administering to the patient a composition comprising an effective amount of an HPTPβ-ECD binding agent. In particular embodiments the bacterial infection is a *Bacillus anthracis* infection. In other embodiments the bacterial infection is a *Pseudomonas* infection. In yet other embodiments the bacterial infection is a *Streptococcus pyogenes* infection.

One embodiment is a method for treating vascular leak syndrome in a patient suffering from a viral infection by administering to the patient a composition comprising an effective amount of an HPTPβ-ECD binding agent. Further disclosed is a method for preventing vascular leak syndrome in a human or other mammal diagnosed with a viral infection.

Another embodiment is a method of treating a patient suffering from a viral infection by administering to the patient a composition comprising an effective amount of an HPTPβ-ECD binding agent. In particular embodiments the viral infection is a dengue virus infection.

The HPTPβ-ECD binding agent may be administered in combination with one or more antibacterial or antiviral agent wherein the HPTPβ-ECD binding agent and the antiviral or antibacterial agents can be administered together or in any order. Thus, an embodiment of the present disclosure is a method of treating a patient suffering from a bacterial infection comprising administering: a) an HPTPβ-ECD binding agent; and b) one or more antibacterial agents, wherein the HPTPβ-ECD binding agent and antibacterial agent can be administered together or in any order. Another embodiment of the present disclosure is a method of treating a patient suffering from a viral infection comprising administering: a) an HPTPβ-ECD binding agent; and b) one or more antiviral agents wherein the HPTPβ-ECD binding agent and antiviral agent can be administered together or in any order.

Another method provided by the present disclosure, is a method for determining the course of treatment for a patient suffering from vascular leak syndrome, comprising: a) administering to a patient a composition comprising an effective amount of an HPTPβ-ECD binding agent; b) monitoring the level of angiopoietin-2 present in the patient during the course of treatment; and c) discontinuing treatment when the angiopoietin-2 level returns to within a normal range.

A further aspect relates to methods of treating vascular leak in a patient infected with anthrax comprising administering a composition comprising an effective amount of an HPTPβ-ECD binding agent in combination with an effective amount of one or more antibacterial agents effective against anthrax, wherein the HPTPβ-ECD binding agent and the antibacterial agents effective against anthrax are administered together or in any order.

Yet another aspect relates to methods of treating vascular leak in a patient infected with a virus comprising administering a composition comprising an effective amount of an HPTPβ-ECD binding agent in combination with an effective amount of one or more antiviral agents, wherein the HPTPβ-ECD binding agent and the antiviral agent are administered together or in any order.

Increased amplification of Tie-2 signaling using the disclosed agents provides a method for stabilizing vasculature without the need to affect Ang-1 and/or Ang-2 levels. Disclosed herein are methods for stabilizing vasculature, comprising administering to a patient an effective amount of an HPTPβ-ECD binding agents.

Because the disclosed agents can amplify Tie-2 signaling without increasing the amount of Ang-2, monitoring the amount of Ang-2 in blood serum of a patient while administering to a patient an HPTPβ-ECD binding agent, serves as a method for determining the course of various illnesses or disease states associated with vascular leak syndrome, for example, sepsis as a result of infection. As such, disclosed is a method for stabilizing vasculature in a patient suffering from an inflammatory disease wherein the level of angiopoietin-2 is elevated, comprising: a) administering to a patient an effective amount of an HPTPβ-ECD binding agent; b) monitoring the level of angiopoietin-2 present in the patient; and c) discontinuing treatment when the angiopoietin-2 level returns to a normal range.

What is meant herein by "normal angiopoietin-2 level" is an amount of Ang-2 in blood serum of from about 1 ng/mL to about 2 ng/mL. Alternatively, the level of Ang-2 can be determined for an individual suffering from a disease state, for example, severe sepsis and the level of Ang-2 can be monitored until the amount of Ang-2 in the patient's serum drop to a level that is nearer the normal range. In this case, the co-administration of a drug can be continued or discontinued.

Therefore, disclosed herein is a method for stabilizing the vasculature of a patient during a course of treatment, comprising: a) co-administering to a patient an effective amount of an HPTPβ-ECD binding agent and one or more drugs as a treatment; b) monitoring the level of angiopoietin-2 present in the patient; and c) discontinuing the administration of the one or more drugs, and selecting one or more other drugs for use as a treatment if the level of serum angiopoetin-2 does not decrease.

The HPTPβ-ECD binding agent, while stabilizing the vasculature of a patient such that a course of treatment against a pathogen can be sustained, can also be used to stabilize a patient during a period wherein an effective treatment against a pathogen is being determined. That is, the HPTPβ-ECD binding agents by themselves can have a beneficial effect on the outcome of diseases caused by pathogens by reducing vascular leak and its complications.

Any of the foregoing compositions comprising an HPTPβ-ECD binding agent are suitable for use in the manufacture of a medicament for treatment of any of the diseases or disorder described above. In addition, any of the foregoing compositions comprising an HPTPβ-ECD binding agent are suitable for use in treating any of the diseases or disorder described above.

In Vivo Vascular Leak

The Miles assay (Miles, A. A. and E. M. Miles (1952) Vascular reactions to histamine, histamine-liberator and leukotaxine in the skin of guinea-pigs. J. Physiol., Vol. 118, pp. 228-257 incorporated herein by reference in its entirety) can be used to directly investigate and quantify lethal toxin, as well as edema toxin (ET [PA plus EF])-mediated vascular leakage in the mouse model. The following is a modified Miles assay as described by Gozes Y. et al., Anthrax Lethal Toxin Induces Ketotifen-Sensitive Intradermal Vascular Leakage in Certain Inbred Mice Infect. Immun., 2006 February, Vol. 74, No. 2, pp. 1266-1272 incorporated herein by reference in its entirety, that can be used to evaluate the disclosed HPTPβ-ECD binding agents for their ability to prevent vascular leakage in humans and animals exposed to anthrax.

Highly pure PA, LF, and mutant LF E687C are purified as previously described (Varughese M. et al., (1998) Internalization of a *Bacillus anthracis* protective antigen-c-Myc fusion protein mediated by cell surface anti-c-Myc antibodies. Mol. Med. 4:87-95 included herein by reference in its entirety). Doses of ET or LT refer to the amount of each component (i.e., 100 μg LT is 100 μg PA plus 100 μg of LF). All drugs except for azelastine can be purchased from Sigma Aldrich (St. Louis, Mo.); azelastine can be purchased from LKT Laboratories (St. Paul, Minn.). LT is an abbreviation for lethal toxin; PA is an abbreviation for protective antigen; LF is an abbreviation for lethal factor; and EP is an abbreviation for edema factor.

Animals.

BALB/cJ, DBA/2J, C3H/HeJ, C3H/HeOuJ, WBB6F1/J-$Kit^{W}/Kit^{W-v}$, and colony-matched wild-type homozygous control mice can be purchased from The Jackson Laboratory (Bar Harbor, Me.). BALB/c nude, C57BL/6J nude, and C3H hairless (C3.Cg/TifBomTac-hr) mice can be purchased from Taconic Farms (Germantown, N.Y.). C3H nude mice can be purchased from The National Cancer Institute Animal Production Area (Frederick, Md.). Mice are used when they are 8 to 12 weeks old. Except for C3H hairless and nude animals, all mice are shaved 24 hours prior to intradermal (i.d.) injections. In order to assess the susceptibility to systemic LT, mice are injected intraperitoneally (i.p.) with 100 m LT and observed over 5 days for signs of malaise or death. Fischer 344 rats can be purchased from Taconic Farms (Germantown, N.Y.) and used at weights of 150 to 180 g. Rats are injected intravenously (i.v.) in the tail vein with 12 μg LT, with or without 250 m of the mast cell stabilizer drug ketotifen and monitored for the exact time to death.

Miles Assay.

The Miles assay uses i.v. injection of Evans blue dye (which binds to endogenous serum albumin) as a tracer to assay macromolecular leakage from peripheral vessels after i.d. injection of test substances. Nude mice and normal shaved mice are injected i.v. with 200 μl of 0.1% Evans blue dye (Sigma Chemical Co., St. Louis, Mo.). After 10 min, 30 μl of test toxin or control samples (PA only, LF only, EF only, or phosphate-buffered saline) are injected i.d. in both left and right flanks, as well as at single or dual dorsal sites. To quantify the extents of leakage, equally sized (1.0- to 1.5-cm diameter) skin regions surrounding i.d. injection sites are removed 60 min after injection and placed in formamide (1 ml) at 41° C. for 48 h, allowing for dye extraction. The $A_{620}$ of samples is read, and the extent of leakage is calculated by comparison with phosphate-buffered saline-, PA-, or LF-treated controls.

In experiments wherein the effectiveness of the HPTPβ-ECD binding agents are tested for LT-mediated leakage, mice are injected i.v. with Evans blue as described above, and the test agent introduced systemically through i.p. injection 10 min after dye injection. LT was introduced by i.d. injection 30 min after the injection of Evans blue. In another embodiment, the agent to be tested can be introduced locally by i.d. injection and LT injected in the same site after 10 min.

Cytotoxicity Experiments.

MC/9 mast cells can be obtained from ATCC (Manassas, Va.) and grown in Dulbecco's modified Eagle's medium supplemented with 1-glutamine (2 mM), 2-mercaptoethanol (0.05 mM), Rat T-STIM (BD Biosciences-Discovery Labware, Bedford, Mass.) (10%), and fetal bovine serum (FBS, 10% final concentration; Invitrogen-GIBCO BRL, Gaithersburg, Md.). Cells are then seeded at a density of $10^4$/well in 96-well plates prior to treatment with various LT concentrations or PA-only controls. After 6, 12, and 24 hours, viability is assessed using Promega's CellTiter 96 $AQ_{ueous}$ One Solution cell proliferation assay (Promega, Madison, Wis.) per the manufacturer's protocol. Alternatively, toxicity assays can be performed in medium provided with all supplements except FBS (serum-free medium). In other embodiments, pooled human umbilical vein endothelial cells (HUVECs) at third to fifth passage can be obtained from Cambrex Corp. (Cambrex, Walkersville, Md.) and grown in an EGM-MV Bulletkit (Cambrex, Walkersville, Md.) in flasks pretreated with endothelial cell attachment factor (Sigma, St. Louis, Mo.). For cytotoxicity experiments, cells are typically seeded in 96-well plates in an EGM-MV Bulletkit. On the day of assays, this medium is then replaced with M199 medium (Sigma, St. Louis, Mo.) supplemented with 10% FBS or human serum (Sigma, St. Louis, Mo.), and cells are reseeded in 96-well plates at a density of $2 \times 10^3/0.1$ ml/well and treated with various concentrations of LT in triplicate. Cell viability is typically assessed as for MC/9 cells at 24, 48 and 72 hour time points.

HUVEC Permeability Assay

HUVEC monolayers can be effectively cultured on Transwell-Clear cell culture inserts (6.5-mm diameter, 0.4-µm pore size; Corning-Costar, Acton, Mass.) in 24-well plates, creating a two-chamber culturing system consisting of a luminal compartment (inside the insert) and a subluminal compartment (the tissue culture plate well). Prior to seeding cells, the inserts are coated with endothelial cell attachment factor (Sigma, St. Louis, Mo.). Pre-warmed CS-C medium (Sigma, St. Louis, Mo.) containing 10% iron-supplemented calf serum and 1% endothelial cell growth factor (Sigma, St. Louis, Mo.) is added to wells prior to insert placement. A HUVEC cell suspension (200 µL of $5 \times 10^5$ cells/ml) is then added to each insert. Cells are cultured at 37° C. in 5% $CO_2$ for up to 21 days to ensure proper formation of a monolayer. For testing barrier function, medium can be changed to RPMI supplemented with 10% FBS or to RPMI without serum. To assess barrier function, horseradish peroxidase enzyme (Sigma, St. Louis, Mo.) is added to the inserts (10 µg/well). LT (1 µg/mL) or control treatments of PA alone (1 µg/mL) or LF alone (1 µg/mL) are added to duplicate wells, and every hour (for 12 hours), a sample of 10 µL was taken from the subluminal compartment and tested for the enzymatic activity of horseradish peroxidase by adding 100 µL substrate [2',2'-azino-bis(3-ethylbenzthizolin 6-sulfonic acid)] (A-3219; Sigma, St. Louis, Mo.) and reading at 405 nm.

Anthrax Combination Therapy

Increased stabilization of vascular tissue can increase the effectiveness of known antimicrobials against anthrax infection. As such, HPTPβ-ECD binding agents can be evaluated as a combination therapy for the treatment of anthrax. The following describes a series of assays that can be used to determine the effectiveness of an HPTPβ-ECD binding agent as one part of a combination therapy useful for treating anthrax infections.

LF has been found to cleave mitogen-activated protein kinase kinases (MAPKK), disrupts signal transduction, and leads to macrophage lysis. As such, in addition to the Miles Assay, the following cell-based and peptide cleavage assay can be used to confirm the potency of the HPTPβ-ECD binding agents to inhibit the effect of LT activity. For the following assay, MAPKKide can be purchased from List Biological Laboratories (Campbell, Calif. Fluorinated peptide substrate is available from Anaspec (San Jose, Calif.).

In Vivo Assays

One week before beginning an evaluation of a combination course of treatment for anthrax, test agents (200 mg each) are dissolved in 800 µL of DMSO and stored at −20° C. Immediately before injection, each test agent is diluted in PBS, resulting in a final concentration of 0.5 mg/mL in 2% DMSO. Test animal are challenged on day 0 with $2 \times 10^7$ spores per mouse in PBS through i.p. injection. Treatment was started 24 hours after challenge. One example of a suitable treatment regimen is the combination of ciprofloxacin (50 mg/kg) and an HPTPβ-ECD binding agent (5 mg/kg). A control sample of untreated animals, ciprofloxacin alone, a disclosed agent alone and ciprofloxacin in combination with a disclosed agent are given to the animals and they are monitored twice per day until day 14 after injection.

Ciprofloxacin and the agent to be tested can be conveniently administered through parenteral injection with a volume of 200 µL for each once per day for 10 days. All surviving animals are sacrificed on day 14. Sick animals that appear moribund (i.e., exhibiting a severely reduced or absent activity or locomotion level, an unresponsiveness to external stimuli, or an inability to obtain readily available food or water, along with any of the following accompanying signs: ruffled haircoat, hunched posture, inability to maintain normal body temperature, signs of hypothermia, respiratory distress, or other severely debilitating condition) should be sacrificed on the same day these symptoms are manifested.

Modulation of Bacterium-Induced Vascular Leak

Pathogenic bacteria are known to cause vascular leak. This induced vascular leakage inhibits the ability of antimicrobials and other pharmaceuticals from targeting the invading microorganism. As such, HPTPβ-ECD binding agents can be used alone or in combination with other pharmaceutical ingredients to boost the host immune system by preventing excess vascular leakage that occurs as a result of a bacterial infection.

The following describe tests and assays that can be used to determine the effectiveness of an HPTPβ-ECD binding agent, either alone, or a combination therapy.

*Staphylococcus aureus* (*S. aureus*) is a major pathogen of gram-positive septic shock and is associated with consumption of plasma kininogen. The effect of an HPTPβ-ECD binding agent on *S. aureus* induced vascular leakage activity can be determined by measuring the activity of these agents with respect to two cysteine proteinases that are secreted by *S. aureus*. Proteolytically active staphopain A (ScpA) induces vascular leakage in a bradykinin (BK) $B_2$-receptor-dependent manner in guinea pig skin. This effect is augmented by staphopain B (SspB), which, by itself, had no vascular leakage activity. ScpA also produces vascular leakage activity from human plasma.

An important pathophysiologic mechanism of septic shock is hypovolemic hypotension that is caused by plasma leakage into the extravascular space. It has been found that ScpA induced vascular leakage at a concentration as low as 20 nM within 5 minute after injection into the guinea pig skin—with the reaction being augmented by coexisting SspB indicating that vascular leakage induction by these proteinases occurs efficiently in vivo (Imamura T. et al., Induction of vascular leakage through release of bradykinin and a novel kinin by cysteine proteinases from *Staphylococcus aureus* (2005) J. Experimental Medicine, Vol. 201, No. 10, pp. 1669-1676).

Vascular Leakage Assay.

Animals can be evaluated for vascular leakage using the following procedure. 100 µL of a 1% solution of Evans blue dye (Sigma Aldrich) in saline is injected into the tail vein. Thirty minutes later, mice are sacrificed and perfused with saline via the right ventricle to remove intravascular Evans blue. Lungs are excised and extracted in 1 mL of formamide at 55° C. overnight. Evans blue content is determined as $OD_{620}$ minus $OD_{500}$ of the formamide extract.

The agents disclosed herein can be used as a single pharmaceutical therapy to reduce the severity of influenza by mediating the effects of vascular leak caused by viruses, and, hence, allowing the body's own immune system to affect greater resistance to these pathogens. The following assays can be used to determine the effect of an HPTPβ-ECD binding agent to inhibit viral severity because of improved vascular integrity.

The disclosed assays can use inhibition of viral plaques, viral cytopathic effect (CPE), and viral hemagglutitin.

Proteolytic Sensitivity Assay

An HPTPβ-ECD binding agent can be determined to bind to hemagglutinin and thereby destabilize the protein assembly. The following procedure can be used to determine the increase in destabilization and therefore the increased sensitivity of hemagglutinin to proteolytic attack caused by an HPTPβ-ECD binding agent. At the fusion conformation, HA becomes more sensitive to protease digestion. This property can be used to verify if a fusion inhibitor interacts with HA (Luo G. et al., "Molecular mechanism underlying the action of a novel fusion inhibitor of influenza A virus." J. Virol., (1997), Vol. 71, No. 5, pp. 4062-4070). Thus, an HPTPβ-ECD binding agent, due to the control of vascular leakage, can be evaluated for its ability to indirectly effect HA digestion by enhancing the body's immune response.

The purified trimer of hemagglutinin ectodomain is incubated with the agent to be tested at a concentration of 5 μM. The trimers are subjected to trypsin digestion at pH 7.0 and pH 5.0 with controls of untreated HA and HA treated with DMSO which is the solvent used to dissolve the test agent. For the pH 5.0 sample, the HA trimers are treated with a pH 5.0 buffer for 15 minutes and neutralized to pH 7.0. Trypsin (20 ng) is added to the sample in 10 μL and the digestion allowed to proceed for 1 hour at 37° C., The amount of HA present is assessed by a western blot gel electrophoresis using anti-HA (H3) antisera. Samples containing effective inhibitors will provide an increase in digestion of HA by trypsin.

In addition, combination therapies can provide a method for treating influenza by providing an antiviral medication together with an agent that prevents the severity of vascular leakage due to influenza viruses.

An antiviral compound, for example, oseltamivir, can be used for an in vivo evaluation of the disclosed combination therapy and to evaluate the effectiveness of an HPTPβ-ECD binding agent. The drug combination is administered in a single dose to mice infected with the influenza A/NWS/(H1N1) virus. In some instances, infection of the animals will include multiple passage of the virus through their lungs. One convenient protocol involves administering 20 mg/kg per day twice daily for 5 days beginning 4 hours prior to virus exposure. The animals are then challenged with different concentrations of virus, ranging 10-fold from $10^{-2}$ ($10^{5.75}$ cell culture 50% infectious doses ($CCID_{50}$) per mL). Four mice in each group are sacrificed on day 6 and their lungs removed, assigned a consolidation score ranging from 0 (normal) to 4 (maximal plum coloration), weighted, homogenized, the homogenates centrifuged at 2000×g for 10 minutes, and varying 10-fold dilutions of the supernatant assayed for virus titer in MDCK cells using CPE produced after a 96-hour incubation at 37° C. as endpoint.

The serum taken from mice on day 6 is assayed for $a_1$-AG using single radial immunodiffusion kites. Eight additional mice in each group are continually observed daily for death for 21 days, and their arterial oxygen saturation ($SaO_2$) values determined by pulse oximetry (Sidwell R. et al., (1992) Utilization of pulse oximetry for the study of the inhibitory effects of antiviral agents on influenza virus in mice. Antimicrob. Agents Chemother. 36, 473-476) on day 3, when $SaO_2$ decline usually begins to occur, through day 11, when the values are seen to decline to the maximum degree of the animals otherwise die.

Inhibition of Protein Tyrosine Phosphatase Beta in a Cell

Disclosed herein are methods for inhibiting protein tyrosine phosphatase beta (HPTP-β) activity in a cell, comprising contacting a cell with an effective amount of an HPTPβ-ECD binding agents. The cell can be contacted in vivo, ex vivo, or in vitro.

Administration

Depending on the nature of the particular agent, agents of the present disclosure can be administered to humans and other animal, parenterally, (e.g., by intravenous or intraperitoneal injection), subcutaneously, orally, topically, rectally, buccally, as an oral or nasal spray.

The HPTPβ-ECD binding agents of the disclosure are preferably formulated in dosage unit form for ease of administration and uniformity of dosage. The expression "dose" or "dosage unit form" as used herein refers to a physically discrete unit of agent appropriate for the patient to be treated. It will be understood, however, that the total daily usage of the HPTPβ-ECD binding agents and compositions of the present invention will be decided by the attending physician within the scope of sound medical judgment.

Dosing

Effective dosages and schedules for administering the HPTPβ-ECD binding agent may be determined empirically, and making such determinations is within the skill in the art. Those skilled in the art will understand that the dosage of the agent that must be administered will vary depending on, for example, the subject which will receive the agent, the route of administration, the particular type of agent used and other drugs being administered to the subject. For example, guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical dose of the agent used alone might range from about 0.01 mg/kg to up to 500 mg/kg of body weight or more per day, or from about 0.01 mg/kg to about 50 mg/kg, or from 0.1 mg/kg to about 50 mg/kg, or from about 0.1 mg/kg to up to about 10 mg/kg, or from about 0.2 mg/kg to about 1 mg/kg, or from about 1 mg/kg to about depending on the factors mentioned above.

The dosing schedules for administration of an HPTPβ-ECD binding agent include, but are not limited to, once daily, three-times weekly, twice weekly, once weekly, three times, twice monthly, once monthly and once every other month.

Formulations

In one aspect of the present invention, pharmaceutically acceptable compositions are provided, wherein these compositions comprise any of the agents as described herein, and a pharmaceutically acceptable carrier and, in addition, can include other pharmaceutical agents, adjuvants or diluents. For example, pharmaceutical compositions can also include one or more additional active ingredients such as antimicrobial agents, anti-inflammatory agents, anesthetics and the like.

The formulation may vary depending on the mode of administration. The pharmaceutical compositions can be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage.

For the purposes of the present disclosure the term "excipient" and "carrier" are used interchangeably throughout the description of the present disclosure and said terms are defined herein as, "ingredients which are used in the practice of formulating a safe and effective pharmaceutical composition." The formulator will understand that excipients are used primarily to serve in delivering a safe, stable and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients.

"Pharmaceutically acceptable" means a material that is not biologically or otherwise undesirable, i.e., the material may be administered to a patient without causing any undesirable biological effects or interacting in a deleterious manner with any of the other components of the pharmaceutical formulation in which it is contained. The carrier would naturally be selected to minimize any degradation of the active ingredient and to minimize any adverse side effects in the patient, as would be well known to one of skill in the art. See Remington's Pharmaceutical Sciences, 18th ed., Gennaro, A R. Ed., Mack Publishing, Easton Pa. (1990), which discloses typical carriers and conventional methods of preparing pharmaceutical compositions that can be used in conjunction with the preparation of formulations of the agents described herein. It will be apparent to those persons skilled in the art that certain carriers can be more preferable depending upon, for instance, the route of administration and concentration of composition being administered.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate and the like. Liquid pharmaceutically administrable compositions can, for example, be prepared by dissolving, dispersing, etc., an active agent as described herein and optional pharmaceutical adjuvants in an excipient, such as, for example, water, saline aqueous dextrose, glycerol, ethanol and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art.

The disclosed agents can also be present in liquids, emulsions, or suspensions for delivery of active therapeutic agents. Liquid pharmaceutically administrable compositions can, for example, be prepared by dissolving, dispersing, etc., an active agent as described herein and optional pharmaceutical adjuvants in an excipient, such as, for example, water, saline aqueous dextrose, glycerol, ethanol and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see Remington's Pharmaceutical Sciences, 18th ed., Gennaro, A R. Ed., Mack Publishing, Easton Pa. (1990).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

The disclosed agents can also be present in liquids, emulsions, or suspensions for delivery of active therapeutic agents in aerosol form to cavities of the body such as the nose, throat, or bronchial passages. The ratio of agents to the other compounding agents in these preparations will vary as the dosage form requires.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the agents in combination with a pharmaceutically acceptable carrier and, in addition, can include other medicinal agents, pharmaceutical agents, carriers, adjuvants, diluents, etc.

When the agents are to be delivered into a mammal other than a human, the mammal can be a non-human primate, horse, pig, rabbit, dog, sheep, goat, cow, cat, guinea pig, or rodent. The terms human and mammal do not denote a particular age or sex. Thus, adult and newborn subjects, as well as fetuses, whether male or female, are intended to be covered. A patient, subject, human or mammal refers to a subject afflicted with a disease or disorder. The term "patient" includes human and veterinary subjects.

Kits

Also disclosed are kits comprising the agents be delivered into a human, mammal, or cell. The kits can comprise one or more packaged unit doses of a composition comprising an HPTPβ-ECD binding agent to be delivered into a human, mammal, or cell. The kit optionally includes directions for using the components of the kit. The agents can be packaged as a sterile formulation, and the hermetically sealed container is designed to preserve sterility of the formulation until use.

EXAMPLES

Example 1

Production of the HPTPβ Extracellular Domain Protein

Full length HPTPβ cDNA (SEQ ID NO:1) is cloned from a human placental library according to the manufacturer's (Origene) instructions. A cDNA encoding the entire soluble extracellular domain (ECD) of HPTPβ is cloned by PCR from the full length cDNA coding for amino acids 1-1621 with an added c-terminal His-His-His-His-His-His-Gly (6His-Gly) (SEQ ID NO:3). The resulting cDNA is cloned into mammalian expression vectors for transient (pShuttle-CMV) or stable (pcDNA3.1(−)) expression in HEK293 cells. To obtain purified HPTPβ ECD ((3ED), HEK293 cells transfected with a βECD expression vector are incubated in OptiMEM-serum free (Gibco) for 24 hours under normal growth conditions. The conditioned media is then recovered, centrifuged to remove debris, and 1 mL of washed Ni-NTA agarose (Qiagen) (500 µL packed material) is added to each 10 µL of cleared media and allowed to rock overnight at 4° C. On the following day, the mixture is loaded into a column and washed with 20 bed volumes of 50 mM $NaH_2PO_4$, 300 mM NaCl, 20 mM imidazole, pH 8. The purified HPTPβ extracellular domain protein (SEQ ID NO:4) is then eluted with 200 µL/elution in 50 mM $NaH_2PO_4$, 300 mM NaCl, 250 mM Imidazole, pH 8. Fractions are analyzed for protein content using reducing-denaturing SDS-polyacrylimide gel electrophoresis and detected by silver stain (Invitrogen) and confirmed by mass spectrometry.

Example 2

Purified HPTPβ extracellular domain protein is produced, for example by the procedure described in Example 1. For production of the HPTPβ extracellular domain immunogen, the purified HPTPβ extracellular domain-6-His protein is conjugated to porcine thyroglobulin (Sigma) using EDC coupling chemistry (Hockfield, S. et al., (1993) Cold Spring Harbor Laboratory Press., Vol. 1 pp. 111-201, Immunocytochemistry). The resulting HPTPβ extracellular domain-thyroglobulin conjugate is dialyzed against PBS, pH 7.4. Adult Balb/c mice are then immunized subcutaneously with the conjugate (100-200 µg) and complete Freund's adjuvant in a 1:1 mixture. After 2-3 weeks, the mice are injected intraperitoneally or subcutaneously with incomplete Freund's adjuvant and the conjugate in a 1:1 mixture. The injection is repeated at 4-6 weeks. Sera are collected from mice 7 days post-third-injection and assayed for immunoreactivity to HPTPβ extracellular domain antigen by ELISA and western blotting. Mice that display a good response to the antigen are boosted by a single intra-spleen injection with 50 µl of purified HPTPβ extracellular domain protein mixed 1:1 with Alum hydroxide using a 31 gauge extra long needle (Goding, J. W., (1996) Monoclonal Antibodies: Principles and Practices. Third Edition, Academic Press Limited. p. 145). Briefly, mice are anesthetized with 2.5% avertin, and a 1 centimeter incision is created on the skin and left oblique body wall. The antigen mixture is administered by inserting the needle from the posterior portion to the anterior portion of the spleen in a longitudinal injection. The body wall is sutured and the skin is sealed with two small metal clips. Mice are monitored for safe recovery. Four days after surgery the mouse spleen is removed and single cell suspensions are made for fusion with mouse myeloma cells for the creation of hybridoma cell lines (Spitz, M., (1986) Methods In Enzymology, Vol. 121. Eds. John J, Lagone and Helen Van Vunakis. pp. 33-41 (Academic Press, New York, N.Y.)). Resulting hybridomas are cultured in Dulbeccos modified media (Gibco) supplemented with 15% fetal calf serum (Hyclone) and hypoxathine, aminopterin and thymidine.

Screening for positive hybridomas begins 8 days after the fusion and continues for 15 days. Hybridomas producing anti-HPTPβ extracellular domain antibodies are identified by ELISA on two sets of 96-well plates: one coated with the histidine tagged-HPTPβ extracellular domain and another one coated with a histidine-tagged bacterial MurA protein as a negative control. The secondary antibody is a donkey anti-mouse IgG labeled with horseradish peroxidase (HRP) (Jackson Immunoresearch). Immunoreactivity is monitored in wells using color development initiated by ABTS tablets dissolved in TBS buffer, pH 7.5. The individual HRP reaction mixtures are terminated by adding 100 microliters of 1% SDS and reading absorbance at 405 nm with a spectrophotometer. Hybridomas producing antibodies that interact with HPTPβ extracellular domain-6His, and not with the murA-6His protein are used for further analysis. Limiting dilutions (0.8 cells per well) are performed twice on positive clones in 96 well plates, with clonality defined as having greater than 99% of the wells with positive reactivity. Isotypes of antibodies are determined using the iso-strip technology (Roche). To obtain purified antibody for further evaluation, tissue culture supernatants are affinity purified using a protein A or a protein G column.

Six monoclonal antibodies immunoreactive to HPTPβ-ECD protein were isolated and given the following nomenclature, R15E6, R12A7, R3A2, R11C3, R15G2 and R5A8. Based on its reaction with the HPTPβ-ECD protein in ELISA and in western blots, R15E6 was selected for further study.

Example 3

The Monoclonal Antibody R15E6

The monoclonal antibody R15E6 was identified and characterized as described in Example 2 of the present application and in U.S. Pat. No. 7,973,142; the procedure and results are summarized below.
A. R15E6 Binds Endogenous HPTPβ as Demonstrated by Demonstrated by Immunoprecipitation.

Materials: Human umbilical vein endothelial cells (HUVECs), EGM media, and trypsin neutralizing solution from Cambrex; OPTIMEM I (Gibco), bovine serum albumin (BSA; Santa Cruz), phosphate buffered saline (PBS; Gibco), Growth Factors including Angiopoietin 1 (Ang1), vascular endothelial growth factor (VEGF) and fibroblast growth factor (FGF) (R&D Systems), Tie2 monoclonal antibody (Duke University/P&GP), VEGF receptor 2 (VEGFR2) polyclonal antibody (Whitaker et. al), protein A/G agarose (Santa Cruz), Tris-Glycine pre-cast gel electrophoresis/transfer system (6-8%) (Invitrogen), PVDF membranes (Invitrogen), lysis buffer (20 mm Tris-HCl, 137 mm NaCl, 10% glycerol, 1% triton-X-100, 2 mM EDTA, 1 mM NaOH, 1 mM NaF, 1 mM PMSF, 1 µg/ml leupeptin, 1 µg/ml pepstatin).

Method: HUVECs are pre-treated for 30 min with antibody (in OPTIMEM) or OPTIMEM I alone. After removal of pre-treatment, cells are treated with Ang1 (100 ng/ml) for 6 minutes in PBS+0.2% BSA and lysed in lysis buffer. Lysates are run directly on a Tris-Glycine gel or immunoprecipitated with 2-5 µg/ml Tie-2 antibody or 10 µg/ml R15E6 antibody and protein A/G agarose. Immunoprecipitated samples are rinsed once with lysis buffer and boiled for 5 min in 1× times sample buffer. Samples are resolved on a Tris-Glycine gel, transferred to a PVDF membrane, and detected by western blot using the indicated antibodies (pTYR Ab (PY99, Santa Cruz), Tie-2, VEGFR2 and/or R15E6).

Results: By IP/western blotting, R15E6 recognizes a major, high molecular weight band consistent with the size of HPTPβ (FIG. 1, Panel A, Lane 2). The less intense, lower molecular weight bands likely represent less glycosylated precursor forms of HPTPβ. An immunoprecipitation (IP)

with control, non-immune IgG shows no bands in the molecular weight range of HPTPβ (FIG. 1, Panel A, Lane 1), and a combined Tie2/VEGFR2 IP shows bands of the expected molecular weight (FIG. 1, Panel A, Lane 3). This result demonstrates that R15E6 recognizes and is specific for HPTPβ.

B. R15E6 Binds Endogenous HPTPβ as Demonstrated by FACS Analysis

Materials: HUVECs, EGM media, and trypsin neutralizing solution from Cambrex; Secondary Alexfluor 488-tagged antibody from Molecular Probes; Hanks balanced salt solution (Gibco); FACSCAN flow cytometer and CellQuest software from Becton Dickenson.

Method: HUVECs are trypsinized, treated with trypsin neutralizing solution and rinsed with HBSS. R15E6 antibody (0.6 µg) is added to 250,000 cells in 50 µl of HBSS and incubated on ice for 20 minutes. Cells are rinsed with 1 ml HBSS followed by adding 2 µg of fluorescent-conjugated secondary antibody for 20 minutes on ice. Cells are rinsed and resuspended in 1 ml HBSS then analyzed on the FACSCAN flow cytometer with CellQuest software. Control cells are treated with fluorescent-conjugated secondary antibody only.

Results: By FACS analysis, intact HUVECs, R15E6 causes a robust shift (>90% of cells) in the fluorescence signal compared to the secondary antibody alone (FIG. 1, Panel B). This result indicates that R15E6 binds to endogenous HPTPβ presented on the surface of intact endothelial cells.

Example 4

R15E6 Enhances Tie2 Activation

R15E6 enhances Tie2 phosphorylation in the absence and presence of the angiopoietin 1 (Ang1), the Tie2 ligand.

Methods: HUVECs are cultured in serum free media as described above in the presence or absence of various concentrations of R15E6 and with or without added Ang1. Lysates are prepared, immunoprecipitated with a Tie2 antibody, resolved by polyacrylamide gel electrophoresis and transferred to a PVDF membrane. Membrane-bound immunoprecipitated proteins are then serially western blotted with an antiphosphotyrosine antibody to quantify Tie2 phosphorylation followed by a Tie2 antibody to quantify total Tie2. Tie2 phosphorylation is expressed as the ratio of the antiphosphotyrosine signal over the total Tie2 signal.

Figure 2:
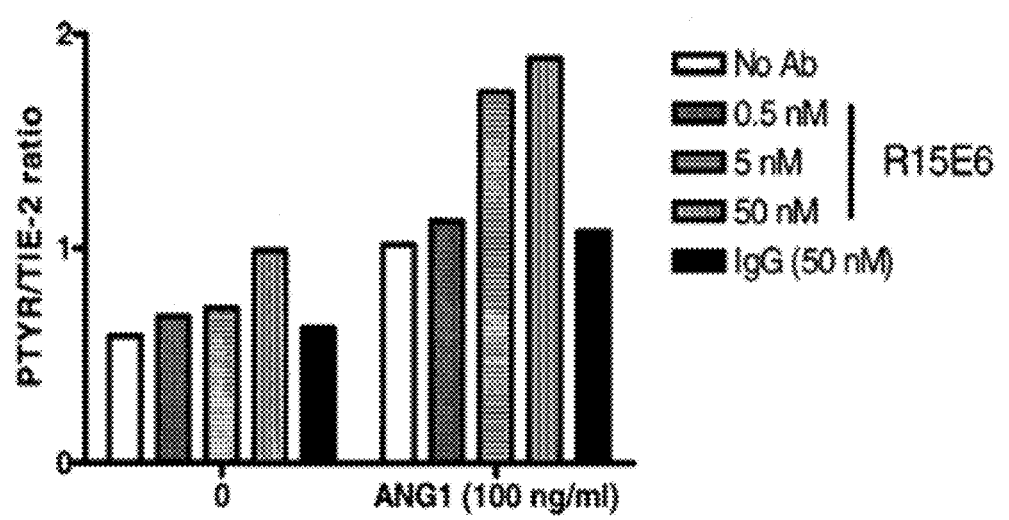
FIG. 2 The monoclonal antibody R15E6 enhances Tie2 Receptor Activation in HUVECs. Tie2 activation is measured in human endothelial cells as described in Example 4. R15E6 dose dependently enhances both basal and Ang1-induced Tie2 activation.

Results: R15E6 enhances Tie2 phosphorylation both in the absence and presence of Ang1 (FIG. 2). This result indicates that binding of R15E6 to HPTPβ on the surface of endothelial cells modulates its biological function resulting in enhanced activation of Tie2 in the absence or presence of ligand.

Example 5

Generation of Anti-VE-PTP Extracellular Domain Antibodies

A. Production of Mouse VE-PTP Extracellular Domain Protein (VE-PTP-ECD)

VE-PTP-ECD may be produced by any suitable method. Such methods are well known in the art. For example, VE-PTP-ECD can be produced using a method similar to Example 1 of the present disclosure where VE-PTP-ECD cDNA is used in place of cDNA encoding HPTPβ-ECD. SEQ ID NO: 5 provides a nucleotide sequence that encodes VE-PTP-ECD. SEQ ID NO: 7 provides the amino acid sequence of VE-PTP-ECD.

B. Generation of Antibodies to VE-PTP ECD

Anti-VE-PTP antibodies are readily generated by methods that are well known in the art. For example, anti VE-PTP antibodies can be generated using the method of Example 2 of the present disclosure by substituting VE-PTP-ECD for the HPTPβ extracellular domain and immunizing rats with the resulting protein. The rat anti-mouse VE-PTP antibody used in the present studies was kindly provided by Dr. D. Vestweber (mAb 109). The antibody was generated as described in Baumer S. et al., Blood, 2006, Vol. 107, pp. 4754-4762. Briefly, the antibody was generated by immunizing rats with a VE-PTP-Fc fusion protein. Immunization, hybridoma-fusion, and screening were conducted as described in Gotsch U., et al., J Cell Sci., 1997, Vol. 110, pp. 583-588 and Bosse R. and Vestweber D., Eur J Immunol., 1994, Vol. 24, pp. 3019-3024.

The fusion protein was constructed such that the first 8 fibronectin type III-like repeats ending with the amino acid proline at position 732 of VE-PTP were fused in frame with the Fc part of human IgG1 (starting with amino acid proline at position 239). This construct cloned into pcDNA3 (Invitrogen) was stably transfected into CHO cells, and the fusion protein was purified by protein A Sepharose affinity purification.

Example 6

Intravitreal Injections of an Anti-VE-PTP ECD Antibody

Figure 3:
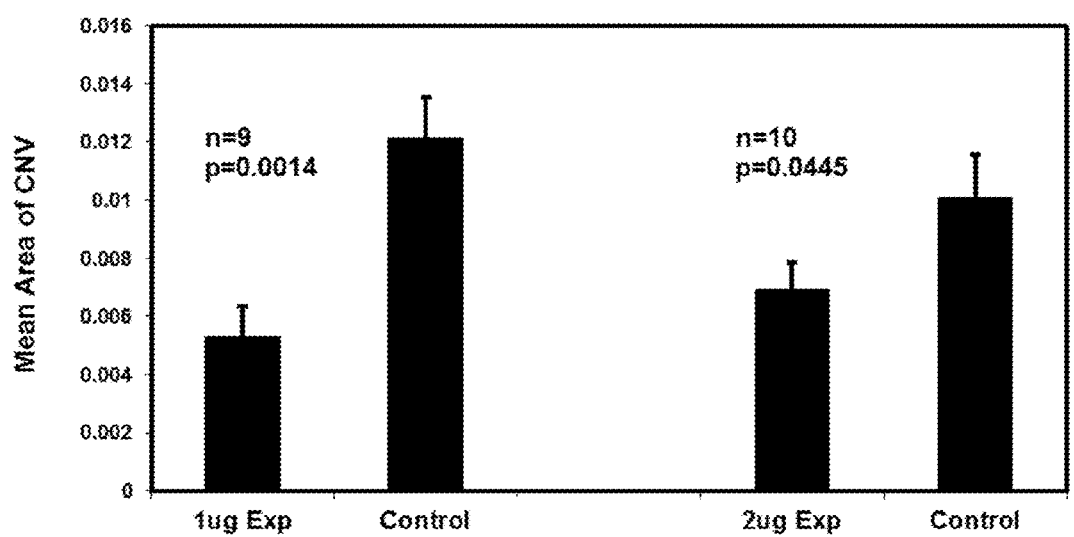
FIG. 3. Is a graphical representation of the mean area of choroidal neovascularization in C57BL/6 mice 14 days post laser treatment in eyes treated with intravitreal injection of 1 µg or 2 µg of an anti-VE-PTP extracellular domain antibody in one eye versus similar treatment of the fellow eye with vehicle.

Laser-induced Choroidal Neovascularization Model: The choroidal neovascularization model is considered to represent a model of neovascular age-related macular degeneration. Choroidal Nev. was generated as previously described. See Tobe T, et al., Am. J. Pathol., 1998, Vol. 153, pp. 1641-1646. Adult C57BL/6 mice had laser-induced rupture of Bruch's membrane in three locations in each eye and were then given 1 µL intravitreal injections of 1 or 2 µg of a rat anti-mouse VE-PTP-ECD antibody (IgG2a), in one eye and vehicle (5% dextrose) in the fellow eye. These treatments were repeated on day 7. Fourteen days after laser, the mice were perfused with fluorescein-labeled dextran ($2 \times 10^6$ average MW, Sigma, St. Louis, Mo.) and the extent of neovascularization was assessed in choroidal flat mounts by fluorescence microscopy. The area of CNV at each Bruch's membrane rupture site was measured by image analysis by an observer masked with respect to treatment group. The area of CNV is the average of the three rupture sites in one eye. As shown in FIG. 3, treatment with the VE-PTP-ECD antibody significantly reduced choroidal neovascularization at both 1 and 2 mg doses versus treatment with vehicle control.

Example 7

Oxygen-Induced Ischemic Retinopathy

The oxygen-induced ischemic retinopathy model is considered to represent a model of proliferative diabetic retinopathy. Ischemic retinopathy was produced in C57BL/6 mice by a method described by Smith, L. E. H., et al. Oxygen-induced retinopathy in the mouse. Invest. Ophthalmol. Vis. Sci. 35, 101-111 (1994).

Figure 4:
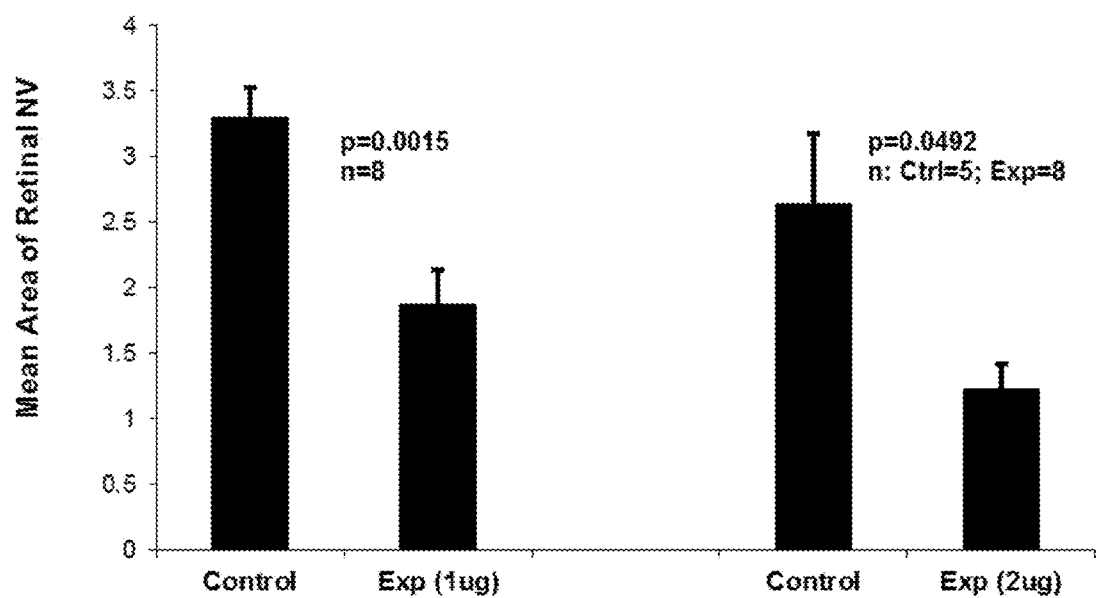
FIG. 4. Shows the mean area ($mm^2$) of retinal neovascularization in C57BL/6 mice on day P17 after containment in a 75% oxygen atmosphere from P5 to P12 and intravitreal injection of an anti-VE-PTP extracellular domain antibody at P12 when the mice were returned to room air.
Figure 5:
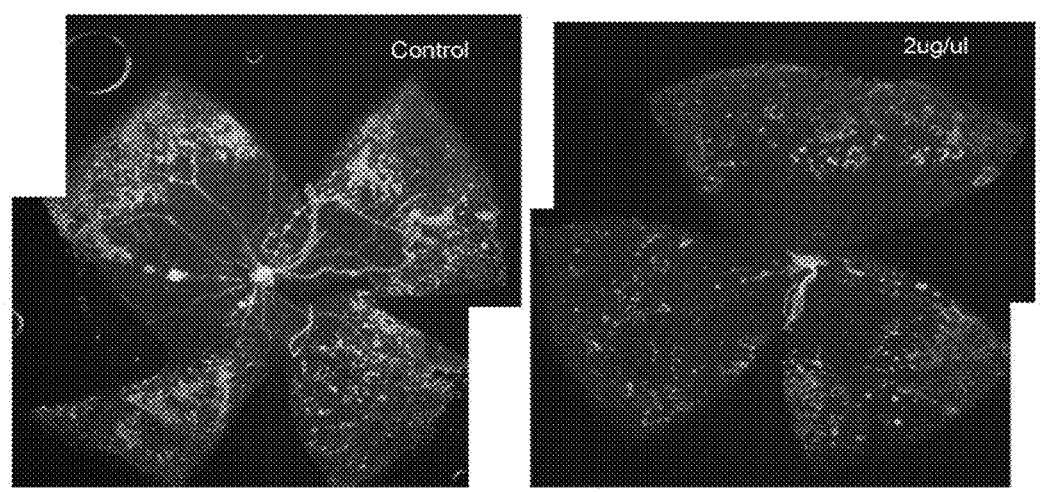
FIG. 5. Show representative fluorescent micrographs of mouse retinas in the oxygen-induced retinopathy model after intravitreal injection of vehicle or 2 µg of an anti-VE-PTP extracellular domain antibody.

C57BL/6 mice at postnatal day 7 (P7) and their mothers were placed in an airtight chamber and exposed to hyperoxia (75±3% oxygen) for five days. Oxygen was continuously monitored with a PROOX model 110 oxygen controller (Reming Bioinstruments Co., Redfield, N.Y.). On P12, mice were returned to room air and under a dissecting microscope, a Harvard Pump Microinjection System and pulled glass pipettes were used to deliver a 1 µl intravitreal injection of 1 or 2 µg of a VE-PTP-ECD antibody was made in one eye and vehicle was injected in the fellow eye. At P17, the area of NV on the surface of the retina was measured at P17 as previously described. See Shen J, et al., Invest. Ophthalmol. Vis. Sci., 2007, Vol. 48, pp. 4335-4341. Briefly, mice were given an intraocular injection of 1 µl containing 0.5 µg rat anti-mouse PECAM antibody (Pharmingen, San Jose, Calif.). Twelve hours later, the mice were euthanized, the eyes fixed in 10% formalin. The retinas were dissected, incubated for 40 minutes in 1:500 goat anti-rat IgG conjugated with Alexa488 (Invitrogen, Carlsbad, Calif.), washed, and whole mounted. An observer masked with respect to treatment group examined the slides with a Nikon Fluorescence microscope and measured the area of NV per retina by computerized image analysis using ImagePro Plus software (Media Cybernetics, Silver Spring, Md.). FIG. 4 shows that treatment with the VE-PTP-ECD antibody significantly reduced retinal neovascularization at both 1 and 2 µg doses versus treatment with vehicle control. FIG. 5 shows representative retinal whole mounts from a mouse treated with vehicle versus a mouse treated with 2 µg of the VE-PTP-ECD antibody.

Example 8

Subcutaneous Injection of a VE-PTP-ECD Antibody

Figure 6:
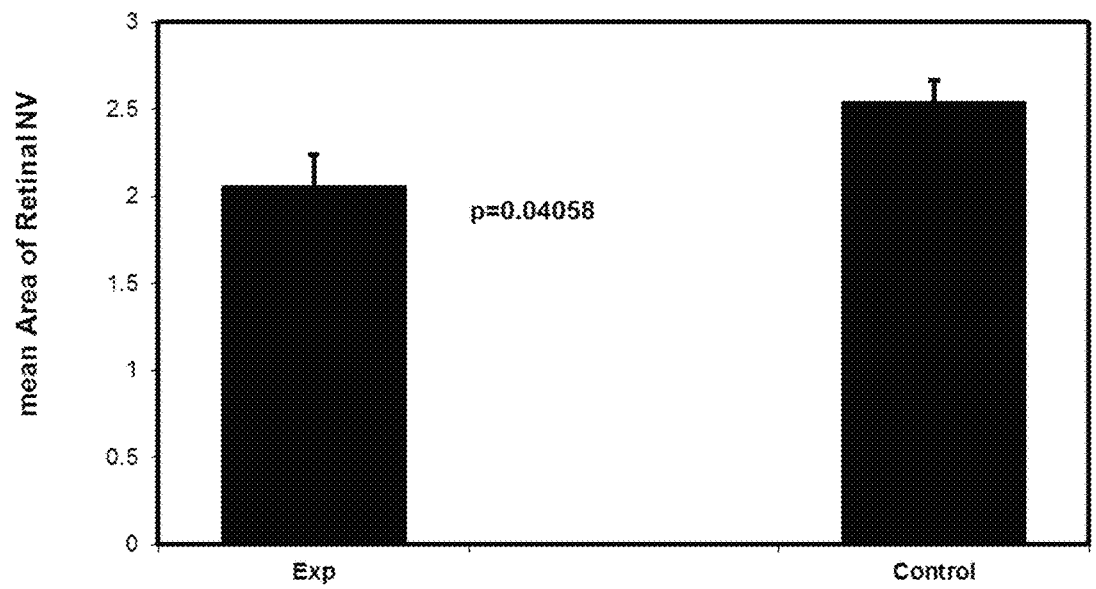
FIG. 6. Shows the mean area ($mm^2$) of retinal neovascularization in C57BL/6 mice on day P17 after containment in a 75% oxygen atmosphere from P5 to P12 followed by return to room air on P12 with subcutaneous administration of 1 mg/kg of an anti-VE-PTP extracellular domain antibody on days P12, 14 and 16.

The oxygen-induced ischemic retinopathy model was conducted as described in Example 7 (containment in a 75% oxygen atmosphere from P5 to P12) for intravitreal dosing except that the VE-PTP-ECD antibody (1 mg/kg) was dosed subcutaneously at P12 when the mice were returned to room air and again on days P14 and P16 (three total doses). Neovascularization was assessed as described above on day (P17). FIG. 6 shows that subcutaneous dosing of the VE-PTP-ECD antibody reduces the area of retinal neovascularization.

Example 9

Figure 7:
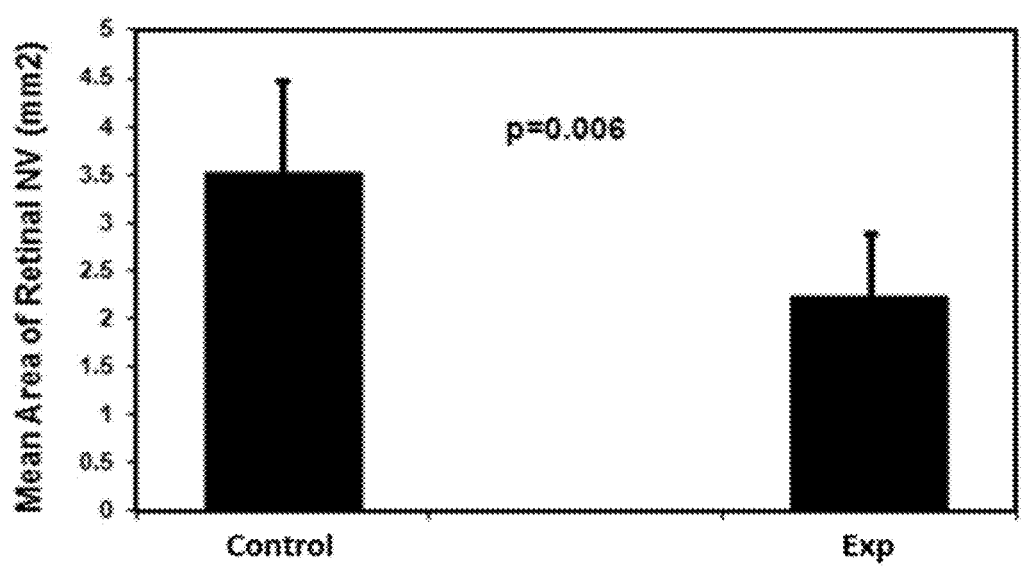
FIG. 7. Shows the mean area ($mm^2$) of retinal neovascularization in C57BL/6 mice on day P17 after containment in a 75% oxygen atmosphere from P5 to P12 follow by return to room air on P12 with subcutaneous administration of 2 mg/kg of an anti-VE-PTP extracellular domain antibody on days P12, 14 and 16.

The experiment described in Example 8 was repeated at a subcutaneous dose of 2 mg/kg. (FIG. 7)

While a number of embodiments of this disclosure are described, it is apparent that the basic examples may be altered to provide other embodiments that utilize or encompass the HPTPβ-ECD binding agent, methods and processes of this invention. The embodiments and examples are for illustrative purposes and are not to be interpreted as limiting the disclosure, but rather, the appended claims define the scope of this invention.

The invention claimed is:

1. A method for reducing vascular leak syndrome in an eye of a human having vascular leak in the eye, comprising administering to the human having vascular leak a composition comprising an effective amount of an HPTPβ-ECD binding agent, wherein the HPTPβ-ECD binding agent is an intact monoclonal antibody, wherein the HPTPβ-ECD binding agent is R15E6 or a humanized form thereof, wherein the HPTPβ-ECD binding agent is administered once daily, three-times weekly, twice weekly, once weekly, three times monthly, twice monthly, once monthly, or once every other month.

2. The method according to claim 1, wherein the HPTPβ-ECD binding agent is administered in combination with an additional therapeutic agent, wherein the HPTPβ-ECD binding agent and the additional therapeutic agent are administered together or in any order.

3. The method according to claim 2, wherein the additional therapeutic agent is IL-2.

4. The method according to claim 1, wherein the effective amount of the HPTPβ-ECD binding agent is from about 0.01 mg/kg to about 10 mg/kg by weight of the human.

5. The method according to claim 1, wherein the HPTPβ-ECD binding agent is administered by intravenous injection or subcutaneous injection.

6. The method of claim 1, wherein the HPTPβ-ECD binding agent is administered by intravitreal injection.

7. The method of claim 1, wherein the HPTPβ-ECD binding agent is administered once daily.

8. The method of claim 1, wherein the HPTPβ-ECD binding agent is administered three-times weekly.

9. The method of claim 1, wherein the HPTPβ-ECD binding agent is administered twice weekly.

10. The method of claim 1, wherein the HPTPβ-ECD binding agent is administered once weekly.

11. The method of claim 1, wherein the HPTPβ-ECD binding agent is administered three times monthly.

12. The method of claim 1, wherein the HPTPβ-ECD binding agent is administered twice monthly.

13. The method of claim 1, wherein the HPTPβ-ECD binding agent is administered once monthly.

14. The method of claim 1, wherein the HPTPβ-ECD binding agent is administered once every other month.

* * * * *